US009848587B2

(12) United States Patent
Macdonald et al.

(10) Patent No.: US 9,848,587 B2
(45) Date of Patent: Dec. 26, 2017

(54) HUMANIZED T CELL CO-RECEPTOR MICE

(71) Applicant: Regeneron Pharmaceuticals, Inc., Tarrytown, NY (US)

(72) Inventors: Lynn Macdonald, Harrison, NY (US); Andrew J. Murphy, Croton-on-Hudson, NY (US); Naxin Tu, Pleasantville, NY (US); Cagan Gurer, Chappaqua, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/185,301

(22) Filed: Feb. 20, 2014

(65) Prior Publication Data

US 2014/0245466 A1    Aug. 28, 2014

Related U.S. Application Data

(60) Provisional application No. 61/766,762, filed on Feb. 20, 2013, provisional application No. 61/890,915, filed on Oct. 15, 2013.

(51) Int. Cl.
*A01K 67/027* (2006.01)
*C07K 14/725* (2006.01)
*C07K 14/74* (2006.01)
*C07K 14/73* (2006.01)
*C07K 14/705* (2006.01)
*C12N 15/85* (2006.01)

(52) U.S. Cl.
CPC .... *A01K 67/0278* (2013.01); *C07K 14/70514* (2013.01); *C07K 14/70517* (2013.01); *C12N 15/8509* (2013.01); *A01K 2207/15* (2013.01); *A01K 2217/072* (2013.01); *A01K 2267/03* (2013.01); *C07K 14/70539* (2013.01)

(58) Field of Classification Search
CPC .......... A01K 2217/05; A01K 2217/072; A01K 2217/15; A01K 2227/105; A01K 2267/03; C07K 14/70517; C07K 14/70539
USPC ...................................... 800/13, 18; 530/324
See application file for complete search history.

(56) References Cited

U.S. PATENT DOCUMENTS

| | | | |
|---|---|---|---|
| 5,413,923 A | 5/1995 | Kucherlapati et al. | |
| 5,416,260 A | 5/1995 | Koller et al. | |
| 5,574,205 A | 11/1996 | Kucherlapati et al. | |
| 5,644,065 A | 7/1997 | Benoist et al. | |
| 5,859,312 A | 1/1999 | Littman et al. | |
| 5,965,787 A | 10/1999 | Luthra et al. | |
| 6,002,066 A | 12/1999 | Leung et al. | |
| 6,139,835 A | 10/2000 | Kucherlapati et al. | |
| 6,150,584 A | 11/2000 | Kucherlapati et al. | |
| 6,270,772 B1 | 8/2001 | Burrows et al. | |
| 6,372,955 B1 | 4/2002 | Karlsson et al. | |
| 6,514,752 B1 | 2/2003 | Kucherlapati et al. | |
| 6,586,251 B2 | 7/2003 | Economides et al. | |
| 6,596,541 B2 | 7/2003 | Murphy et al. | |
| 6,815,171 B2 | 11/2004 | Burrows et al. | |
| 7,105,348 B2 | 9/2006 | Murphy et al. | |
| 7,265,218 B2 | 9/2007 | Burrows et al. | |
| 7,294,754 B2 | 11/2007 | Poueymirou et al. | |
| 7,339,089 B2 | 3/2008 | Gotoh | |
| 7,663,017 B2 | 2/2010 | Lone et al. | |
| 7,745,690 B2 | 6/2010 | Kanazawa et al. | |
| 2002/0164721 A1 | 11/2002 | Firat et al. | |
| 2003/0093818 A1 | 5/2003 | Belmont et al. | |
| 2005/0050580 A1 | 3/2005 | Gotoh | |
| 2005/0066375 A1* | 3/2005 | Thiam et al. | 800/8 |
| 2005/0114910 A1 | 5/2005 | Lone et al. | |
| 2006/0107339 A1 | 5/2006 | Gotoh | |
| 2007/0209083 A1 | 9/2007 | Thiam et al. | |
| 2009/0328240 A1 | 12/2009 | Sing et al. | |
| 2010/0011450 A1 | 1/2010 | Garcia et al. | |
| 2010/0138938 A1 | 6/2010 | Garcia et al. | |
| 2011/0067121 A1 | 3/2011 | Lone et al. | |
| 2013/0111616 A1 | 5/2013 | Macdonald et al. | |
| 2013/0111617 A1 | 5/2013 | Macdonald et al. | |
| 2013/0185819 A1 | 7/2013 | Macdonald et al. | |
| 2013/0185820 A1 | 7/2013 | Macdonald et al. | |
| 2014/0245467 A1 | 8/2014 | Macdonald et al. | |
| 2015/0342163 A1 | 12/2015 | Voronina et al. | |

FOREIGN PATENT DOCUMENTS

| | | |
|---|---|---|
| EP | 0437576 A1 | 7/1991 |
| EP | 0950707 A1 | 10/1999 |
| EP | 1017721 A1 | 7/2000 |
| EP | 1409646 A2 | 4/2004 |
| EP | 1878342 A1 | 1/2008 |
| EP | 1878798 A1 | 1/2008 |
| WO | WO-91/01140 A1 | 2/1991 |

(Continued)

OTHER PUBLICATIONS

Sherman et al. (1992) Science, vol. 258, 815-818.*
Koller et al. (1985) J. Immunol., vol. 134(4), 2727-2733.*
Nakayama et al. (1992) J. Immunol., vol. 148, 1919-1927.*
Nakayama et al. (1989) Immunogenetics, vol. 30, 393-397.*
Lalor et al. (1992) Immunology, vol. 76, 95-102.*
Allen, H. et al., B2-Microglobulin is not required for cell surface expression of the murine class I histocompatibility antigen H-2Db or of a truncated H-2Db, Proceedings of the National Academy of Sciences of the U.S.A., 83:7447-7451 (1986).
Altmann, D.M. et al., The T Cell Response to HLA-DR Transgenic Mice to Human Myelin Basic Protein and other Antigens in the Presence and Absence of Human CD4, Journal of Experimental Medicine, 181:867-875 (1995).
Alvarez, J.D. et al., V(D)J Recomination and Allelic Exclusion of a TCR β-Chain Minilocus Occurs in the Absence of a Functional Promoter, The Journal of Immunology, 155:1191-1202 (1995).
Arnold, B. et al., MHC Class-I Transgenic Mice, Annual Review of Immunology, 9:297-322 (1991).

(Continued)

Primary Examiner — Anne Marie S Wehbe
(74) Attorney, Agent, or Firm — Brownstein Hyatt Farber Schreck, LLP; Rita S. Wu; Margarita Zippin

(57) ABSTRACT

The invention provides genetically modified non-human animals that express chimeric human/non-human T cell co-receptor polypeptides (e.g., CD4, CD8α, CD8β), as well as embryos, cells, and tissues comprising the same. Also provided are constructs for making said genetically modified animals and methods of making the same.

28 Claims, 7 Drawing Sheets

(56) References Cited

FOREIGN PATENT DOCUMENTS

| | | |
|---|---|---|
| WO | WO-92/11753 A1 | 7/1992 |
| WO | WO-93/05817 A1 | 4/1993 |
| WO | WO-95/03331 A1 | 2/1995 |
| WO | WO-97/32603 A1 | 9/1997 |
| WO | WO-98/24893 A2 | 6/1998 |
| WO | WO-01/27291 A1 | 4/2001 |
| WO | WO-02/059263 A2 | 8/2002 |
| WO | WO-03/006639 A1 | 1/2003 |
| WO | WO-2005/004592 A2 | 1/2005 |
| WO | WO-2008/010099 A2 | 1/2008 |
| WO | WO-2008/010100 A2 | 1/2008 |
| WO | WO-2009/114400 A1 | 9/2009 |
| WO | 2011004192 A1 | 1/2011 |
| WO | WO-2012/039779 A1 | 3/2012 |
| WO | WO-2013/063340 A1 | 5/2013 |
| WO | WO-2013/063346 A1 | 5/2013 |
| WO | 2014130667 A1 | 8/2014 |
| WO | 2014164640 A1 | 10/2014 |

OTHER PUBLICATIONS

Auerbach, W. et al., Establishment and Chimera Analysis of 129/SvEV- and C57BL/6-Derived Mouse Embryonic Stem Cell Lines, BioTechniques, 29:1024-1032 (2000).

Baker, A.M. et al., Adaptation of TCR Expression Vectors for the Construction of Mouse-Human Chimeric MBP-Specific TCR Transgenes, Journal of Neuroscience Research, 45:487-491 (1996).

Basha, G. et al., MHC class I endosomal and lysosomal trafficking coincides with exogenous antigen loading in dendritic cells, PLoS One, 3(9):e3247 (2008).

Bassing, C.H. et al., Recombination signal sequences restrict chromosomal V(D)J recombination beyond the 12/23 rule, Nature, 405:583-586 (2000).

Benmohamed, L. et al., Induction of CTL Response by a Minimal Epitope Vaccine in HLA-A*0201/DR1 Transgenic Mice: Dependence on HLA Class II Restricted TH Response, Hum. Immunol., 61:764-779 (2000).

Bernabeu, C. et al., B2-Microglobulin from serum associates with MHC class I antigens on the surface of cultured cells, Nature, 308:642-645 (1984).

Betser-Cohen, G. et al., The Association of MHC Class I Proteins with the 2B4 Receptor Inhibits Self-Killing of Human NK Cells, Journal of Immunology, 184:2761-2768 (2010).

Bonnet, M. et al., Molecular Genetics at the T-Cell Receptor β Locus: Insights into the Regulation of V(D)J Recombination, V(D)J Recombination, 650:116-132 (2009).

Bouffard, G.G. et al., A Physical Map of Human Chromosome 7: An Integrated YAC Contig Map with Average STS Spacing of 79 kb, Genome Research, 7:673-692 (1997).

Carstea, A.C. et al., Germline competence of mouse ES and iPS cell lines: Chimera technologies and genetic background, World Journal of Stem Cells, 1(1):22-29 (2009).

Chamberlain, J.W. et al., Tissue-specific and cell surface expression of human major histocompatibility complex class I heavy (HLA-B7) and light (B2-microglobulin) chain genes in transgenic mice, Proceedings of the National Academy of Sciences of the U.S.A., 86:7690-7694 (1988).

Chung, S. et al., Functional three-domain single-chain T-cell receptors, Proceedings of the National Academy of Sciences of the U.S.A., 91:12654-12658 (1994).

Clark, S. J. et al., Peptide and nucleotide sequences of rat CD4 (W3/25) antigen: evidence for derivation from a structure with four immunoglobulin-related domains, Proceedings of the National Academy of Sciences of the U.S.A., 84(6):1649-1653 (1987).

Connolly, J.M. et al., The Lyt-2 molecule recognizes residues in the class I alpha 3 domain in allogeneic cytotoxic T cell responses, Journal of Experimental Medicine, 168(1):325-341 (1988).

Cooper, J.C. et al., An Impaired Breeding Phenotype in Mice with a Genetic Deletion of Beta-2 Microglobulin and Diminished MHC Class I Expression: Role in Reproductive Fitness, Biology of Reproduction, 77:274-279 (2007).

Corbeil, J. et al., HIV-induced Apoptosis Requires the CD4 Receptor Cytoplasmic Tail and Is Accelerated by Interaction of CD4 with p56lck, Journal of Experimental Medicine, 183:39-48 (1996).

Cosson, P. et al., Role of Transmembrane Domain Interactions in the Assembly of Class II MHC Molecules, Science, 258:659-662 (1992).

Danner, R. et al., Expression of HLA Class II Molecules in Humanized NOD.Rag1KO.IL2RgKO Mice is Critical for Development and Function of Human T and B Cells, PLoS ONE, 6(5):e19826 (12 pages) (2011).

Database entry for NCBI Reference Sequence: NG_001333.2 (Sep. 19, 2006).

De Bakker, P.I. et al., A high-resolution HLA and SNP haplotype map for disease association studies in the extended human MHC, Nature Genetics, 38:1166-1172 (2006).

De Gassart, A. et al., MHC class II stablization at the surface of human dendritic cells is the result of maturation-dependent MARCH 1 down-regulation, Proceedings of the National Academy of Sciences of the U.S.A., 105:3491-3496 (2008).

Dolan, B.P. et al., Invariant chain and the MHC class II cytoplasmic domains regulate localization of MHC class II molecules to lipid rafts in tumor cell-based vaccines, Journal of Immunology, 172(2):907-914 (2004).

El Fakhry, Y. et al., Delineation of the HLA-DR Region and the Residues Involved in the Association with the Cytoskeleton, Journal of Biological Chemistry, 279:18472-18480 (2004).

Ellmeier, W. et al., Multiple developmental stage-specific enhancers regulate CD8 expression in developing thymocytes and in thymus-independent T cells, Immunity, 9(4):485-496 (1998).

Festing, M.F. et al., Revised nomenclature for strain 129 mice, Mammalian Genome, 10:836 (1999).

Firat, H. et al., Comparative analysis of the CD8+ T cell repertoires of H-2 class I wild-ype/HLA-2.1 and H-2 class I knockout/HLA-A2.1 transgenic mice, International Immunolology, 14:925-934 (2002).

Fleischer, B. et al., Reactivity of Mouse T-Cell Hybridomas Expressing Human Vβ Gene Segments with Staphylococcal and Streptococcal Superantigens, Infection and Immunity, 64(3):987-994 (1996).

Fooksman, D.R. et al., Cutting Edge: Phosphotidylinositol 4,5-Bisphosphate Concentration at the APC Side of the Immunological Synapse Is Required for Effector T Cell Function, Journal of Immunology, 182:5179-5182 (2009).

Friese, M.A. et al., Opposing effects of HLA class I molecules in tuning autoreactive CD8+ T cells in multiple scelerosis, Nature Medicine, 14(11): 1227-1235 (2008).

Fugger, L. et al., Expression of HLA-DR4 and human CD4 transgenes in mice determines the variable region beta-chain T-cell repertoire and mediates an HLA-DR-restricted immune response, Proceedings of the National Academy of Sciences of the U.S.A., 91(13): 6151-6155 (1994).

Fukui, Y. et al., Differential requirement of MHC class II molecules expressed on hematopoietic cells for positive selection of CD4+ thymocytes in TCRαβ and TCRβ transgenic mice, International Immunology, 9(9):1385-1391 (1997).

Gao, G.F. et al., Crystal structure of the complex between human CD8αα and HLA-A2, Nature, 387:630-634 (1997).

Gao, G.F. et al., Molecular interactions of coreceptor CD8 and MHC class I: the molecular basis for functional coordination with the T-cell receptor, Immunology Today, 21(12):630-636 (2000).

Germain, R.N. et al., T-Cell Development and the CD4-CD8 Lineage Decision, Nature Reviews, Immunology, 2:309-322 (2002).

Goldman, I.L. et al., Transgenic animals in medicine: Integration and expression of foreign genes, theoretical and applied aspects, Medical Science Monitor, 10(11):RA274-285 (2004).

Gruda, R. et al., Intracellular cysteine residues in the tail of MHC class I proteins are crucial for extracellular recognition by leukocyte Ig-like receptor 1, Journal of Immunology, 179(6):3655-3661 (2007).

(56) References Cited

OTHER PUBLICATIONS

Gur, H. et al., Structural analysis of class I MHC molecules: the cytoplasmic domain is not required for cytoskeletal association, aggregation and internalization, Molecular Immunology, 34(2):125-132 (1997).

Gussow, D. et al., The Human B2-Microglobulin Gene. Primary Structure and Definition of the Transcriptional Unit, Journal of Immunology, 139:3132-3138 (1987).

Haks, M.C. et al., Cell-fate decisions in early T cell development: regulation by cytokine receptors and the pre-TCR, Immunology, 11:23-37 (1999).

Hanna, Z. et al., Specific expression of the human CD4 gene in mature CD4 + CD8- and immature CD4+ and CD8+ T cells and in macrophages of transgenic mice, Molecular and Cellular Biology, 14(2):1084-1094 (1994).

Holdsworth, R. et al., the Hla dictionary 2008: a summary of HLA-A, -B, -C -DRB1/3/4/5, and -DQB1 alleles and their association with serologically defined HLA-A, -B, -C, -DR, and -DQ antigens, Tissue Antigens, 73:95-170 (2009).

Hostert, A. et al., A CD8 genomic fragment that directs subset-specific expression of CD8 in transgenic mice, Journal of Immunology, 158(9):4270-4281 (1997).

Houdebine, L.M., The methods to generate transgenic animals and to control transgene expression, Journal of Biotechnology, 98:145-160 (2002).

Houdebine, L.M., Transgenic Animal Models in Biomedical Research, Methods in Molecular Biology, 360:163-202 (2007).

Huang et al., Analysis of the contact sites on the CD4 Molecule with Class II MHC Molecule, Journal of Immunology, 158:215-225 (1997).

International MHC and Autoimmunity Genetics Network (Imagen), Mapping of multiple susceptibility variants within the MHC region for 7 immune-mediated diseases, Proc. Natl., Acad. Sci. USA, 106:18680-18685 (2009).

International Preliminary Report on Patentability for PCT/US2012/062029, 1 page (Apr. 29, 2014).

International Preliminary Report on Patentability for PCT/US2012/062042, 1 page (Apr. 29, 2014).

International Preliminary Report on Patentability for PCT/US2012/062065, dated May 8, 2014 (8 pages).

International Search Report for PCT/US2012/062042, 6 pages (Apr. 29, 2014).

International Search Report for PCT/US2014/017387, 5 pages (Jun. 2, 2014).

International Search Report for PCT/US2014/017395, 5 pages (Feb. 6, 2014).

International Search Report for PCT/US2014/023068, 5 pages (Jul. 24, 2014).

Irie, H.Y. et al., The cytoplasmic domain of CD8 beta regulates Lck kinase activation and CD8 T cell development, Journal of Immunology, 161(1):183-191 (1998).

Irwin, M.J. et al., Species-restricted interactions between CD8 and the alpha 3 domain of class I influence the magnitude of the xenogeneic response, Journal of Experimental Medicine, 170(4):1091-1101 (1989).

Ishmoto, T. et al., In vitro and in vivo evidence for high frequency of I-Ab-reactive CD4+ T cells in HLA-DQ or HLA-DRA transgenic mice lacking endogenous MHC class I and/or class II expression, The Journal of Immunology, 159(8):3717-3722 (1997).

Itano, A. et al., The Cytoplasmic Domain of CD4 Promotes the Development of CD4 Lineage T Cells, Journal of Experimental Medicine, 183(3):731-741 (1996).

Ito, K. et al., HLA-DR4-IE Chimeric Class II Transgenic, Murine Class II-Deficient Mice Are Susceptible to Experimental Allergic Encephalomyelitis, Journal of Experimental Medicine, 183:2635-2644 (1996).

Jakobivitz, A., Humanizing the mouse genome, Current Biology, 4(8):761-763 (1994).

Johansson, S. et al., Natural killer cell education in mice with single or multiple major histocompatibility complex class I molecules, Journal of Experimental Medicine, 201-1145-1155 (2005).

Johnson, P., A human homolog of the mouse CD8 molecule, Lyt-3: genomic sequence and expression, Immunogenetics, 26(3):174-7 (1987).

Josson, S. et al., B2 microglobulin induces epithelial to mesenchymal transition and confers cancer lethality and bone metastasis in human cancer cells, Cancer Research, 71:1-11 (2011).

Kalinke, U. et al., Srong Xenogeneic HLA Response in Transgenic Mice After Introducing an Alpha3 Domain into HLA B27, Nature 348:642-644 (1990).

Kaplan, B. et al., A new murine tumor model for studying HLA-A2-restricted anti-tumor immunity, Cancer Letters, 224:153-166 (2005).

Khor, B. et al., Allelic exclusion at the TCRβ locus, Current Opinion in Immunology, 14:230-234 (2002).

Killeen, N. et al., Regulated expression of human CD4 rescues helper T cell development in mice lacking expression of endogenous CD4, The EMBO Journal, 12(4): 1547-1553 (1993).

Kioussis, D. et al., Chromatin and CD4, CD8A and CD8B gene expression during thymic differentiation, Nature Reviews Immunology, 2(12):909-919 (2002).

Kirwan, S.E. et al., Killer Cell Ig-Like Receptor-Dependent Signaling by Ig-Like Transcript 2 (ILT2/CD85j/LILRB1/LIR-1), Journal of Immunology, 175:5006-5015 (2005).

Koller, B.H. et al., Normal Development of Mice Deficient in B2M, MHC Class I Proteins, and CD8+ T Cells, Science, 248:1227-1230 (1990).

Koop, B.F. et al., The human T-cell receptor TCRAC/TCRDC (C alpha/C delta) region: organization, sequence, and evolution of 97.6 kb of DNA, Genomics 19(3):478-93 (1994).

Krangel, M.S. et al., Development regulation of V(D)J recombination at the TCR α/δ locus, Immunological Reviews, 165:131-147 (1998).

Kruisbeek, A.M. et al., Branching out to gain control: how the pre-TCR is linked to multiple functions, Review Immunology Today, 21(12):637-644 (2000).

Kumanovics, A. et al., Genomic Organization of the Mammalian MHC, Annual Review of Immunology, 21:629-657 (2003).

Laface, D.M., Human CD8 Transgene Regulation of HLA Recognition by Murine T Cells, Journal of Experimental Medicine, 182:1315-1325 (1995).

Landau, N.R. et al., The envelope glycoprotein of the human immunodeficiency virus binds to the immunoglobulin-like domain of CD4, Nature 334(6178): 159-162 (1988).

Laub, R. et al., A multiple transgenic mouse model with a partially humanized activation pathway for helper T cell responses, Journal of Immunology Methods, 246(1-2):37-50 (2000).

Lauzurica P. and Krangel M.S., Enhancer-dependent and -independent Steps in the Rearrangement of a Human T Cell Receptor Delta Transgene. J Exp Med, 1994,179: 43-55.

Law, Y.M. et al., Human CD4 Restores Normal T Cell Development and Function in Mice Deficient in Murine CD4, Journal of Experimental Medicine, 179(4): 1233-1242 (1994).

Leahy, A structural view of CD4 and CD8, The FASEB Journal, 9:17-25 (1995).

Leduc, I. et al., T Cell Development in TCRβ Enhancer-Deleted Mice: Implications for αβ T Cell Lineage Commitment and Differentiation, Journal of Immunology, 165:1364-1373 (2000).

Lee, J.S. et al., Sequence of an HLA-DR alpha-chain cDNA clone and intron-exon organization of the corresponding gene, Nature, 299:750-752 (1982).

Li, J. et al., Mamu-A*01/Kb transgenic and MHC Class I knockout mice as a tool for HIV vaccine development, Virology, 387:16-28 (2009).

Li, L. et al., Generation of transgenic mice with megabase-sized human yeast artificial chromosomes by yeast spheroplast-embryonic stem cell fusion, Nature Protocols, 8(8):1567-1582 (2013).

Li, L. et al., Transgenic mice with a diverse human T cell antigen receptor repertoire, Nature Medicine, 16(9):1029-1035 (2010).

Lie, Y.S. et al., Advances in quantitative PCR technology: 5' nuclease assays, Current Opinion of Biotechnology, 9:43-48 (1998).

(56) References Cited

OTHER PUBLICATIONS

Linnenbach, A. et al., DNA-transformed murine teratocarcinoma cells: regulation of expression of simian virus 40 tumor antigen in stem versus differentiated cells, Proceedings of the National Academy of Sciences of the U.S.A., 77(8):4875-4879 (1980).
Littman, The Structure of the CD4 and CD8 Genes, Annual Review of Immunology, 5:561-584 (1987).
Lizée, G. et al., Control of dendritic cell cross-presentation by the major histocompatibility complex class I cytoplasmic domain, National Immunology, 4(11):1065-1073 (2003).
Lynch, S. et al., Novel MHC class I structures on exosomes, Journal of Immunology, 183(3):1884-1891 (2009).
Maddon, PJ et al., Structure and expression of the human and mouse T4 genes, Proceedings of the National Academy of Sciences of the U.S.A., 84(24):9155-9159 (1987).
Madsen, L.S. et al., A humanized model for multiple sclerosis using HLA-DR2 and a human T-cell receptor, Nature Genetics, 23:343-347 (1999).
Manz, M.G. et al., Renaissance for mouse models of human hematopoiesis and immunobiology, Nature Immunology, 10(10):1039-1042 (2009).
Marsh, S.G. et al., Nomenclature for factors of the HLA system, Tissue Antigens, 75:291-455 (2010).
McMurry, M.T. et al., Enhancer Control of Local Accessibility to V(D)J Recombinase, Molecular and Cellular Biology, 17(8):4553-4561 (1997).
Mendez, M.J. et al., Functional transplant of megabase human immunoglobulin loci recapitulates human antibody response in mice, Nature Genetics, 15(2):146-156 (1997).
Moir, S. et al., Postbinding events mediated by human immunodeficiency virus type 1 are sensitive to modifications in the D4-transmembrane linker region of CD4, Journal of Virology, 70(11):8019-8028 (1996).
Moldovan et al., CD4 Dimers Constitute the Functional Component Required for T Cell Activation, Journal of Immunology, 169:6261-6268 (2002).
Mombaerts P. et al., Creation of a large genomic deletion at the T-cell antigen receptor β-subunit locus in mouse embryonic stem cells by gene targeting, Proc. Natl. Acad. Sci. USA, 88: 3084-3087 (1991).
Mombaerts, P. et al., Mutations in T-cell antigen receptor genes α and β block thymocyte development at different stages, Nature, 360:225-231 (1992).
Mombaerts, P. et al., Spontaneous Development of Inflammatory Bowel Disease in T Cell Receptor Mutant Mice, Cell, 75:275-282 (1993).
Murphy, K. et al., Janeway's Immunobiology, Garland Science, pp. 125-138 and 196-213 (7th ed. 2008).
Nakayama et al., Recent Duplication of the Two Human CD8 β-chain genes, Journal of Immunology, 148:1919-1927 (1992).
Nickerson, C.L. et al., Expression of HLA-B27 in Transgenic Mice Is Dependent on the Mouse H-2D Genes, Journal of Experimental Medicine, 172:1255-1261 (1990).
Noordzij, J.G. et al., N-terminal truncated human RAG1 proteins can direct T-cell receptor but not immunoglobulin gene rearrangements, Blood, 96(1):203-209 (2000).
Norment et al., Alternatively Spliced mRNA Encodes a Secreted Form of Human CD8α, Characterization of the Human CD8α gene, Journal of Immunology, 142:3312-3319 (1989).
Norment, A.M. et al., A second subunit of CD8 is expressed in human T cells, The EMBO Journal, 7(11):3433-3439 (1988).
Ostrand-Rosenberg, S. et al., Abrogation of tumorigenicity by MHC class II antigen expression requires the cytoplasmic domain of the class II molecule, Journal of Immunology, 147(7):2419-2422 (1991).
Pajot, A. et al., A mouse model of human adaptive immune functions: HLA-A2.1/HLA-DR1-transgenic H-2 class I-/class II-knockout mice, European Journal of Immunology, 34:3060-3069 (2004).

Pasare, C. et al., T cells in mice expressing a transgenic human TCRβ chain get positively selected but cannot be activated in the periphery by signaling through TCR, International Immunology, 13(1):53-62 (2001).
Pascolo, S. et al., HLA-A2.1-restricted Education and Cytolytic Activity of CD8+ T Lymphocytes from Beta 2 Microglobulin (B2m) HLA-A2.1 Monochain Transgenic H-2Db B2m Double Knockout Mice, Journal of Experimental Medicine, 185:2043-2051 (1997).
Perarnau, B.M. et al., Human B2-microglobulin specifically enhances cell-surface expression of HLA Class I molecules in transfected murine cells, Journal of Immunology, 141:1383-1389 (1988).
Pettersen, R.D. et al., The TCR-Binding Region of the HLA Class I alpha2 Domain Signals Rapid Fas-Independent Cell Death: A Direct Pathway for T Cell-Mediated Killing of Target Cells? Journal of Immunology, 160:4343-4352 (1998).
Pittet, M.J. et al., Alpha3 Domain Mutants of Peptide/MHC Class I Multimers Allow the Selective Isolation of High Avidity Tumor-Reactive CD8 T Cells, Journal of Immunology, 171:1844-1849 (2003).
Potter, T.A. et al., Substitution at residue 227 of H-2 class I molecules abrogates recognition by CD8-dependent, but not CD8-independent, cytotoxic T lymphocytes, Nature, 337(6202):73-75 (1989).
Poueymirou, W.T. et al., F0 generation mice fully derived from gene-targeted embryonic stem cells allowing immediate phenotypic analyses, Nature Biotechnology, 25(1):91-99 (2007).
Quinn, D.G. et al., Virus-Specific, CD8+ Major Histocompatibility Complex Class I-Restricted Cytotoxic T Lymphocytes in Lymphocytic Choriomeningitis Virus-Infected B2-Microglobulin-Deficient Mice, Journal of Virology, 71:8392-8396 (1997).
Rack, K.A. et al., A Chromosome 14q11/TCRα/δ Specific Yeast Artificial Chromosome Improves the Detection Rate and Characterization of Chromosome Abnormalities in T-Lymphoproliferative Disorders, Blood, 90(3):1233-1240 (1997).
Raffegerst, S.H. et al., Diverse Hematological Malignancies Including Hodgkin-Like Lymphomas Develop in Chimeric MHC Class II Transgenic Mice, PLoS ONE, 4:e8539, 12 pages (2009).
Ren, D. et al., Construction of bioactive chimeric MHC class I tetramer by expression and purification of human-murine chimeric MHC heavy chain and B2M as a fusion protein in Escherichia coli, Protein Expression and Purification, 50:171-178 (2006).
Rodriguez-Cruz, T.G. et al., Natural splice variant of MHC class I cytoplasmic tail enhances dendritic cell-induced CD8+ T-cell responses and boosts anti-tumor immunity, PLoS One, 6(8):e22939, 10 pages (2011).
Rosano, C. et al., The three-dimensional stucture of B2 microglobulin: Results from X-ray crystallagraphy, Biochimica et Biophysica Acta, 1753:85-91 (2005).
Rothe, J. et al., Functional expression of a human TCRβ gene in transgenic mice, International Immunology, 5(1):11-17 (1993).
Rowen, L. et al., The Complete 685-Kilobase DNA Sequence of the Human β T Cell Receptor Locus, Science, 272:1755-1762 (1996).
Rubio, G. et al., Cross-linking of MHC class I molecules on human NK cells inhibits NK cell function, segregates MHC I from the NK cell synapse, and induces intracellular phosphotyrosines, Journal of Leukocyte Biology, 76:116-124 (2004).
Salter, R.D. et al., A binding site for the T-cell co-receptor CD8 on the alpha 3 domain of HLA-A2, Nature, 345:41-46 (1990).
Salter, R.D. et al., Polymorphism in the α3 domain of HLA-A molecules affects binding to CD8, Nature 338:345-348 (1989).
Sanders, S.K. et al., Mutations in CD8 that affect interactions with HLA class I and monoclonal anti-CD8 antibodies, Journal of Experimental Medicine, 174(2):371-379 (1991).
Santagata, S. et al., The genetic and biochemical basis of Omenn syndrome, Immunological Reviews, 178:64-74 (2000).
Schwarz K. et al., RAG mutations in human B cell negative SCID, Science 274(5284):97-9 (1996).
Sebzda, E. et al., Selection of the T Cell Repertoire, Annual Review of Immunology, 17:829-874 (1999).
Shankarkumar, U. et al., The Human Leukocyte Antigen (HLA) System, International Journal of Human Genetics, 4:91-103 (2004).

(56) References Cited

OTHER PUBLICATIONS

Shin, J.S. et al., Surface expression of MHC class II in dendritic cells in controlled by regulated ubiquitination, Nature, 444:115-118 (2006).
Shinkai Y, et al., RAG-2-deficient mice lack mature lymphocytes owing to inability to initiate V(D)J rearrangement. Cell 68(5):855-67 (1992).
Shinohara, E.T. et al., Active integration: new strategies for transgenesis, Transgenic Research, 16:333-339 (2007).
Shiroishi, M. et al., Human inhibitory receptors Ig-like transcript 2 (ILT2) and ILT4 complete with CD8 for MHC class I binding and bind preferentially to HLA-G, Proceedings of the National Academy of Sciences of the U.S.A., 100:8856-8861 (2003).
Shultz, L. et al., Humanized mice in translational biomedical research, Nature Reviews, 7:118-130 (2007).
Sigmund, C.D., Viewpoint: Are Studies in Genetically Altered Mice Out of Control?, Arteriosclerosis, Thrombosis, and Vascular Biology, 20:1425-1429 (2000).
Sims, A. et al., Genetic Susceptibility to Ankylosing Spondylitis Current Molecular Medicine, vol. 4, No. 1 (Feb. 2004).
Singer, A. et al., Lineage fate and intense debate: myths, models and mechanisms of CD4/CD8 lineage choice, Nature Reviews Immunology, 8(10):788-801 (2008).
Siu, G. et al., A transcriptional silencer controls the developmental expression of the CD4 gene, The EMBO Journal, 13(15): 3570-3579 (1994).
Sleckman, B.P. et al., Mechanisms that direct ordered assembly of T cell receptor β locus V, D, and J gene segments, Proceedings of the National Academy of the Sciences of the U.S.A., 97(14):7975-7980 (2000).
Smiley, S.T. et al, Transgenic mice expressing MHC Class II molecules with truncated A-beta cytoplasmic domains reveal signaling-independent defects in antigen presentation, International Immunology, 7:665-677 (1995).
Smiley, S.T. et al., Truncation of the class II beta-chain cytoplasmic domain influences the level of class II/invariant chain-derived peptide complexes, Proceedings of the Natitional Academy of Sciences of the U.S.A., 93(1):241-244 (1996).
Street, M.D. et al., Limitations of HLA-transgenic mice in presentation of HLA-restricted cytotoxic T-cell epitopes from endogenously processed human papillomavirus type 16 E7 protein, Immunology, 106:526-536 (2002).
Takaki, T. et al., HLA-A*0201-Restricted T Cells from Humanized NOD Mice Recognize Autoantigens of Potential Clinical Relevance to Type I Diabetes, Journal of Immunology, 176:3257-3265 (2006).
Tanabe, M. et al., Analysis of Xenoantigenicity of HLA Class I Molecules by a Complete Series of Human-Mouse Hybrid Genes, Transplantation, 48(1): 135-140 (1989).
Taneja, V. et al., HLA Transgenic Mice as Humanized Mouse Models of Disease and Immunity, Perspectives, Journal of Clinical Investigation, 101(5):921-926 (1998).
Taylor, L.D. et al., Human immunoglobulin transgenes undergo rearrangement, somatic mutation and class switching in mice that lack endogenous IgM, International Immunology, 6(4):579-591 (1994).
Tishon, A. et al., Transgenic Mice Expressing Human HLA and CD8 Molecules Generate HLA-Restricted Measles Virus Cytotoxic Lymphocytes of the Same Specificity as Humans and Natural Measles Infection, Virology, 275:286-293 (2000).
Toyonaga B. et al., Organization and sequences of the diversity, joining, and constant region genes of the human T-cell receptor beta chain, Proc Natl Acad Sci USA. 82(24):8624-8 (1985).
Ureta-Vidal, A. et al., Phenotypical and Functional Characterization of the CD8 + T Cell Repertoire of HLA-A2.1 Transgenic, H-2Kb°Db° Double Knockout Mice, Journal of Immunology, 163:2555-2560 (1999).
Valenzuela, D.M. et al., High-throughout engineering of the mouse genome coupled with high-resolution expression analysis, Nature Biotechnology, 21(6):652-659 (2003).

Vignali, D. et al., Species-specific Binding of CD4 to the Beta2 Domain of Major Histocompatibility Complex Class II Molecules, Journal of Experimental Medicine, 175:925-932 (1992).
Vignali, D.A.A. et al., The Two Membrane Proximal Domains of CD4 Interact with the T Cell Receptor, Journal of Experimental Medicine, 183:2097-2107 (1996).
Villa, A. et al., Omenn syndrome: a disorder of Rag1 and Rag2 genes, Journal of Clinical Immunology, 19(2):87-97 (1999).
Villa, A. et al., Partial V(D)J recombination activity leads to Omenn syndrome, Cell 93(5): 885-96 (1998).
Viney, J.L. et al., Generation of Monoclonal Antibodies Against a Human T Cell Receptor β chain Expressed in Transgenic Mice, Hybridoma, 11(6):701-714 (1992).
Vitiello, A. et al., Analysis of the HLA-restricted Influenza-specific Cytotoxic T Lymphocyte Response in Transgenic Mice Carrying a Chimeric Human-Mouse Class I Major Histocompatability Complex, Journal of Experimental Medicine, 173(4):1007-1015 (1991).
Vollmer, J. et al., Antigen contacts by Ni-reactive TCR: typical αβ chain cooperation versus a chain-dominated specificity, International Immunology, 12(12):1723-1731 (2000).
Vugmeyster, Y. et al., Major histocompatibility complex (MHC) class I KbDb-1-deficient mice possess functional CD8+ T cells and natural killer cells, Proceedings of the National Academy of the Sciences of the U.S.A. 95:12492-12497 (1998).
Wagner, N. et al., Ligation of MHC class I and class II molecules can lead to heterologous desensitization of signal transduction pathways that regulate homotypic adhesion in human lymphocytes, Journal of Immunology, 152(11):5275-5287 (1994).
Wagner, S.D. et al., Antibodies generated from human immunoglobulin miniloci in transgenic mice, Nucleic Acids Research, 22(8):1389-1393 (1994).
Wagner, S.D. et al., The diversity of antigen-specific monoclonal antibodies from transgenic mice bearing human immunoglobulin gene miniloci, European Journal of Immunology, 24(11):2672-2681 (1994).
Wang and Reinherz, Structural Basis of T Cell Recognition of Peptides Bound to MHC Molecules, Molecular Immunology, 38:1039-1049 (2001).
Wei, S.et al., Repertoire and Organization of Human T-Cell Receptor α Region Variable Genes, Short Communication, Genomics, 38:442-445 (1996).
Willcox, B. et al., Crystal structure of HLA-A2 bound to LIR-1, a host of viral major histocompatibility complex receptor, Nature Immunolology, 4:913-919 (2003).
Wong, F.S. et al., What can the HLA transgenic mouse tell us about autoimmune diabetes?, Diabetologia, 47(9):1476-1487 (2004).
Woodle, E.S. et al., Anti-Human Class I MHC Antibodies Induce Apoptosis by a Pathway That Is Distinct from the Fas Antigen-Meidated Pathway, Journal of Immunology, 158:2156-2164 (1997).
Woods, A. et al., Human Major Histocompatibility Complex Class II-Restricted T Cell Responses in Transgenic Mice, Journal of Experimental Medicine, 180:173-181 (1994).
Wooldridge, L. et al., Major histocompatibility complex class I molecules with super-enhanced CD8 binding properties bypass the requirement for cognate TCR recognition and non-specifically activate cytotoxic T lymphocytes, Journal of Immunology, 184(7): 3357-3366 (2010).
Written Opinion for PCT/US2012/062029, 6 pages (Apr. 29, 2014).
Written Opinion for PCT/US2012/062042, 6 pages (Apr. 29, 2014).
Written Opinion for PCT/US2014/017387, 7 pages (Jun. 2, 2014).
Written Opinion for PCT/US2014/017395, 4 pages (Feb. 6, 2014).
Written Opinion for PCT/US2014/023068, 8 pages (Jul. 24, 2014).
Written Opinion for PCT/US2014/023076, 8 pages (Jul. 18, 2014).
Wu et al., Dimeric association and segmental variability in the structure of human CD4, Nature, 387:527 (1997).
Yamamoto, K. et al., Functional Interaction between Human Histocompatibility Leukocyte Antigen (HLA) Class II and Mouse CD4 Molecule in Antigen Recognition by T Cells in HLA-DR and DQ Transgenic Mice, Journal of Experimental Medicine, 180:165-171 (1994).
Yoshikai, Y. et al., Organization and sequences of the variable, joining and constant region genes of the human T-cell receptor alpha-chain, Nature 316(6031):837-40 (1985).

(56) References Cited

OTHER PUBLICATIONS

Zamoyska, CD4 and CD8: modulators of T cell receptor recognition of antigen and of immune responses?, Current Opinion Immunology, 10:82-87 (1998).
Zijlstra, M. et al., B2-Microglobulin deficient mice lack CD4-8+ cytolytic T cells, Nature, 344:742-746 (1990).
Zumla, A. et al., Co-expression of human T cell receptor chains with mouse CD3 on the cell surface of a mouse T cell hybridoma, Journal of Immunology Methods., 149(1):69-76 (1992).
Zumla, A. et al., Use of a murine T-cell hybridoma expressing human T-cell receptor alpha-and betagene products as a tool for the production of human T-cell receptor-specific monoclonal antibodies, Human Immunology, 35(3):141-8 (1992).
Rohrlich et al. (2003) "HLA-B*0702 transgenic, H-2KbDb doubleknockout mice: phenotypical and functional characterization in response to influenza virus," International Immunology, 15(6):765-772.
Abarrategui and Krangel (2006) "Regulation of T cell receptor alpha gene recombination by transcription," Nat. Immunol., 7:1109-1115 and Corrigendum.
De Bakker et al. (2006) "A high-resolution HLA and SNP haplotype map for disease association studies in the extended human MHC," Nature Genet. Online Supplement, 33 pages.
Duke (1989) "Self Recognition by T Cell," J. Exp. Med. 170:59-71.
Fukui et al. (1993) "T-cell repertoire in a stain of transgenic C57BL/6 mice with the HLA-DRA gene on the X-chromosome," Immunogenetics, 37:3, 204-211.
Kievits et al. (1987) "HLA-restricted recognition of viral antigens in HLA transgenic mice," Nature 329:447-449.
Koller and Orr (1985) "Cloning and complete sequence of an HLA-A2 gene: Analysis of two HLA-A Alleles at the nucleotide Level" J. Immunol. 134(4):2727-2733.
Pascolo, et al. (2005) "HLA class I transgenic mice: development, utilisation and improvement," Expert Opinion Biol. Ther., 5(7):919-938.
Scheer et al. (2013) "Generation and utility of genetically humanized mouse models." Drug Discovery Today, 18 (23/24):1200-1211.
Sherman et al. (1992) "Selecting T Cell Receptors with High Affinity for Self-MHC by Decreasing the Contribution of CD8," Science, 258:815-818.
Theobald et al. (1995) "Targeting p53 as a general tumor antigen," PNAS, 92:11993-11997.
Statement of Relatedness under MPEP 2001.06 dated Sep. 14, 2015.
Reipert et al. (2009) "Opportunities and limitations of mouse models humanized for HLA class II antigens," Thrombosis and Haemostasis, 7(Suppl. 1):92-97.
Wen et al. (1998) "Induction of Insulitis by Glutamic Acid Decarboxylase Peptide-specific and Hla-DQ8-restricted CD4+ T Cells from Human DQ Transgenic Mice," J. Clin. Invest., 102(5):947-957.
Non-Final Office Action with Respect to U.S. Appl. No. 14/185,316, Mailed Dec. 17, 2015.

* cited by examiner

SEQUENCE LISTING

```
<160> NUMBER OF SEQ ID NOS: 59

<210> SEQ ID NO 1
<211> LENGTH: 202
<212> TYPE: DNA
<213> ORGANISM: Artificial
<220> FEATURE:
<223> OTHER INFORMATION: synthetic

<400> SEQUENCE: 1
aggggaaacc cgcaaaggat gggacatagg gagacagctg ttaacatctg aaacatgacc      60
ttcttttctg tgcagcacaa ctcctagctg tcactcaagg gaagaaagtg gtgctgggca     120
aaaaagggga tacagtggaa ctgacctgta cagcttccca gaagaagagc atacaattcc     180
actggaaaaa ctccaaccag at                                              202

<210> SEQ ID NO 2
<211> LENGTH: 240
<212> TYPE: DNA
<213> ORGANISM: Artificial
<220> FEATURE:
<223> OTHER INFORMATION: Synthetic

<400> SEQUENCE: 2
ctggtcacct ggatgaagtg agggagggcc ctctgggttt ggggctggtt ttgaactgag      60
```

| | | |
|---|---|---|
| acatccatga gccagcctgg ggctggcttc actgaagatc atctatgtcg ggtgcggaga | | 120 |
| aagaggtaat gaaatggcac atgctatgta caaactctat tgctgagcag cacccagtcc | | 180 |
| tgagctggct ctgaattgag ggtgaaattc acacattctc ccccaacatc tataatctgg | | 240 |

<210> SEQ ID NO 3
<211> LENGTH: 18263
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2957)..(2957)
<223> OTHER INFORMATION: n is a, c, g, or t
<220> FEATURE:
<221> NAME/KEY: misc_feature
<222> LOCATION: (3193)..(3193)
<223> OTHER INFORMATION: n is a, c, g, or t

<400> SEQUENCE: 3

| | | |
|---|---|---|
| aagaaagtgg tgctgggcaa aaaggggat acagtggaac tgacctgtac agcttcccag | | 60 |
| aagaagagca tacaattcca ctggaaaaac tccaaccaga taaagattct gggaaatcag | | 120 |
| ggctccttct taactaaagg tagggttgcc tggctcccca tccagggagg aaaacacact | | 180 |
| atggagtgaa agcctttggt gtctgagatc tggtcttagt taaactctgg gatcggcgcg | | 240 |
| ccgaattcct gcagcccggg ctcgagataa cttcgtataa tgtatgctat acgaagttat | | 300 |
| atgcatccgg gtaggggagg cgcttttccc aaggcagtct ggagcatgcg ctttagcagc | | 360 |
| cccgctgggc acttggcgct acacaagtgg cctctggcct cgcacacatt ccacatccac | | 420 |
| cggtaggcgc caaccggctc cgttctttgg tggccccttc gcgccacctt ctactcctcc | | 480 |
| cctagtcagg aagttccccc ccgccccgca gctcgcgtcg tgcaggacgt gacaaatgga | | 540 |
| agtagcacgt ctcactagtc tcgtgcagat ggacagcacc gctgagcaat ggaagcgggt | | 600 |
| aggcctttgg ggcagcggcc aatagcagct ttgctcctc gctttctggg ctcagaggct | | 660 |
| gggaagggt gggtccgggg gcgggctcag gggcgggctc aggggcgggg cgggcgcccg | | 720 |
| aaggtcctcc ggaggcccgg cattctgcac gcttcaaaag cgcacgtctg ccgcgctgtt | | 780 |
| ctcctcttcc tcatctccgg gcctttcgac ctgcagccaa ttgttgacaa ttaatcatcg | | 840 |
| gcatagtata tcggcatagt ataatacgac aaggtgagga actaaaccat gggatcggcc | | 900 |
| attgaacaag atggattgca cgcaggttct ccggccgctt gggtggagag gctattcggc | | 960 |
| tatgactggg cacaacagac aatcggctgc tctgatgccg ccgtgttccg gctgtcagcg | | 1020 |
| caggggcgcc cggttctttt tgtcaagacc gacctgtccg gtgccctgaa tgaactgcag | | 1080 |
| gacgaggcag cgcggctatc gtggctggcc acgacgggcg ttccttgcgc agctgtgctc | | 1140 |
| gacgttgtca ctgaagcggg aagggactgg ctgctattgg gcgaagtgcc ggggcaggat | | 1200 |
| ctcctgtcat ctcaccttgc tcctgccgag aaagtatcca tcatggctga tgcaatgcgg | | 1260 |
| cggctgcata cgcttgatcc ggctacctgc ccattcgacc accaagcgaa acatcgcatc | | 1320 |
| gagcgagcac gtactcggat ggaagccggt cttgtcgatc aggatgatct ggacgaagag | | 1380 |
| catcaggggc tcgcgccagc cgaactgttc gccaggctca aggcgcgcat gcccgacggc | | 1440 |
| gatgatctcg tcgtgaccca tggcgatgcc tgcttgccga atatcatggt ggaaaatggc | | 1500 |
| cgcttttctg gattcatcga ctgtggccgg ctgggtgtgg cggaccgcta tcaggacata | | 1560 |
| gcgttggcta cccgtgatat tgctgaagag cttggcggcg aatgggctga ccgcttcctc | | 1620 |
| gtgctttacg gtatcgccgc tcccgattcg cagcgcatcg ccttctatcg ccttcttgac | | 1680 |

-continued

```
gagttcttct gaggggatcc gctgtaagtc tgcagaaatt gatgatctat taaacaataa    1740
agatgtccac taaaatggaa gttttttcctg tcatactttg ttaagaaggg tgagaacaga   1800
gtacctacat tttgaatgga aggattggag ctacgggggt gggggtgggg tgggattaga    1860
taaatgcctg ctctttactg aaggctcttt actattgctt tatgataatg tttcatagtt    1920
ggatatcata atttaaacaa gcaaaaccaa attaagggcc agctcattcc tcccactcat    1980
gatctataga tctatagatc tctcgtggga tcattgtttt tctcttgatt cccactttgt    2040
ggttctaagt actgtggttt ccaaatgtgt cagtttcata gcctgaagaa cgagatcagc    2100
agcctctgtt ccacatacac ttcattctca gtattgtttt gccaagttct aattccatca    2160
gacctcgacc tgcagcccta gataacttcg tataatgtat gctatacgaa gttatcctag    2220
gccagagggc ttgggttgac agaaactcag tggcattctt atccagagtt tctctacacc    2280
aactgctggt ggcccaggga aggtggtat gtgaatttca atattttaat atttaatatt     2340
catgaactta ttttagtgag ttttagaaca atcactatca cttaaaaccc gtgatttctt    2400
gagtattgtt gctacagacc tatgtagata atactttgca cagtgactca tatgtataat    2460
cctagcactg tgggaggctg aggccggagg attgcttgag tccaggagtt caagaccagc    2520
ctgaacaaca tagtgagact ctgtctctat gaaaaaaaat atatatatat ttttttttgga   2580 gacaaggtct agttctatca cccaggctcc agtgcagtgg tgtgatctcg gctcactgca    2640
atctccacct cccaggctca agtcatcatc ccacctcagc ctcccaagta gctgggacta    2700
caggcatgca ccaccatgcc aggctaattt ttgtattttt tatagagaca gggtttcacc    2760
atgttggcca ggctggtctc gaactcatga gctcaagtga tccactcacc ttggcctctc    2820
agagtgctgg aattacaggt gtgtgtcact atgcctagcc aaaaaaaatt ttttttaatta   2880 aaaaaaaaaa ggccggctgt agtggctcac acctgtaatc cagaactttg ggagtttgag    2940
gtgggcagat caccggnggt caggagttca agaccagtct ggccaacatg gtgaaacccg    3000
gtctctacta aaaatacaaa aattagccag gtgtgggggt gcagtcctgt acttccagct    3060
actcaggagg ctgaggcagg agactcgctt gaacctggga ggcaaaggct gcagtgagct    3120
gagattgcac cactgcactc cagcctgggt gacagagcaa gacttcatct caaaaaaaaa    3180
aaaaaagctg canatttatt attattatta ttagtttatt tatttatttt tttgagacag    3240
agtctcgttc tgtcgcccag gctggagtgc ggtggcgtga tcttggctca ttgcaacctc    3300
cacctcccgg gttcaagtga ttctcctgcc tcagcctccc gagtagctgg gactacaggc    3360
gtatgccacc atgcctggct aatttttttgt acttttagta gagacagagt ttcacggtgt    3420
tagccaggct ggtcttgatc tcctgacctc gtgatttacc ctccttggcc tcccaaagtg    3480
ctgggattac aggcgtgagt cactgtgccc ggcccagaat catttttttc actttttttt    3540
tttttgaggc aaactctcga tctgttgccc aggctggagt gcagtgggca tgatcttggc    3600
tcactgcaag ctctgcctcc caggttcaag caattctcct gcctcagcct cctgagtagc    3660
tgggactaca ggcgtgtgcc accatgcccg gctaatttgc gtatttttag tagagaccgg    3720
ttttcatcat attggccagg ctggtcttga actcctgacc tcaagtgatt ctcccacctt    3780
agcctcccaa agtgctggga ttacaggcat gagctactgc acttggcctt ttctcctggt    3840
tttaaaacta ttatatgctc attacaaaat atttggtcaa tgaagaaaag aatatggaag    3900
aaaatcaaat gcatgcatac ttctatcact cagagatatc ctctgctaac attttgattg    3960
attttcttcc aatcttttttt tttttttttc ttttgagac agggtctcac tctgctgccc    4020
```

```
aggctggagt acagtggcat gaccacaaca catcacagcc tcaagtgatc ttcccacttc    4080
agccttccca gtagctggga ctacaggtgc acgccaccat gttcacctaa ttttttactt    4140
tttgtagaga tgagacttca ccatgttgct caggctggtc ttgaattcct aggctcaagt    4200
gatcttcccg ctttggcctc ccaaagtgct gggattatag gtatgagcca ctgcatgtgg    4260
cctatttcct tccactgttg ttcggcgtgg agaatattat atacataatt acgtaaatga    4320
tatcatactg tatataccct ttttcctact ccttccttaa gttatatcat aatgagacta    4380
ccaattatta gactttttt cttttttttg agacggagtc tcggtctgtc acctaggctg    4440
gagtgcaatg gcgcgatctc agctcgctgc aacctctgcc tcccaggttc aagcaattct    4500
gcctcagcct cccgagtagc tgggactaca gacacgtgcc accatgccca gctaactttt    4560
ttattttttt attagagaca gggttccacc atgctagcag gatggtctca atctctcgac    4620
tcgtgatca gcccggcttg gcctcccaaa gtgctgggag tacaggtgtg agccaccgca    4680
ctcggcctag actaactatt taaagtaatc tggcaatgtt taacgaatac aaaactctaa    4740
aaccctggga cctaataata gctatttgg aaagtctact tgacagaaat aaaattgtga    4800
atattcttt tgttgttt tttgagacag agtctcattt ggacgcctag gctggagtgc    4860
agtggcatga tctcggctaa ctgcaacctc cacctcctgg gttcaagtga ttctcctgcc    4920
tcagcctcct gagcagctgg gattacaggt gtgcaccacc atgtctggct aattttttgca    4980
ttttagtag atggggtttc accatgttga ccagggtggt ctggaacttc tacccctcaag    5040
tgatctaccc accttggcct cccaaagtgc tgggattaca ggtgtgagcc accacgcctg    5100
accagtgaac acttaataat atctatggaa aggtgttatt ataagaattg cttgtggggc    5160
cgggcgtggt ggctcacgcc tgtaatccca gcactttggg aggctgtggc aggcggatca    5220
cgaggtcagg agatcaagat catcctggct aacacggtga acccgtct ctactaaaaa    5280
taccaaaaaa ttagccaggc gtggtggcgg gcacttgtaa tcccagctat ccaggaggct    5340
gaggcaggag aattgcgtga acccaggagg cggaggtcgc agtgagctga accgtgcca    5400
ttgcactcca gcctgagtga cagagtgaga ctccatcaca aaaataaat aaataaataa    5460
ataaaatata aataagtaaa taaaggtcag gagtggtggc tcacgcctgt aatcccagca    5520
ctttgggagg ccgaggtgga cagatcatga ggtcatgaga tcaagaccat cctggctaac    5580
acagtgaaac cctgcctcta ctaaaaatac aaaaagtcat ccaggtgtgg tggcacacac    5640
ctatagtccc agctacttgg gaggctgagg caggagaatc acttgaaccc aggaggcaga    5700
ggttgcagtg agctgagatc gcgccactac actccagcct aggcgacaga gcaagactct    5760
gtctcaaaat aaataaataa ataaataaat aaataaataa ataaataaaa taaaaagcac    5820
acacacacac acacacacac acacacaatg caaaagaccc accctactac aactaacatt    5880
atatttaatg gtgaaaaact gaattctttc tccctaagtg caggaataag acaaagatgt    5940
ctgctcttac tactcttatt caacataata ctgcaatccc ttgccagtgc aataaggcaa    6000
gaaaaatgaa ataaaaggaa aactgatcag aaagaaagaa ataaaactgt tcctatttgt    6060
ggatgacatg attcataga aaatctcaaa gaatctgtaa gaaacttctt agaattaata    6120
aatgaattca tcaaggttgc agaatataag ataaacataa aaaatctatt gtatttctat    6180
atattagcaa ggaacatgtg tacacagaaa ttaaaactac aataccattt ataattgctc    6240
aaaaaggcca ggcatggtgg ctcacacctg taattcctgc actttgggag gccaaggtgg    6300
gaagattgct taagcccagg agttcaagac cagcccgggc aacatagtga gaccttgtct    6360
ctacaaaaag taaaaaatta gctgagcatg gccgggtgca gtggctcact cctgtaaccc    6420
```

```
caacactttg ggaggctgag gcgggcggat catgaggtca ggagatcgag accatcctgg    6480
ctaacacggt gaaaccctgt ctctactaaa aacacaaaaa attagctgga tgtggtggca    6540
ggcgcctgta gacccagcta ctcgggaagc tgaggcagga gaatggcgtg aacctgggag    6600
gcggagcttg cagtgagctg agattgtgcc actgcactcc agcctgggtg acacagtgag    6660
actacgtctc aaaaaaaaa aaaaaaaaat tagctgagca ttatggtgta tgcctgtagt    6720
cccagctact ggggaggctg aggtgggagg attgcttgag ccctaggagg gcaaggctgc    6780
agtgagccat gatcacacca ctgctttcca gcctcggtag gagagcaaga ccctatctca    6840
aaaaaaaaaa aaaaaaaaaa agaaaagaaa agaaagaaa agaaaagaa agagagaaag    6900 aaatacttag gtgtaaatct aaaaaacatg cgtagggcca ggtgcagtgg ctcatgcctg    6960
taatcccagc actttgggaa gttgaggctg gcggatcact tgaagtcggg agtttgagac    7020
cagcctggcc aacatggtga aaccccgtct ctactaaaaa tgcaaaaatt aggcaggtgt    7080
tgtggcgcat gcctgatccc agctactttg gaggctgagg caggaaatt gcttcaaccc    7140 gggaggcaga ggttgcagtg agccaagact gttccactgc actccagcct gggcaacaga    7200
gtaagagtct gtctcccgaa aaaaaaaaaa agaaaaaga aagcattgaa ttgtatgcta    7260
aaaactacac gatgctgatt aagaagtca agaagatct aaatatatgg agagacatgc    7320
tgtactcatg gattgatgga ttggaagact caacataaga cagatatcaa ttttccccaa    7380
attaatatac aagtttaatc caattcctat aaaaatacca gcaagatttt ttgtagatat    7440
aaacaagttg gccaggtgta gtggcttaca cctgtaatcc tagcactttg ggaggctgag    7500
gtgggaagat cgcttgagcc caggtgttca cgactgcagt gagctatgat tgtgtcactg    7560
cattccagct ggcactccag cctaagtgac aaagggagac cctgtctcaa aaacaaaaac    7620
aaaaccaaaa taattttgct ctgcaaaatc cctattaaga agaagaaaag aggctgggca    7680
cagtggctca ccgctgtaat cccagcacgt tgggaggctg aggcaggctg atcacttcag    7740
cccagaagtt tgagatcagc ctgggcaaca tgaggaaacc ccgtctctac caaaaaaaaa    7800
aaaaggtaca tacacacaca cacacacaca cacacacata cacaagtata tacacatata    7860
tatacacata caggtgaata gatgtatata catctattta ttgtgaatat acatctatac    7920
acacacgtgt gtgtacacat atatttaaaa tttattttta tttatttatt tattttgag    7980 acagagtctt gctctgtcac ccaggctggg tgcacctgta ttcccaacga cacaggaggc    8040
tgaggtggga gaatcactga gccagggagg cagaggttgc agtgagccaa gatgttgcct    8100
ggttgcctgg gcaacagagc gagaccctat atcaaaaaag aagaataata agaaaagaca    8160
gtttacagaa tataagaaaa tatattcaca atccacatac ttagcaaagg actggtatct    8220
agaatatgat aaacaactct caaaactcaa aaccaaaaaa atgaacaatt caattagaaa    8280
acaggccgaa aaggacatac agttggcaaa taagcacatg aaaagttgtt caacatcatt    8340
aatcattagg gatatgtaca ttaaaaccac aataggctat cactaaacct atcagaatgg    8400
ctaaatacaa aattggaaca ccaccaaatg ctgatgagga tgtggagaaa ctgggtcatt    8460
cttccaatat tggtgggagg ctaaaatggc aaagccactc tggaaaacag tttgatagtt    8520
tcttataaaa caaacatgc ggccgggcgc ggtagctcac gcctgtaatc ccagcacttt    8580 ggggaggccga ggcgggtgga tcacgaggtc aggagatcga gaccatcctg gctaacacgg    8640
tgaaaccctg tctctactaa aaatacaaaa attagccgg gcgtggtggc gggcgcctgt    8700
agtcccagct actcgggagg ctgaggcagg agaatggtgt gaacccggga ggcggagctt    8760
```

```
gcagtgagcc gagatcgcgc cattgcactc caacctggga gacggaggga gactccgtct   8820
caaaaaaaca aaaacaaaca aacaaaaaac atgcaacaat ccagcaatat tgcacccta    8880
ggcatttatc ctagagcaat gaagacttat gcccacacaa aaagctgcac acaaatgttc   8940
atagcagctt tattcatggt agccaacaat tagaaacaat ctagatgtcc ttcaactggt   9000
gaatgattac atccatacca cgaaatactt ttcagcaata aaaggatga atcatagtac    9060
acaccacaac ctggatgaat ctccagggaa ttatgctgag tgaaaaaaag ccaatctcaa   9120
aaggtaatat actgtattaa tccatttata taacattctt aaaataacta attatagaaa   9180
tggagaacag atgagtgatt gccaggggtt aaggggctca gggatgggga ggggaagggg   9240
tatggctaca aaaagcaaca accttatggc gccggaaatg ttctgtattc tgattgtgtc   9300
aatgtgagca tactggttga gatatagtgc tacagttttg caagttatta ccatcagagt   9360
aaactggata gagggcacat aggatttctc tgtattactt cttacaactg caagtgaatc   9420
tacaattatc tcaaaataat aagtttagtt taatgctagg cgtggtggct cacatctgta   9480
atctcagctc tttgggaggc tgagacgggt ggatggcttg agtccaggag ttcgagacca   9540
gcctggccaa catggcaaaa ccggtctcta ctaaaaatac aaaaattagc tgggcgtggt   9600
ggcaagtgcc tgtagtccca gctactcggg aggctgaggc aggagaattg cttgaacccg   9660
ggaggtggag gttgcagtga gccgagatca cgccactaca ctgtagcttg gcgacagag    9720
tgaggctctt tctcaaaaaa aaaaaaaaa aaaaaaagc aggcaggcag ggccaggaaa     9780
gcgtataatt tttgtagttc aaatgactaa cctaaaaagt gaagattggc caggcgcagt   9840
ggctcacgcc tgtaatccca gcactttggg aggccaaggc gggtggatca cgaggtcagg   9900
agattgagcc actctggcta acacagtgaa accccgtctc tactaaaata caaaaaatta   9960
gctgggcgtg gtggcacccg cctgtagttg cagctacttg ggaggctgag gcaggagaat  10020
cacttgaacc caggaggcga gttgcagcg agccgagatc acactactgc actccagcct  10080
gggtgacaaa gtgagattct gtctcaaaaa aaaaaaaaa aaaaaaaaa aaaaaagtg     10140
aagtttacct tttttttaa atttttcttc ttttccttcc ctactttgtg agataatttt  10200
cttcttttta aaagccaag agcttacttc tgtaagtaaa gattatctta agacaactta   10260
gaaatgtata ttattagtat tttctatttc attgtaagtt atttgtaaat attggttttg  10320
gtgctaacct agaattccat caaattaatt gtccctaat atatggccat tatcattttg   10380
tctaacattg tatcctatta acaatgctgt aagtattatt tttgtagcta aattatggtt  10440
tgcattttaa aattattgtt ttaaggataa agttccagaa atgaaattaa ggatatgaac  10500
tttttgagca catcttgtca gcactgagta gtattattta aaacttttgg gggggcaat   10560
tttataattg aaaaatatat cattgtttta atttgcattt ctttcactgc ctatgagatt  10620
aaaacaatgc actactttcc aaaaattctt aagtcttttg tgttgatgct tttgttctgt  10680
ttctatggat ctcatcttcc ttcagaacag ctcccctttcc caacttcctg atttctaaca  10740
ataacagtat caccctcctt gttctcccaa tttctgaaac acagagtcat gttttttct   10800
ctgcttcaat ccctggtttc ctatcgtcat caattatgac cttccttgc tttgaaagtg   10860
ttttgggccg gcatgatgt ctgccaccta ttgtaatcct agcactttgg gaggctgagg   10920
cggctggatg acttgacctg aggatttcga gaccagcctg ggcaacaggg cgaaacctcg   10980
tctctacaaa aaatacaaaa gttagtcggg agtggtggca catgcttgta gtcccagtta  11040
cttgggggggc tgaggtggca ggatctcttg agcccacgag gtagatgttg cagtgagccg  11100
tgattgcgcc actgcacccc agcctaggtg acagagtgag accctgtctc aaaaaaaaa   11160
```

```
aaatgttcta gtttcttcct cttctttgtt cccatgggaa tgccaccatc accagccaag   11220
gctcacatac ctcccacctg gattacagtg agcttccagg taatttggtc tgctactagt   11280
ctcgcctact tggatttccc ttccccctgc tgcagcattg ccttccaaag ccatgctttg   11340
cacatgccac atcctagccc attagactaa gcctagaagc ctctgcagga cgttcaccct   11400
ctcagcgcca ctgctcagtt tcccagtgga aacctctgca cccaggaggt ttccccacag   11460
cttgcctgtg ctgcctctct ggagcttttc tcccttcctg taatgtcctt gctgctcccc   11520
gtctctagtc cattgcctat acctcttttt tttttttttt ttgagatgga gtctctctct   11580
ctcatccagg ctgagtgca gtggcgcgat ctcggctcac tgcaaccttt gtctcctggg   11640
ttcaagggat tctcctgcct cagcctcccg agtaactggg attacaggcg tgcaccacca   11700
ttcctggcta attttgtat ttttagtaaa gactgggttt caccatgttg gccaggctgg   11760
tcttgaactc ctgccctcag gtgatccacc tgcctcggcc tcccagagtg ctgggattac   11820
aggcgtgagc caccgcacct gccacaggcc catacctctt ttaagtcttc attcaatacc   11880
agttgtccca tgaatttgtc ccagactcac tcatatgctt agacctttca tattatcttg   11940
ccatagcttt tcaaagtat gggacagcat ggacaagcag gccatggttt tcttttgaag   12000
agaagcaagg aggcagagtt attttaggag gagggttata catttcattt tgaaccaatt   12060
gcgtttgggg tgatggcagg atattaacat aaacttattt cttggaccat ggaaatgtg   12120 tgcctagaac tgaggagaga ggtcagggct ggcagtaaca acttggccac aatctgcaga   12180
gctgactggg gatgaggtgg aatttagaat gtctgtagaa acggggaaga gaaccaaaga   12240
cagagtctgg gacaacacct aaatgtagat gtcagagcaa gagttcaaga cgaagaaaaa   12300
cgaatcatac ttagaaatgg aggggaggaa caaagaggc ggagcaaagt ggggcagaac   12360
cagagtaggc cacgctttta agaagtttgg taaaggaact gtgaaaggaa tgtagttgaa   12420
tttcagggta agctggggaa ttaaagcagt gtgtagatcc agggcaaaca gcaagtaggg   12480
caggaaccac tgaaggaaca aataaagggg gaggttgggt ccaggttgtc ttgagtaggg   12540 aagtttttt aaaaagtgtg aaactgaagg tgtggggtgg attgggtgcc tgccgtgctc   12600
tgaggaagct tggggcaact gtgtgctgag gctgtgaggt tgtctggaag gggctcctgg   12660
acagtaagag ctgagcagtg gggaagagga ctgtgtggtc tggaagagga gagaaggag   12720 agtgagtgac tgaactggta tccaggctcc cacaccaagg cagaaagagg gagaggacct   12780
gggcatctca gggaggcaga ggcagtacca agcagggtga gaggctttag tcttagccac   12840 ctttgccca ttcctccaaa tatacattct aagtaaaaac aaaacaaaac agaactgttt   12900
gctatgtaaa tttagcttct aaagccctgt tctacagaga ttttggagct tccactgcac   12960
ccagaaaatg cacagctaaa gagaaaactt cccttggtga tggttattag attttacaag   13020
aagaggccaa aggagacaca tacttatgcc agaagaactt tccagagata gcattgcata   13080
gcgaaatagc ctgaattatt tttatttttt aaaacatttt ttcttttctt ttttctttc   13140 ttttctttt tttttttttt tttttgagac agagtctcac tctgtcaccc aggctggagt   13200
gcagtggcgt gatcttggct cactgcaatc tccacctccc gggttcaagc cattctcctc   13260
cctcagcctc ccaagtagct gggattacag gcatgcgtca ctatgctctg gctaattttt   13320 ttttctttt ttttttggt attttagta gagatggggt ttcaccatgt tggccaggct   13380
ggtcttgaac tctgacctc aagtgatcca ccgccttggc ctcccaaagt gctgggattt   13440
caggcgtgag ccaccgcacc cggccaaaaa tttcttttct ttaagatgag gcctcactct   13500
```

-continued

```
gttgcccagg ctggagtgca gtgttacaat catagctcac tgtaactttg aactcctggg   13560
ctcaagtgat cctcctgctt cagcctctca agtagctggg attacaggca tgtgccacca   13620
cacccagcta atttttttta aaataatttt ttttagagac gagggtctcg attggctgcc   13680
taggttggtc ccagactcct gacgggctgc attttaatcc tagctccacc acttacggga   13740
gtcaaaattc aaaagataga aaagggcata taggctgggt gcagtggctc acacctgcaa   13800
tcccagcaat ttgggaggct gaggtgggcg ggttgcttga ggtcaggagt tcgagatcag   13860
cctgggcaac atggcaaaac ttgtatctac taaaaataca aaaattagcc agatgtggtg   13920
gtgtacacct gtaatcccag ctactccgaa ggctgaggca agagaatccc ttgaactcag   13980
gaggcagagg ttacaatgag cagagatcga acactcgact ccataaaaac aaacaaacaa   14040
aaaaagaaag caggctgggt gtggtggctc acgcctgtaa ccccagcact cgggaggcc    14100
aaggcgagcg gatcacctga ggttgggcat tcgagaccag cctgaccaac aaggagaaac   14160
cctgtctcta ctgaaaatac aaaattagcc gggcttggtt gcgcatgcct gtaatctcag   14220
ctactcggga ggcagaggca agataattgc ttgaacccgg gaggcggagg ttgcggtgag   14280
ccaagatcat gccattgcac tccaacctgg gcaacaatag cgaaactcca tctcaaaaaa   14340
aaaaaagcaa agggcatata gtgaaaagct tcttcctac acatgagtat tcacttcctc    14400
ttcctagagg caaccaaggt tattttttgtg tgtgtgtgtg tgtgtgtgtg tgtgtgtgtg   14460
tgttttggga cagtctcact ctctcaccaa ggctggaatg cagtggtgcg atctcactgc   14520
aaactctgcc tcccagtctc aagcgatctt gtgcctcagc ctcccagttt ttttttcttt   14580
taaatggggt ctcattctgt cgcccagggt ggagtgcagt ggcatgatca tagctcactg   14640
cagcctcgac ctcctgggtc aggttatcct cccacctcag cctccggcat agctggggct   14700
actggcatgc accaccacac tcagttaatt tttttctttt tttgagacag agtctcactc   14760
tgtcacctag actggagtgc agtggtgcca tctcatttgt ttcactgcaa cctttgactt   14820
ctgggctcaa gtgattctcc cacctcagcc tccaaggcg gctaattaaa aaaaattttt    14880
tttttttttt ttttagagat ggggtttcgc catgttgccc aggctgatct cgaactcctg   14940
ggcacaaaca atcttccac ctcgatcttt caaagagctg ggatgagaga tttccaccat    15000
gcctggcctc attttctttt ttaattttttt tttagacatt atagctcttt ttaatggcct   15060
cattttctta tgtttaattc gagaattatt cttttcatat acaaagaata tattttctcc   15120
accttttaaaa acaaatagta gactgtttaa catctcgctt tattcagtta gtgatgtttc   15180
ttagatacgg gtccaaatta gtacacaaag cacttcctca ttcctctctt acggctgcat   15240
agcagtccac tgaatgggtg agctatgatc tatttaacct attctttatt gatggacatt   15300
tggttttgta tatacatttg taattctgta tagattacaa atcaccatcc aaagaaattg   15360
tactggttta ttctcctaca atgtgtgaga gttgggtaat tacttaatct caatatgtga   15420
gagtttaggc agttacctaa tctctctgag tctcagtttc tctatctgca aaataaacaa   15480
aacagtgttg acagtatcta tttctcggaa ttattgtgga gattactgag atgatgcctg   15540
taaagtattt ggcatgtagg agttggtgct ctccaaataa ggatatgatt ttatttgtat   15600
ttgtgagcta ctgtcccagc caggtaaatg gatatgatga gacctccttg ccagaccggg   15660
tttctctgat tagaacgagg agcagatgtt gcaggaaatt agcaactgat atcagaagag   15720
ccgtgggcat tctcttgcca gaggtgccct gtctccaggg cgcctcagtc ccccccata    15780
tgtcttctgc tcccaggtcc atccaagctg aatgatcgcg ctgactcaag aagaagcctt   15840
tgggaccaag gaaactttcc cctgatcatc aagaatctta agatagaaga ctcagatact   15900
```

```
tacatctgtg aagtggagga ccagaaggag gaggtgcaat tgctagtgtt cggatgtgag   15960
tggggcaggt ggggatgagg atacctcctg cctggttccc ttccccacta ctcccacccc   16020
tgcaccaaat ccagcctgag ctggtgatac cgcagcagcc ccaagaggac caggctgtca   16080
aactggcctc caaatgtctt aaaacccttc ttgatcaggt gagggatgct ggtgggcgga   16140
ggagggaaga ggccttggga aaaggaaaga aagggaagg aggcaaggga aggagggaga    16200
gagactgggg aagagaggat gagggagag gaggaaagaa gagagagagg aggggagagg    16260
gaaaccctat cttggctggg ggtgcgcagc tgggtgctgg gaggaaggag atgttgggac   16320
ggcgataatg gagagatgtt gttggtttcc tgttgtctgc ccttctcctt ggggatggta   16380
tgtgtgtgac acagctggcc tttccctcca cagtgactgc caactctgac acccacctgc   16440
ttcaggggca gagcctgacc ctgaccttgg agagccccc tggtagtagc ccctcagtgc    16500
aatgtaggag tccaaggggt aaaaacatac aggggggaa gaccctctcc gtgtctcagc    16560
tggagctcca ggatagtggc acctggacat gcactgtctt gcagaaccag aagaaggtgg   16620
agttcaaaat agacatcgtg gtgctaggta agggaagccc ctcttcgcgc agtctcctcc   16680
ctgccccagg ggctgacagc ccctccctct gctctgactg ccctgtttct ggttctggtg   16740
ctgggaggtc aggagtggag aagactaggt cccctagagc tgaggcctgt cttgaaggac   16800
tcactggggc cctcatcctc aggggctga ttggcagcca cccctcagtg tggtggacat    16860
ggagaaagga aaggctgggg aaggtaagga tgctagaggc ccgagtctcc tttggaggcc   16920
ccaaaggagg aatgtcaggg agcttacttt ctttgttgcc tcagctccac acccctacca   16980
agttggcaaa tccacttact cagggacact aacaccagta agccaaccct gatgatgttc   17040
tatgttgtac ctctggacct ctaagccagg ccactgtggg gagaccaagg tcctacccca   17100
gatcctgtcc cctgggtgct tatgtgactt aaggtagaca taaggtagtg tgccagttta   17160
gtgcatgtac gctgattgaa atcctggttc tgccacaacc atgtgacctt gggtgagtta   17220
ctaaacctct ctgcaccttg gtttcagcct ctgtgaaatg gggatgatgt taactgccat   17280
agtgactacc tcgtattaag ttgaggactg atatacgtaa ggcactgaaa atggtgcctg   17340
gcacagagta agccctagtt aagtgttcgc tgttattttg tgaagggtga tgaatacgcc   17400
tctaaggagt ggaggccaaa tggcttctgt ggtccaggaa tcctaaggac agcaaggatc   17460
ccctgtggct gggctgctct gtgatggctt ccgggaggag ggaggtggcc tgctgtagga   17520
aaatgctggg tggaagaagg gagagaaggc tggagaggta ggaaggaact gaagtatctg   17580
aagtgacaag gtgggtgtct ggactcgtcg ggtccccttc catctccctg ctgcctccac   17640
atgccaaccc cactcgtgca ccctcatctt cctatctcct cacccagggt ctctcccttc   17700
ccacctccag ctttccagaa ggcctccagc atagtctata agaaagaggg ggaacaggtg   17760
gagttctcct tcccactcgc ctttacagtt gaaaagctga cgggcagtgg cgagctgtgg   17820
tggcaggcgg agagggcttc ctcctccaag tcttggatca ccttgacct gaagaacaag    17880 gaagtgtctg taaaacgggt tacccaggac cctaagctcc agatgggcaa gaagctcccg   17940
ctccacctca ccctgcccca ggccttgcct cagtatgctg gctctggaaa cctcaccctg   18000
gcccttgaag cgaaaacagg aaagttgcat caggaagtga acctggtggt gatgagaggt   18060
gaggggccag gccagggagg ggtgggcagg ggaaggagtt ggaggggcct ggcccagggc   18120
tccctctgag gcaagccagg ccccaagagg ggatgcctag gccctggtca cctgatgaa    18180 gtgagggagg gccctctggg tttggggctg gttttgaact gagacatcca tgagccagcc   18240
```

```
tggggctggc ttcactgaag atc                                              18263
```

<210> SEQ ID NO 4
<211> LENGTH: 458
<212> TYPE: PRT
<213> ORGANISM: Artificial
<220> FEATURE:
<223> OTHER INFORMATION: Synthetic

<400> SEQUENCE: 4

Met Cys Arg Ala Ile Ser Leu Arg Arg Leu Leu Leu Leu Leu Leu Gln
1               5                   10                  15

Leu Ser Gln Leu Leu Ala Val Thr Gln Gly Lys Lys Val Val Leu Gly
            20                  25                  30

Lys Lys Gly Asp Thr Val Glu Leu Thr Cys Thr Ala Ser Gln Lys Lys
        35                  40                  45

Ser Ile Gln Phe His Trp Lys Asn Ser Asn Gln Ile Lys Ile Leu Gly
    50                  55                  60

Asn Gln Gly Ser Phe Leu Thr Lys Gly Pro Ser Lys Leu Asn Asp Arg
65                  70                  75                  80

Ala Asp Ser Arg Arg Ser Leu Trp Asp Gln Gly Asn Phe Pro Leu Ile
                85                  90                  95

Ile Lys Asn Leu Lys Ile Glu Asp Ser Asp Thr Tyr Ile Cys Glu Val
            100                 105                 110

Glu Asp Gln Lys Glu Glu Val Gln Leu Leu Val Phe Gly Leu Thr Ala
        115                 120                 125

Asn Ser Asp Thr His Leu Leu Gln Gly Gln Ser Leu Thr Leu Thr Leu
    130                 135                 140

Glu Ser Pro Pro Gly Ser Ser Pro Ser Val Gln Cys Arg Ser Pro Arg
145                 150                 155                 160

Gly Lys Asn Ile Gln Gly Gly Lys Thr Leu Ser Val Ser Gln Leu Glu
                165                 170                 175

Leu Gln Asp Ser Gly Thr Trp Thr Cys Thr Val Leu Gln Asn Gln Lys
            180                 185                 190

Lys Val Glu Phe Lys Ile Asp Ile Val Val Leu Ala Phe Gln Lys Ala
        195                 200                 205

Ser Ser Ile Val Tyr Lys Lys Glu Gly Glu Gln Val Glu Phe Ser Phe
    210                 215                 220

Pro Leu Ala Phe Thr Val Glu Lys Leu Thr Gly Ser Gly Glu Leu Trp
225                 230                 235                 240

Trp Gln Ala Glu Arg Ala Ser Ser Ser Lys Ser Trp Ile Thr Phe Asp
                245                 250                 255

Leu Lys Asn Lys Glu Val Ser Val Lys Arg Val Thr Gln Asp Pro Lys
            260                 265                 270

Leu Gln Met Gly Lys Lys Leu Pro Leu His Leu Thr Leu Pro Gln Ala
        275                 280                 285

Leu Pro Gln Tyr Ala Gly Ser Gly Asn Leu Thr Leu Ala Leu Glu Ala
    290                 295                 300

Lys Thr Gly Lys Leu His Gln Glu Val Asn Leu Val Val Met Arg Val
305                 310                 315                 320

Ala Gln Leu Asn Asn Thr Leu Thr Cys Glu Val Met Gly Pro Thr Ser
                325                 330                 335

Pro Lys Met Arg Leu Thr Leu Lys Gln Glu Asn Gln Glu Ala Arg Val
            340                 345                 350

Ser Glu Glu Gln Lys Val Val Gln Val Val Ala Pro Glu Thr Gly Leu

```
                      355                 360                 365
Trp Gln Cys Leu Leu Ser Glu Gly Asp Lys Val Lys Met Asp Ser Arg
    370                 375                 380

Ile Gln Val Leu Ser Arg Gly Val Asn Gln Thr Val Phe Leu Ala Cys
385                 390                 395                 400

Val Leu Gly Gly Ser Phe Gly Phe Leu Gly Phe Leu Gly Leu Cys Ile
                405                 410                 415

Leu Cys Cys Val Arg Cys Arg His Gln Gln Arg Gln Ala Ala Arg Met
            420                 425                 430

Ser Gln Ile Lys Arg Leu Leu Ser Glu Lys Lys Thr Cys Gln Cys Pro
        435                 440                 445

His Arg Met Gln Lys Ser His Asn Leu Ile
    450                 455

<210> SEQ ID NO 5
<211> LENGTH: 21
<212> TYPE: DNA
<213> ORGANISM: Artificial
<220> FEATURE:
<223> OTHER INFORMATION: Synthetic

<400> SEQUENCE: 5
gaagtgggtg tgccattcag a                                         21

<210> SEQ ID NO 6
<211> LENGTH: 24
<212> TYPE: DNA
<213> ORGANISM: Artificial
<220> FEATURE:
<223> OTHER INFORMATION: Synthetic

<400> SEQUENCE: 6
aaagctcaga agcagacaga gtca                                      24

<210> SEQ ID NO 7
<211> LENGTH: 25
<212> TYPE: DNA
<213> ORGANISM: Artificial
<220> FEATURE:
<223> OTHER INFORMATION: Synthetic

<400> SEQUENCE: 7
ttccaaaagc ctacagcagg cccag                                     25

<210> SEQ ID NO 8
<211> LENGTH: 21
<212> TYPE: DNA
<213> ORGANISM: Artificial
<220> FEATURE:
<223> OTHER INFORMATION: Synthetic

<400> SEQUENCE: 8
tcatctcccc ttcctgaacc t                                         21

<210> SEQ ID NO 9
<211> LENGTH: 21
<212> TYPE: DNA
<213> ORGANISM: Artificial
<220> FEATURE:
<223> OTHER INFORMATION: Synthetic

<400> SEQUENCE: 9
cccagccaca agaagaagaa a                                         21
```

<210> SEQ ID NO 10
<211> LENGTH: 26
<212> TYPE: DNA
<213> ORGANISM: Artificial
<220> FEATURE:
<223> OTHER INFORMATION: Synthetic

<400> SEQUENCE: 10
cttcccccgc atccattttt ctgttc                                          26

<210> SEQ ID NO 11
<211> LENGTH: 22
<212> TYPE: DNA
<213> ORGANISM: Artificial
<220> FEATURE:
<223> OTHER INFORMATION: Synthetic

<400> SEQUENCE: 11
ggtctcgaac tcatgagctc aa                                              22

<210> SEQ ID NO 12
<211> LENGTH: 25
<212> TYPE: DNA
<213> ORGANISM: Artificial
<220> FEATURE:
<223> OTHER INFORMATION: Synthetic

<400> SEQUENCE: 12
ggcatagtga cacacacctg taatt                                           25

<210> SEQ ID NO 13
<211> LENGTH: 27
<212> TYPE: DNA
<213> ORGANISM: Artificial
<220> FEATURE:
<223> OTHER INFORMATION: Synthetic

<400> SEQUENCE: 13
tgatccactc accttggcct ctcagag                                         27

<210> SEQ ID NO 14
<211> LENGTH: 25
<212> TYPE: DNA
<213> ORGANISM: Artificial
<220> FEATURE:
<223> OTHER INFORMATION: Synthetic

<400> SEQUENCE: 14
gtcagggagc ttactttctt tgttg                                           25

<210> SEQ ID NO 15
<211> LENGTH: 26
<212> TYPE: DNA
<213> ORGANISM: Artificial
<220> FEATURE:
<223> OTHER INFORMATION: Synthetic

<400> SEQUENCE: 15
tgttagtgtc cctgagtaag tggatt                                          26

<210> SEQ ID NO 16
<211> LENGTH: 27
<212> TYPE: DNA
<213> ORGANISM: Artificial
<220> FEATURE:

```
<223> OTHER INFORMATION: Synthetic

<400> SEQUENCE: 16
ctcagctcca caccCctacc aagttgg                                            27

<210> SEQ ID NO 17
<211> LENGTH: 142
<212> TYPE: DNA
<213> ORGANISM: Artificial
<220> FEATURE:
<223> OTHER INFORMATION: Synthetic

<400> SEQUENCE: 17
tgtttgcctg tgacatgaac tcattgtgac acaaaccact gtgctagggg ggatccacta        60
gtaacggccg ccagtgtgct ggaattcgcc ctcgcaaggg ccaggcatat aagtacacaa       120
taaacaaatg gcagctctct cc                                               142

<210> SEQ ID NO 18
<211> LENGTH: 99
<212> TYPE: DNA
<213> ORGANISM: Artificial
<220> FEATURE:
<223> OTHER INFORMATION: Synthetic

<400> SEQUENCE: 18
cccctccttc cttccccagg cactttccaa gtgtcaactc tagagcctat cgcggccgca        60
ccggtataac ttcgtataat gtatgctata cgaagttat                               99

<210> SEQ ID NO 19
<211> LENGTH: 90
<212> TYPE: DNA
<213> ORGANISM: Artificial
<220> FEATURE:
<223> OTHER INFORMATION: Synthetic

<400> SEQUENCE: 19
ataacttcgt ataatgtatg ctatacgaag ttatgtcgac gtagcctatt tctctagatc        60
caaaatgatg acaacaaaag gtaccttgtg                                         90

<210> SEQ ID NO 20
<211> LENGTH: 20
<212> TYPE: DNA
<213> ORGANISM: Artificial
<220> FEATURE:
<223> OTHER INFORMATION: Synthetic

<400> SEQUENCE: 20
gcagctctgc cctcattcag                                                    20

<210> SEQ ID NO 21
<211> LENGTH: 21
<212> TYPE: DNA
<213> ORGANISM: Artificial
<220> FEATURE:
<223> OTHER INFORMATION: Synthetic

<400> SEQUENCE: 21
catctttgcc gtatggttgg t                                                  21

<210> SEQ ID NO 22
<211> LENGTH: 22
<212> TYPE: DNA
<213> ORGANISM: Artificial
```

```
<220> FEATURE:
<223> OTHER INFORMATION: Synthetic

<400> SEQUENCE: 22
ccccttcgtc cctgctggtt ca                                          22

<210> SEQ ID NO 23
<211> LENGTH: 26
<212> TYPE: DNA
<213> ORGANISM: Artificial
<220> FEATURE:
<223> OTHER INFORMATION: Synthetic

<400> SEQUENCE: 23
caagaagact accctgaaga tgaaga                                      26

<210> SEQ ID NO 24
<211> LENGTH: 23
<212> TYPE: DNA
<213> ORGANISM: Artificial
<220> FEATURE:
<223> OTHER INFORMATION: Synthetic

<400> SEQUENCE: 24
tgtgagtgca acaatggaaa act                                         23

<210> SEQ ID NO 25
<211> LENGTH: 22
<212> TYPE: DNA
<213> ORGANISM: Artificial
<220> FEATURE:
<223> OTHER INFORMATION: Synthetic

<400> SEQUENCE: 25
cgttccccca cccagagacc ca                                          22

<210> SEQ ID NO 26
<211> LENGTH: 19
<212> TYPE: DNA
<213> ORGANISM: Artificial
<220> FEATURE:
<223> OTHER INFORMATION: Synthetic

<400> SEQUENCE: 26
ggcaccgagc agtgacagt                                              19

<210> SEQ ID NO 27
<211> LENGTH: 22
<212> TYPE: DNA
<213> ORGANISM: Artificial
<220> FEATURE:
<223> OTHER INFORMATION: Synthetic

<400> SEQUENCE: 27
ttcaccgtgg atagtccctt tt                                          22

<210> SEQ ID NO 28
<211> LENGTH: 24
<212> TYPE: DNA
<213> ORGANISM: Artificial
<220> FEATURE:
<223> OTHER INFORMATION: Synthetic

<400> SEQUENCE: 28
agttcctggc cctctgggat tccg                                        24
```

<210> SEQ ID NO 29
<211> LENGTH: 26
<212> TYPE: DNA
<213> ORGANISM: Artificial
<220> FEATURE:
<223> OTHER INFORMATION: Synthetic

<400> SEQUENCE: 29
ttgctttctt tctgtagttg atttcc                                         26

<210> SEQ ID NO 30
<211> LENGTH: 21
<212> TYPE: DNA
<213> ORGANISM: Artificial
<220> FEATURE:
<223> OTHER INFORMATION: Synthetic

<400> SEQUENCE: 30
ccggcacact ctcttcttga g                                              21

<210> SEQ ID NO 31
<211> LENGTH: 20
<212> TYPE: DNA
<213> ORGANISM: Artificial
<220> FEATURE:
<223> OTHER INFORMATION: Synthetic

<400> SEQUENCE: 31
tcccaccact gcccagccca                                                20

<210> SEQ ID NO 32
<211> LENGTH: 17
<212> TYPE: DNA
<213> ORGANISM: Artificial
<220> FEATURE:
<223> OTHER INFORMATION: synthetic

<400> SEQUENCE: 32
tgcggccgat cttagcc                                                   17

<210> SEQ ID NO 33
<211> LENGTH: 18
<212> TYPE: DNA
<213> ORGANISM: Artificial
<220> FEATURE:
<223> OTHER INFORMATION: Synthetic

<400> SEQUENCE: 33
ttgaccgatt ccttgcgg                                                  18

<210> SEQ ID NO 34
<211> LENGTH: 21
<212> TYPE: DNA
<213> ORGANISM: Artificial
<220> FEATURE:
<223> OTHER INFORMATION: Synthetic

<400> SEQUENCE: 34
acgagcgggt tcggcccatt c                                              21

<210> SEQ ID NO 35
<211> LENGTH: 100
<212> TYPE: DNA
<213> ORGANISM: Artificial
<220> FEATURE:
<223> OTHER INFORMATION: Synthetic

<400> SEQUENCE: 35
tgaacctgct gctgctgggt gagtcgatta tcctggggag tggagaagct aggccgagcc    60
agttccgggt gtcgccgctg gatcggacct ggaacctggg                         100

<210> SEQ ID NO 36
<211> LENGTH: 90
<212> TYPE: DNA
<213> ORGANISM: Artificial
<220> FEATURE:
<223> OTHER INFORMATION: Synthetic

<400> SEQUENCE: 36
atgccaggga cagccctgat actgtaggta gagtcaaggg ctgtccaagt accggtataa    60
cttcgtataa ggtatcctat acgaagttat                                    90

<210> SEQ ID NO 37
<211> LENGTH: 89
<212> TYPE: DNA
<213> ORGANISM: Artificial
<220> FEATURE:
<223> OTHER INFORMATION: Synthetic

<400> SEQUENCE: 37
ataacttcgt ataaggtatc ctatacgaag ttatctcgac ctgatcttgg agggagacct    60
ggaccgggag acgtgctggg ggcagggtt                                     89

<210> SEQ ID NO 38
<211> LENGTH: 22
<212> TYPE: DNA
<213> ORGANISM: Artificial
<220> FEATURE:
<223> OTHER INFORMATION: Synthetic

<400> SEQUENCE: 38
gatgctcttg gctcttccag aa                                            22

<210> SEQ ID NO 39
<211> LENGTH: 25
<212> TYPE: DNA
<213> ORGANISM: Artificial
<220> FEATURE:
<223> OTHER INFORMATION: Synthetic

<400> SEQUENCE: 39
atgaagccat atagacaacg aaggt                                         25

<210> SEQ ID NO 40
<211> LENGTH: 22
<212> TYPE: DNA
<213> ORGANISM: Artificial
<220> FEATURE:
<223> OTHER INFORMATION: Synthetic

<400> SEQUENCE: 40
ccagctccaa actcccccag cc                                            22

<210> SEQ ID NO 41
<211> LENGTH: 20
<212> TYPE: DNA
<213> ORGANISM: Artificial
<220> FEATURE:
<223> OTHER INFORMATION: Synthetic

```
<400> SEQUENCE: 41
tcagccccag agaccagaag                                              20

<210> SEQ ID NO 42
<211> LENGTH: 22
<212> TYPE: DNA
<213> ORGANISM: Artificial
<220> FEATURE:
<223> OTHER INFORMATION: Synthetic

<400> SEQUENCE: 42
tcaatcgctt gagagcacct aa                                           22

<210> SEQ ID NO 43
<211> LENGTH: 19
<212> TYPE: DNA
<213> ORGANISM: Artificial
<220> FEATURE:
<223> OTHER INFORMATION: Synthetic

<400> SEQUENCE: 43
ttgtcggccc cgtggctca                                               19

<210> SEQ ID NO 44
<211> LENGTH: 17
<212> TYPE: DNA
<213> ORGANISM: Artificial
<220> FEATURE:
<223> OTHER INFORMATION: Synthetic

<400> SEQUENCE: 44
gcggttctcg ggcaaga                                                 17

<210> SEQ ID NO 45
<211> LENGTH: 20
<212> TYPE: DNA
<213> ORGANISM: Artificial
<220> FEATURE:
<223> OTHER INFORMATION: Synthetic

<400> SEQUENCE: 45
tcagggccga gcagaaatag                                              20

<210> SEQ ID NO 46
<211> LENGTH: 25
<212> TYPE: DNA
<213> ORGANISM: Artificial
<220> FEATURE:
<223> OTHER INFORMATION: Synthetic

<400> SEQUENCE: 46
acaccttcgt cctcaccctg agcga                                        25

<210> SEQ ID NO 47
<211> LENGTH: 22
<212> TYPE: DNA
<213> ORGANISM: Artificial
<220> FEATURE:
<223> OTHER INFORMATION: Synthetic

<400> SEQUENCE: 47
ggttcacctc aacctgtttt cc                                           22

<210> SEQ ID NO 48
<211> LENGTH: 18
```

<210> SEQ ID NO 48
<211> LENGTH: 18
<212> TYPE: DNA
<213> ORGANISM: Artificial
<220> FEATURE:
<223> OTHER INFORMATION: Synthetic

<400> SEQUENCE: 48
cgcttccagg tgcgctaa                                                 18

<210> SEQ ID NO 49
<211> LENGTH: 22
<212> TYPE: DNA
<213> ORGANISM: Artificial
<220> FEATURE:
<223> OTHER INFORMATION: Synthetic

<400> SEQUENCE: 49
acctgggccc tgctttcaag cc                                            22

<210> SEQ ID NO 50
<211> LENGTH: 19
<212> TYPE: DNA
<213> ORGANISM: Artificial
<220> FEATURE:
<223> OTHER INFORMATION: Synthetic

<400> SEQUENCE: 50
ggtggagagg ctattcggc                                                19

<210> SEQ ID NO 51
<211> LENGTH: 17
<212> TYPE: DNA
<213> ORGANISM: Artificial
<220> FEATURE:
<223> OTHER INFORMATION: Synthetic

<400> SEQUENCE: 51
gaacacggcg gcatcag                                                  17

<210> SEQ ID NO 52
<211> LENGTH: 23
<212> TYPE: DNA
<213> ORGANISM: Artificial
<220> FEATURE:
<223> OTHER INFORMATION: Synthetic

<400> SEQUENCE: 52
tgggcacaac agacaatcgg ctg                                           23

<210> SEQ ID NO 53
<211> LENGTH: 210
<212> TYPE: PRT
<213> ORGANISM: Artificial
<220> FEATURE:
<223> OTHER INFORMATION: synthetic

<400> SEQUENCE: 53

Met Gln Pro Trp Leu Trp Leu Val Phe Ser Met Lys Leu Ala Val Leu
 1               5                  10                  15

His Gly Asn Ser Val Leu Gln Gln Thr Pro Ala Tyr Ile Lys Val Gln
            20                  25                  30

Thr Asn Lys Met Val Met Leu Ser Cys Glu Ala Lys Ile Ser Leu Ser
        35                  40                  45

Asn Met Arg Ile Tyr Trp Leu Arg Gln Arg Gln Ala Pro Ser Ser Asp
    50                  55                  60

```
Ser His His Glu Phe Leu Ala Leu Trp Asp Ser Ala Lys Gly Thr Ile
 65                  70                  75                  80

His Gly Glu Glu Val Glu Gln Glu Lys Ile Ala Val Phe Arg Asp Ala
                 85                  90                  95

Ser Arg Phe Ile Leu Asn Leu Thr Ser Val Lys Pro Glu Asp Ser Gly
                100                 105                 110

Ile Tyr Phe Cys Met Ile Val Gly Ser Pro Glu Leu Thr Phe Gly Lys
            115                 120                 125

Gly Thr Gln Leu Ser Val Val Asp Phe Leu Pro Thr Thr Ala Gln Pro
130                 135                 140

Thr Lys Lys Ser Thr Leu Lys Lys Arg Val Cys Arg Leu Pro Arg Pro
145                 150                 155                 160

Glu Thr Gln Lys Gly Leu Thr Cys Ser Leu Thr Thr Leu Ser Leu Leu
                165                 170                 175

Val Val Cys Ile Leu Leu Leu Ala Phe Leu Gly Val Ala Val Tyr
            180                 185                 190

Phe Tyr Cys Val Arg Arg Arg Ala Arg Ile His Phe Met Lys Gln Phe
            195                 200                 205

His Lys
    210

<210> SEQ ID NO 54
<211> LENGTH: 243
<212> TYPE: PRT
<213> ORGANISM: Artificial
<220> FEATURE:
<223> OTHER INFORMATION: Synthetic

<400> SEQUENCE: 54

Met Ala Ser Pro Leu Thr Arg Phe Leu Ser Leu Asn Leu Leu Leu
1               5                   10                  15

Gly Glu Ser Ile Ile Leu Gly Ser Gly Glu Ala Arg Pro Ser Gln Phe
                20                  25                  30

Arg Val Ser Pro Leu Asp Arg Thr Trp Asn Leu Gly Glu Thr Val Glu
            35                  40                  45

Leu Lys Cys Gln Val Leu Leu Ser Asn Pro Thr Ser Gly Cys Ser Trp
 50                 55                  60

Leu Phe Gln Pro Arg Gly Ala Ala Ala Ser Pro Thr Phe Leu Leu Tyr
 65                 70                  75                  80

Leu Ser Gln Asn Lys Pro Lys Ala Ala Glu Gly Leu Asp Thr Gln Arg
                85                  90                  95

Phe Ser Gly Lys Arg Leu Gly Asp Thr Phe Val Leu Thr Leu Ser Asp
                100                 105                 110

Phe Arg Arg Glu Asn Glu Gly Tyr Tyr Phe Cys Ser Ala Leu Ser Asn
            115                 120                 125

Ser Ile Met Tyr Phe Ser His Phe Val Pro Val Phe Leu Pro Ala Lys
130                 135                 140

Pro Thr Thr Thr Pro Ala Pro Arg Pro Pro Thr Pro Ala Pro Thr Ile
145                 150                 155                 160

Ala Ser Gln Pro Leu Ser Leu Arg Pro Glu Ala Cys Arg Pro Ala Ala
                165                 170                 175

Gly Gly Ala Val Lys Gly Thr Gly Leu Asp Phe Ala Cys Asp Ile Tyr
            180                 185                 190

Ile Trp Ala Pro Leu Ala Gly Ile Cys Val Ala Leu Leu Leu Ser Leu
            195                 200                 205
```

```
Ile Ile Thr Leu Ile Cys Tyr His Arg Ser Arg Lys Arg Val Cys Lys
        210                 215                 220

Cys Pro Arg Pro Leu Val Arg Gln Glu Gly Lys Pro Arg Pro Ser Glu
225                 230                 235                 240

Lys Ile Val

<210> SEQ ID NO 55
<211> LENGTH: 151
<212> TYPE: DNA
<213> ORGANISM: Artificial
<220> FEATURE:
<223> OTHER INFORMATION: Synthetic

<400> SEQUENCE: 55
tatggagtga aagcctttgg tgtctgagat ctggtcttag ttaaactctg ggatcggcgc      60
gccgaattcc tgcagcccgg gctcgagata acttcgtata atgtatgcta tacgaagtta    120
tatgcatccg ggtaggggag cgcttttcc                                      151

<210> SEQ ID NO 56
<211> LENGTH: 151
<212> TYPE: DNA
<213> ORGANISM: Artificial
<220> FEATURE:
<223> OTHER INFORMATION: Synthetic

<400> SEQUENCE: 56
agtattgttt tgccaagttc taattccatc agacctcgac ctgcagccct agataacttc      60
gtataatgta tgctatacga agttatccta ggccagaggg cttgggttga cagaaactca    120
gtggcattct tatccagagt ttctctacac c                                   151

<210> SEQ ID NO 57
<211> LENGTH: 293
<212> TYPE: PRT
<213> ORGANISM: Human

<400> SEQUENCE: 57

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
    130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
```

```
                        165                 170                 175
Leu Ala Phe Gln Lys Ala Ser Ser Ile Val Tyr Lys Lys Glu Gly Glu
                180                 185                 190
Gln Val Glu Phe Ser Phe Pro Leu Ala Phe Thr Val Glu Lys Leu Thr
            195                 200                 205
Gly Ser Gly Glu Leu Trp Trp Gln Ala Glu Arg Ala Ser Ser Ser Lys
        210                 215                 220
Ser Trp Ile Thr Phe Asp Leu Lys Asn Lys Glu Val Ser Val Lys Arg
225                 230                 235                 240
Val Thr Gln Asp Pro Lys Leu Gln Met Gly Lys Lys Leu Pro Leu His
                245                 250                 255
Leu Thr Leu Pro Gln Ala Leu Pro Gln Tyr Ala Gly Ser Gly Asn Leu
            260                 265                 270
Thr Leu Ala Leu Glu Ala Lys Thr Gly Lys Leu His Gln Glu Val Asn
        275                 280                 285
Leu Val Val Met Arg
    290

<210> SEQ ID NO 58
<211> LENGTH: 151
<212> TYPE: PRT
<213> ORGANISM: Human

<400> SEQUENCE: 58

Val Leu His Gly Asn Ser Val Leu Gln Gln Thr Pro Ala Tyr Ile Lys
1               5                   10                  15
Val Gln Thr Asn Lys Met Val Met Leu Ser Cys Glu Ala Lys Ile Ser
                20                  25                  30
Leu Ser Asn Met Arg Ile Tyr Trp Leu Arg Gln Arg Gln Ala Pro Ser
            35                  40                  45
Ser Asp Ser His His Glu Phe Leu Ala Leu Trp Asp Ser Ala Lys Gly
        50                  55                  60
Thr Ile His Gly Glu Glu Val Glu Gln Glu Lys Ile Ala Val Phe Arg
65                  70                  75                  80
Asp Ala Ser Arg Phe Ile Leu Asn Leu Thr Ser Val Lys Pro Glu Asp
                85                  90                  95
Ser Gly Ile Tyr Phe Cys Met Ile Val Gly Ser Pro Glu Leu Thr Phe
            100                 105                 110
Gly Lys Gly Thr Gln Leu Ser Val Val Asp Phe Leu Pro Thr Thr Ala
        115                 120                 125
Gln Pro Thr Lys Lys Ser Thr Leu Lys Lys Arg Val Cys Arg Leu Pro
    130                 135                 140
Arg Pro Glu Thr Gln Lys Gly
145                 150

<210> SEQ ID NO 59
<211> LENGTH: 152
<212> TYPE: PRT
<213> ORGANISM: Human

<400> SEQUENCE: 59

Arg Pro Ser Gln Phe Arg Val Ser Pro Leu Asp Arg Thr Trp Asn Leu
1               5                   10                  15
Gly Glu Thr Val Glu Leu Lys Cys Gln Val Leu Leu Ser Asn Pro Thr
                20                  25                  30
Ser Gly Cys Ser Trp Leu Phe Gln Pro Arg Gly Ala Ala Ala Ser Pro
```

-continued

```
                35                  40                  45
Thr Phe Leu Leu Tyr Leu Ser Gln Asn Lys Pro Lys Ala Ala Glu Gly
        50                  55                  60

Leu Asp Thr Gln Arg Phe Ser Gly Lys Arg Leu Gly Asp Thr Phe Val
65                  70                  75                  80

Leu Thr Leu Ser Asp Phe Arg Arg Glu Asn Glu Gly Tyr Tyr Phe Cys
                85                  90                  95

Ser Ala Leu Ser Asn Ser Ile Met Tyr Phe Ser His Phe Val Pro Val
            100                 105                 110

Phe Leu Pro Ala Lys Pro Thr Thr Thr Pro Ala Pro Arg Pro Pro Thr
        115                 120                 125

Pro Ala Pro Thr Ile Ala Ser Gln Pro Leu Ser Leu Arg Pro Glu Ala
    130                 135                 140

Cys Arg Pro Ala Ala Gly Gly Ala
145                 150
```

HUMANIZED T CELL CO-RECEPTOR MICE

CROSS REFERENCE TO RELATED APPLICATIONS

This application claims benefit under 35 U.S.C. §119(e) of U.S. Provisional Patent Application Ser. No. 61/890,915, filed Oct. 15, 2013, and U.S. Provisional Patent Application Ser. No. 61/766,762, filed Feb. 20, 2013, which applications are hereby incorporated by reference in their entireties.

SEQUENCE LISTING

The present specification makes reference to a sequence listing submitted in electronic Form as an ascii.txt file named "2010794-0440_ST25" on Feb. 20, 2014. The .txt file was generated on Feb. 13, 2014 and is 47 kb in size.

FIELD OF THE INVENTION

Present invention relates to a non-human animal (e.g., rodent, e.g., a mouse or a rat) that is genetically engineered to express a humanized T cell co-receptor. Present invention relates to a non-human animal genetically engineered to express a humanized CD4 or CD8 co-receptor, as well as embryos, tissues, and cells expressing the same. The invention further relates to a non-human animal engineered to co-express a humanized CD4 co-receptor and a humanized Major Histocompatibility Complex (MHC) II. The invention further relates to a non-human animal engineered to co-express a humanized CD8 co-receptor and a humanized MHC I. Methods for making a genetically engineered animal that expresses a humanized T cell co-receptor (e.g., humanized CD4 or CD8) are also provided. Methods for using the genetically engineered animals that express humanized T cell co-receptors for developing human therapeutics are also provided.

BACKGROUND OF THE INVENTION

In the adaptive immune response, foreign antigens are recognized by receptor molecules on B lymphocytes (e.g., immunoglobulins) and T lymphocytes (e.g., T cell receptor or TCR). These foreign antigens are presented on the surface of cells as peptide fragments by specialized proteins, generically referred to as major histocompatibility complex (MHC) molecules. During a T cell-mediated response, antigens presented by MHC molecules are recognized by a T cell receptor. However, more than T cell receptor recognition of MHC-antigen complex is required for an effective immune response. The binding of a T cell co-receptor molecule (e.g., CD4 or CD8) to an invariant portion of MHC is also required.

T cells come in several varieties, including helper T cells and cytotoxic T cells. Helper T cells express co-receptor CD4 and recognize antigens bound to MHC II molecules. CD4+ T cells activate other effector cells in the immune system, e.g., activate MHC II expressing B cells to produce antibody, activate MHC II expressing macrophages to destroy pathogens, etc. The binding of CD4 and T cell receptor to the same MHC II-presented foreign antigen makes a T cell significantly more sensitive to that antigen.

In contrast, cytotoxic T cells (CTLs) express co-receptor CD8 and recognize foreign antigens bound to MHC I molecules. CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide. Similar to CD4, engagement of CD8 makes CTLs more sensitive to MHC I-presented antigen.

Not all antigens will provoke T cell activation due to tolerance mechanisms. However, in some diseases (e.g., cancer, autoimmune diseases) peptides derived from self-proteins become the target of the cellular component of the immune system, which results in destruction of cells presenting such peptides. There has been significant advancement in recognizing antigens that are clinically significant (e.g., antigens associated with various types of cancer). However, in order to improve identification and selection of peptides that will provoke a suitable response in a human T cell, in particular for peptides of clinically significant antigens, there remains a need for in vivo and in vitro systems that mimic aspects of human immune system. Thus, there is a need for biological systems (e.g., genetically modified non-human animals and cells) that can display components of a human immune system.

SUMMARY OF THE INVENTION

Non-human animals comprising non-human cells that express human or humanized molecules that function in the cellular immune response are provided. Humanized rodent loci that encode human or humanized T cell co-receptor (e.g., CD4 and/or CD8) proteins are also provided. Humanized rodent cells that express human or humanized T cell co-receptor (e.g., CD4 and/or CD8) proteins are also provided. In vivo and in vitro systems are provided that comprise humanized rodent cells, wherein the rodent cells express one or more human or humanized immune system molecules.

Provided herein is a genetically modified non-human animal, comprising in its genome a nucleotide sequence encoding a human or humanized T cell co-receptor polypeptide. In various embodiments, provided herein is a genetically modified non-human animal, comprising a nucleotide sequence encoding a chimeric human/non-human T cell co-receptor polypeptide. In one embodiment, the nucleotide sequence is present at an endogenous T cell co-receptor locus. In one embodiment, a human portion of the chimeric T cell co-receptor polypeptide comprises all or substantially all of an extracellular domain of a human T cell co-receptor, and the non-human animal expresses a functional chimeric T cell co-receptor polypeptide. In one embodiment, a non-human portion of the chimeric T cell co-receptor polypeptide comprises at least transmembrane and cytoplasmic domains of a non-human T cell co-receptor, and the non-human animal expresses a functional chimeric T cell co-receptor polypeptide. In one aspect of the invention, the chimeric T cell co-receptor polypeptide is expressed only on T cells of the non-human animal, e.g., it is not expressed on B cells of the non-human animal. In one aspect, the animal does not express a functional non-human T cell co-receptor from its endogenous non-human T cell co-receptor locus. In one aspect of the invention, the chimeric T cell co-receptor polypeptide is comprised in the germline of the non-human animal. In one aspect, the animal comprises at the endogenous T cell co-receptor locus one or two copies of a nucleotide sequence encoding the chimeric T cell co-receptor polypeptide; thus, the animal may be heterozygous or homozygous for the nucleotide sequence encoding chimeric T cell co-receptor polypeptide.

In one embodiment, the T cell co-receptor is CD4. Thus, in one aspect, the invention provides a genetically modified non-human animal comprising a nucleotide sequence encoding a chimeric human/non-human CD4 polypeptide. In one embodiment, the nucleotide sequence is present at an endogenous CD4 locus. In one embodiment, the animal is a rodent, e.g., a mouse or a rat. Thus, in one embodiment, provided is a genetically modified mouse comprising at its endogenous CD4 locus a nucleotide sequence encoding a chimeric human/mouse CD4 polypeptide, wherein a human portion of the chimeric CD4 polypeptide comprises all or substantially all of an extracellular domain of a human CD4 polypeptide, wherein a mouse portion of the chimeric CD4 polypeptide comprises at least transmembrane and cytoplasmic domains of a mouse CD4 polypeptide, and wherein the mouse expresses a functional chimeric human/mouse CD4. In one embodiment, provided herein is a genetically modified mouse comprising at its endogenous CD4 locus a nucleotide sequence encoding a chimeric human/mouse CD4 polypeptide, wherein a human portion of the chimeric polypeptide comprises at least all or substantially all of domains D1-D3 of a human CD4 polypeptide, wherein a mouse portion of the chimeric polypeptide comprises at least transmembrane and cytoplasmic domains of a mouse CD4, and wherein the mouse expresses a functional chimeric human/mouse CD4. In one aspect, the mouse does not express a functional endogenous mouse CD4 from its endogenous mouse CD4 locus. In one embodiment, the nucleotide sequence encoding a chimeric human/mouse CD4 polypeptide is operably linked to endogenous mouse promoter and regulatory sequences. Thus, in one embodiment, the mouse does not express the chimeric CD4 protein on B cells or T cells of CD8 lineage. In one embodiment, the human portion the chimeric CD4 protein comprises an amino acid sequence set forth in SEQ ID NO:57. In one embodiment, the chimeric human/mouse CD4 polypeptide is set forth in SEQ ID NO:4.

In one aspect, the genetically modified non-human animal, e.g., the genetically modified mouse, comprising a chimeric CD4 polypeptide described herein further comprises a human or humanized MHC II protein, wherein the MHC II protein comprises an extracellular domain of a human MHC II α polypeptide and an extracellular domain of a human MHC II β polypeptide. In one aspect, the animal comprises a humanized MHC II protein. In one embodiment, the animal is a mouse and the mouse comprises at the endogenous MHC II locus (1) a nucleotide sequence encoding a chimeric human/mouse MHC II α polypeptide, wherein a human portion of the MHC II α polypeptide comprises an extracellular domain of a human MHC II α, and transmembrane and cytoplasmic domains of endogenous mouse MHC II α polypeptide, and (2) a nucleotide sequence encoding a chimeric human/mouse MHC II β polypeptide, wherein a human portion of the MHC II β polypeptide comprises an extracellular domain of a human MHC II β, and transmembrane and cytoplasmic domains of endogenous mouse MHC II β polypeptide. Genetically modified non-human animals, e.g., mice, comprising nucleotide sequence(s) encoding chimeric human/non-human, e.g., human/mouse, MHC II are described in more detail in U.S. patent application Ser. Nos. 13/661,116 and 13/793,935, incorporated herein by reference in their entirety. In one embodiment, the animal expressing humanized CD4 and/or MHC II proteins is generated via replacement of portions of endogenous non-human, e.g., mouse, CD4 and/or MHC II genes at the CD4 and/or MHC II loci, respectively.

Thus, also provided is a method of modifying a CD4 locus of a non-human animal, e.g. a rodent, e.g., a mouse, to express a chimeric human/mouse CD4 polypeptide comprising replacing at an endogenous CD4 locus a nucleotide sequence encoding endogenous non-human, e.g., mouse, CD4 polypeptide with a nucleotide sequence encoding a chimeric human/mouse CD4 polypeptide. In one embodiment, the chimeric human/non-human, e.g., human/rodent, e.g., human/mouse, CD4 polypeptide comprises at least all or substantially all of domains D1-D3 of a human CD4 polypeptide and at least transmembrane and cytoplasmic domains of an endogenous non-human, e.g., rodent, e.g., mouse, CD4 polypeptide. In one embodiment, the expressed chimeric human/mouse CD4 is set forth in SEQ ID NO:4.

In another embodiment, the T cell co-receptor is CD8. Thus, in one aspect, the invention provides a genetically modified non-human animal comprising a nucleotide sequence(s) encoding a chimeric human/non-human CD8 polypeptide, e.g., chimeric human/non-human CD8α and/or CD8β polypeptide. In one embodiment, the nucleotide sequence is present at an endogenous CD8 locus. In one embodiment, the animal is a rodent, e.g., a mouse or a rat. Thus, in one embodiment, provided is a genetically modified mouse comprising at its endogenous CD8 locus (e.g., endogenous CD8α and/or CD8β locus) a first nucleotide sequence encoding a chimeric human/mouse CD8α polypeptide and a second nucleotide sequence encoding a chimeric human/mouse CD8β polypeptide, wherein the first nucleotide sequence comprises a sequence that encodes all or substantially all of an extracellular domain of a human CD8α polypeptide and at least transmembrane and cytoplasmic domains of a mouse CD8α polypeptide, and wherein the second nucleotide sequence comprises a sequence that encodes all or substantially all of an extracellular domain of a human CD8β polypeptide and at least transmembrane and cytoplasmic domains of a mouse CD8β polypeptide, wherein the mouse expresses a functional chimeric human/mouse CD8 protein. In one aspect, the mouse does not express a functional endogenous mouse CD8 polypeptide from its endogenous mouse CD8 locus. In one embodiment, the first nucleotide sequence is operably linked to endogenous mouse CD8α promoter and regulatory sequences, and the second nucleotide sequence is operably linked to endogenous mouse CD8β promoter and regulatory sequences. Thus, in one embodiment, the mouse does not express the chimeric CD8 protein on B cells or T cells of CD4 lineage. In one embodiment, the human portion the chimeric CD8α and/or β polypeptide comprises immunoglobulin V-like domain of the human CD8α and/or β polypeptide. In one embodiment, a human portion of the chimeric human/mouse CD8α polypeptide comprises an amino acid sequence set forth in SEQ ID NO:59. In one embodiment, a human portion of the chimeric human/mouse CD8β polypeptide comprises an amino acid sequence set forth in SEQ ID NO:58. In one embodiment, the chimeric human/mouse CD8α polypeptide is set forth in SEQ ID NO:54, and the chimeric human/mouse CD8β polypeptide is set forth in SEQ ID NO:53.

In one aspect, the genetically modified non-human animal, e.g., the genetically modified mouse, comprising chimeric CD8α and/or β polypeptide described herein further comprises a human or humanized MHC I protein, wherein the MHC I protein comprises an extracellular domain of a human MHC I polypeptide. In one aspect, the animal comprises a humanized MHC I complex. Thus, the animal may comprise a humanized MHC I protein and a human or humanized β2 microglobulin polypeptide. In one embodiment, the animal is a mouse and the mouse comprises at the endogenous MHC I locus a nucleotide sequence encoding a chimeric human/mouse MHC I polypeptide, wherein a human portion of the MHC I polypeptide comprises an extracellular domain of a human MHC I polypeptide, and transmembrane and cytoplasmic domains of endogenous mouse MHC I polypeptide; and the animal also comprises at an endogenous β2 microglobulin locus a nucleotide sequence encoding a human or humanized β2 microglobulin. Genetically modified non-human animals, e.g., mice, comprising nucleotide sequence(s) encoding chimeric human/non-human, e.g., human/mouse, MHC I and β2 microglobulin are described in more detail in U.S. patent application Ser. Nos. 13/661,159 and 13/793,812, incorporated herein by reference in their entireties. In one embodiment, the animal expressing humanized CD8, MHC I, and/or β2 microglobulin protein(s) is generated via replacement of portions of endogenous non-human, e.g., mouse, CD8, MHC I, and/or β2 microglobulin genes at the CD8, MHC I and/or β2 microglobulin loci, respectively.

Thus, also provided is a method of modifying a CD8 locus of a non-human animal, e.g. a rodent, e.g., a mouse, to express a chimeric human/mouse CD8 polypeptide comprising replacing at an endogenous CD8 locus a nucleotide sequence encoding endogenous non-human, e.g., mouse, CD8 polypeptide with a nucleotide sequence encoding a chimeric human/mouse CD8 polypeptide. In one aspect, the CD8 polypeptide is selected from the group consisting of CD8α, CD8β, and a combination thereof. In one embodiment, the chimeric human/non-human, e.g., human/rodent, e.g., human/mouse, CD8 polypeptide (CD8α and/or CD8β) comprises all or substantially all of an extracellular domain of a human CD8 polypeptide and at least transmembrane and cytoplasmic domains of an endogenous non-human, e.g., rodent, e.g., mouse, CD8 polypeptide.

Also provided herein are cells, e.g., T cells, derived from the non-human animals (e.g., rodents, e.g., mice or rats) described herein. Tissues and embryos derived from the non-human animals described herein are also provided.

Any of the embodiments and aspects described herein can be used in conjunction with one another, unless otherwise indicated or apparent from the context. Other embodiments will become apparent to those skilled in the art from a review of the ensuing detailed description. The following detailed description includes exemplary representations of various embodiments of the invention, which are not restrictive of the invention as claimed. The accompanying figures constitute a part of this specification and, together with the description, serve only to illustrate embodiments and not to limit the invention.

DETAILED DESCRIPTION OF THE INVENTION

Definitions

Figure 1:
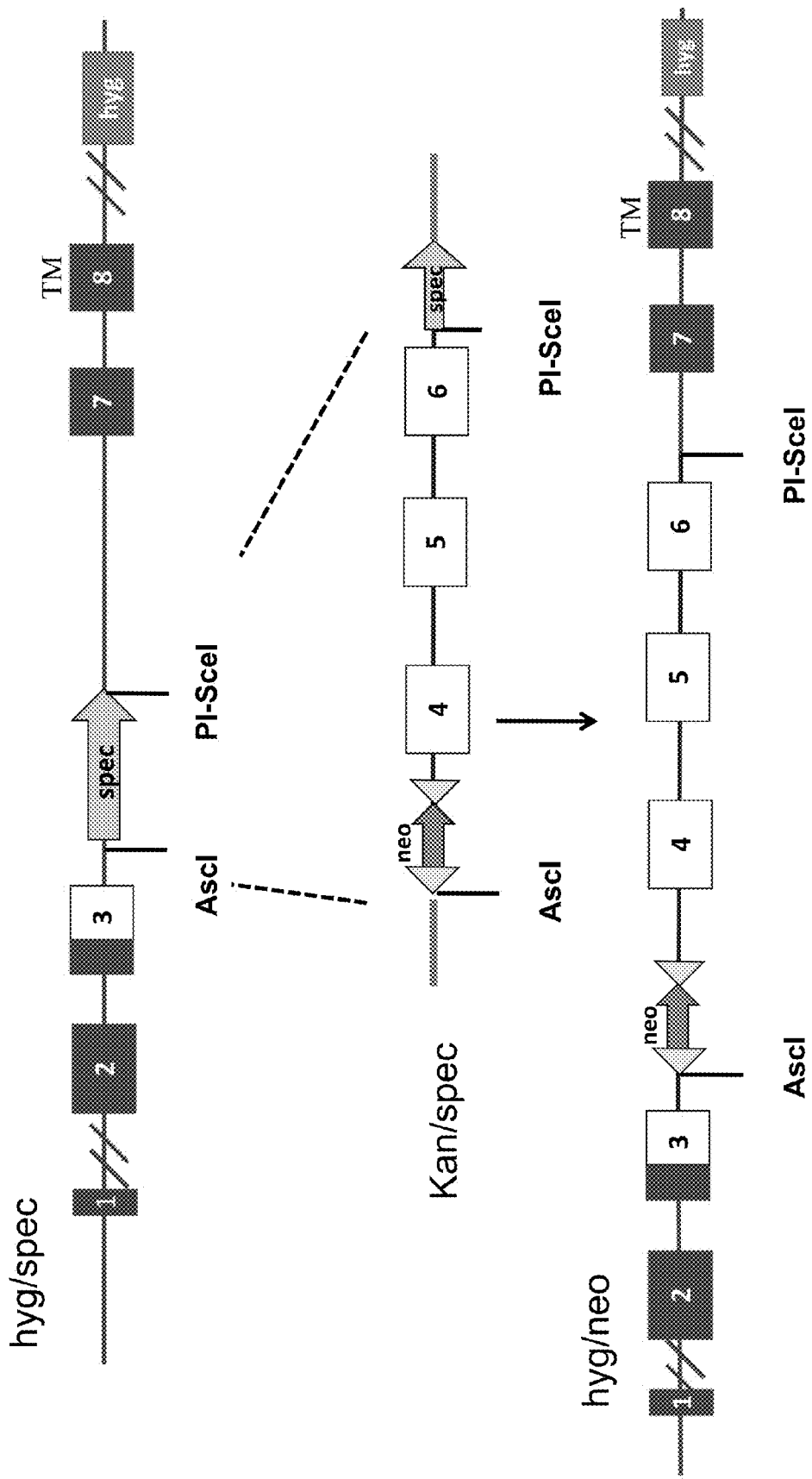
FIG. 1 is a schematic representation (not to scale) of the strategy for generating a humanized CD4 locus. The sequence of mouse exons 3-6, starting just after the signal peptide, was first replaced with the sequence of human exon 3 downstream of the signal peptide (top), and subsequently human exons 4-6 were inserted downstream of human exon 3 by restriction digestion/ligation.

The present invention provides genetically modified non-human animals (e.g., mice, rats, rabbits, etc.) that express humanized T cell co-receptor polypeptides; embryos, cells, and tissues comprising the same; methods of making the same; as well as methods of using the same. Unless defined otherwise, all terms and phrases used herein include the meanings that the terms and phrases have attained in the art, unless the contrary is clearly indicated or clearly apparent from the context in which the term or phrase is used.

The term "conservative," when used to describe a conservative amino acid substitution, includes substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of CD4 or CD8 to bind to MHC II or MHC I, respectively, and increase sensitivity of TCR to MHC-presented antigen. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet et al. ((1992) Exhaustive Matching of the Entire Protein Sequence Database, Science 256: 1443-45), hereby incorporated by reference. In some embodiments, the substitution is a moderately conservative substitution wherein the substitution has a nonnegative value in the PAM250 log-likelihood matrix.

Thus, also encompassed by the invention is a genetically modified non-human animal whose genome comprises (e.g., at an endogenous locus) a nucleotide sequence encoding a humanized T cell co-receptor polypeptide (e.g., CD4 or CD8 polypeptide), wherein the polypeptide comprises conservative amino acid substitutions of the amino acid sequence(s) described herein.

One skilled in the art would understand that in addition to the nucleic acid residues encoding humanized T cell co-receptor polypeptides described herein, due to the degeneracy of the genetic code, other nucleic acids may encode the polypeptides of the invention. Therefore, in addition to a genetically modified non-human animal that comprises in its genome a nucleotide sequence encoding T cell co-receptor polypeptide (e.g., CD4 or CD8 polypeptide) with conservative amino acid substitutions, a non-human animal whose genome comprises a nucleotide sequence that differs from that described herein due to the degeneracy of the genetic code is also provided.

The term "identity" when used in connection with sequence includes identity as determined by a number of different algorithms known in the art that can be used to measure nucleotide and/or amino acid sequence identity. In some embodiments described herein, identities are determined using a ClustalW v. 1.83 (slow) alignment employing an open gap penalty of 10.0, an extend gap penalty of 0.1, and using a Gonnet similarity matrix (MacVector™ 10.0.2, MacVector Inc., 2008). The length of the sequences compared with respect to identity of sequences will depend upon the particular sequences. In various embodiments, identity is determined by comparing the sequence of a mature protein from its N-terminal to its C-terminal. In various embodiments when comparing a chimeric human/non-human sequence to a human sequence, the human portion of the chimeric human/non-human sequence (but not the non-human portion) is used in making a comparison for the purpose of ascertaining a level of identity between a human sequence and a human portion of a chimeric human/non-human sequence (e.g., comparing a human ectodomain of a chimeric human/mouse protein to a human ectodomain of a human protein).

The terms "homology" or "homologous" in reference to sequences, e.g., nucleotide or amino acid sequences, means two sequences which, upon optimal alignment and comparison, are identical in, e.g., at least about 75% of nucleotides or amino acids, e.g., at least about 80% of nucleotides or amino acids, e.g., at least about 90-95% nucleotides or amino acids, e.g., greater than 97% nucleotides or amino acids. One skilled in the art would understand that, for optimal gene targeting, the targeting construct should contain arms homologous to endogenous DNA sequences (i.e., "homology arms"); thus, homologous recombination can occur between the targeting construct and the targeted endogenous sequence.

The term "operably linked" refers to a juxtaposition wherein the components so described are in a relationship permitting them to function in their intended manner. As such, a nucleic acid sequence encoding a protein may be operably linked to regulatory sequences (e.g., promoter, enhancer, silencer sequence, etc.) so as to retain proper transcriptional regulation. In addition, various portions of the chimeric or humanized protein of the invention may be operably linked to retain proper folding, processing, targeting, expression, and other functional properties of the protein in the cell. Unless stated otherwise, various domains of the chimeric or humanized proteins of the invention are operably linked to each other.

The term "replacement" in reference to gene replacement refers to placing exogenous genetic material at an endogenous genetic locus, thereby replacing all or a portion of the endogenous gene with an orthologous or homologous nucleic acid sequence. As demonstrated in the Examples below, nucleic acid sequences of endogenous loci encoding portions of mouse CD4 or CD8 (CD8α and/or CD8β) polypeptides were replaced by nucleotide sequences encoding portions of human CD4 or CD8 (CD8α and/or CD8β) polypeptides, respectively.

"Functional" as used herein, e.g., in reference to a functional polypeptide, refers to a polypeptide that retains at least one biological activity normally associated with the native protein. For example, in some embodiments of the invention, a replacement at an endogenous locus (e.g., replacement at an endogenous non-human CD4 or CD8 locus) results in a locus that fails to express a functional endogenous polypeptide.

Several aspects described herein below for the genetically modified CD4 non-human animals, e.g., animal type; animal strains; cell types; screening, detection and other methods; methods of use; etc., will be applicable to the genetically engineered CD8 animals.

Genetically Modified CD4 Animals

In various embodiments, the invention generally provides genetically modified non-human animals that comprise in their genome, e.g., at an endogenous CD4 locus, a nucleotide sequence encoding a humanized CD4 polypeptide; thus, the animals express a humanized CD4 polypeptide.

Human CD4 gene is localized to chromosome 12, and is thought to contain 10 exons. CD4 gene encodes a protein with amino-terminal hydrophobic signal sequence, encoded by exons 2 and 3 of the gene. The protein comprises 4 immunoglobulin-like domains, commonly referred to as D1-D4 domains. Maddon et al. (1987) Structure and expression of the human and mouse T4 genes, Proc. Natl. Acad. Sci. USA 84:9155-59. D1 domain is believed to be encoded by exon 3 (sequence downstream of signal peptide) and exon 4, while D2, D3, and D4 are encoded by a separate exon each—exons 5, 6, and 7, respectively. Littman (1987) The Structure of the CD4 and CD8 Genes, Ann. Rev. Immunol. 5:561-84; Hanna et al. (1994) Specific Expression of the Human CD4 Gene in Mature CD4+CD8− and Immature CD4+CD8+ T cells and in Macrophages of Transgenic Mice, Mol. Cell. Biol. 14(2):1084-94; Maddon et al., supra. At areas of high protein concentration, such as the area of contact between T cell and antigen-presenting cell, the molecule tends to homodimerize through interactions between opposing D4 domains. Zamoyska (1998) CD4 and CD8: modulators of T cell receptor recognition of antigen and of immune responses? Curr. Opin. Immunol. 10:82-87; Wu et al. (1997) Dimeric association and segmental variability in the structure of human CD4, Nature 387:527; Moldovan et al. (2002) CD4 Dimers Constitute the Functional Component Required for T Cell Activation, J. Immunol. 169:6261-68.

D1 domain of CD4 resembles immunoglobulin variable (V) domain, and, together with a portion of D2 domain, is believed to bind MHC II. Huang et al. (1997) Analysis of the contact sites on the CD4 Molecule with Class II MHC Molecule, J. Immunol. 158:216-25. In turn, MHC II interacts with T cell co-receptor CD4 at the hydrophobic crevice at the junction between MHC II α2 and β2 domains. Wang and Reinherz (2002) Structural Basis of T Cell Recognition of Peptides Bound to MHC Molecules, Molecular Immunology, 38:1039-49.

Domains D3 and D4 of the CD4 co-receptor are believed to interact with the TCR-CD3 complex as the substitution of these two domains abrogated the ability of CD4 to bind to TCR. Vignali et al. (1996) The Two Membrane Proximal Domains of CD4 Interact with the T Cell Receptor, J. Exp. Med. 183:2097-2107. CD4 molecule exists as a dimer, and residues in the D4 domain of the molecule are believed to be responsible for CD4 dimerization. Moldovan et al. (2002) CD4 Dimers Constitute the Functional Components Required for T Cell Activation, J. Immunol. 169:6261-68.

Exon 8 of the CD4 gene encodes the transmembrane domain, while the remainder of the gene encodes the cytoplasmic domain. CD4 cytoplasmic domain possesses many distinct functions. For example, the cytoplasmic domain of CD4 recruits a tyrosine kinase Lck. Lck is a Src family kinase that is associated with CD4 and CD8 cytoplasmic domains and simultaneous binding of the co-receptors and TCRs to the same MHC leads to increased tyrosine phosphorylation of CD3 and ζ chain of the TCR complex, which in turn leads to recruitment of other factors that play a role in T cell activation. Itano and colleagues have proposed that cytoplasmic tail of CD4 also promotes differentiation of CD4+CD8+ T cells into CD4+ lineage by designing and testing expression of hybrid protein comprising CD8 extracellular domain and CD4 cytoplasmic tail in transgenic mice. Itano et al. (1996) The Cytoplasmic Domain of CD4 Promotes the Development of CD4 Lineage T Cells, J. Exp. Med. 183:731-41. The expression of the hybrid protein led to the development of MHC I-specific, CD4 lineage T cells. Id.

CD4 co-receptor appears to be the primary receptor for HIV virus, with the CD4+ T cell depletion being an indicator of disease progression. The cytoplasmic tail of CD4 appears to be essential for delivering apoptotic signal to CD4+ T cells in HIV-induced apoptosis. Specifically, the interaction of CD4 and Lck was shown to potentiate HIV-induced apoptosis in these cells. Corbeil et al. (1996) HIV-induced Apoptosis Requires the CD4 Receptor Cytoplasmic Tail and Is Accelerated by Interaction of CD4 with p56lck, J. Exp. Med. 183:39-48.

T cells develop in the thymus progressing from immature CD4−/CD8− (double negative or DN) thymocytes to CD4+/CD8+ (double positive or DP) thymocytes, which eventually undergo positive selection to become either CD4+ or CD8+ (single positive or SP) T cells. DP thymocytes that receive signals through MHC I-restricted TCR differentiate into CD8+ T cells, while DP thymocytes that receive signals through MHC II-restricted TCR differentiate into CD4+ T cells. The cues received by the DP cell that lead to its differentiation into either CD4+ of CD8+ T cell have been a subject of much research. Various models for CD4/CD8 lineage choice have been proposed and are reviewed in Singer et al. (2008) Lineage fate and intense debate: myths, models and mechanisms of CD4− versus CD8− lineage choice, Nat. Rev. Immunol. 8:788-801.

Deactivation of a specific T cell co-receptor as a result of positive selection is a product of transcriptional regulation. For CD4, it has been shown that an enhancer located 13 kb upstream of exon 1 of CD4 upregulates CD4 expression in CD4+ and CD8+ T cells. Killeen et al. (1993) Regulated expression of human CD4 rescues helper T cell development in mice lacking expression of endogenous CD4, EMBO J. 12:1547-53. A cis-acting transcriptional silencer located within the first intron of murine CD4 gene functions to silence expression of CD4 in cells other than CD4+ T cells. Siu et al. (1994) A transcriptional silencer control the developmental expression of the CD4 gene, EMBO J. 13:3570-3579.

Because important transcriptional regulators (e.g., promoters, enhancers, silencers, etc.) that control CD4 lineage choice were missing in several strains of previously developed transgenic mice expressing human CD4, these mice were not able to recapitulate normal T cell lineage development, and produced immune cells other than CD4+ T cells that expressed CD4. See, e.g., Law et al. (1994) Human CD4 Restores Normal T Cell Development and Function in Mice Deficient in CD4, J. Exp. Med. 179:1233-42 (CD4 expression in CD8+ T cells and B cells); Fugger et al. (1994) Expression of HLA-DR4 and human CD4 transgenes in mice determines the variable region β-chain T-cell repertoire and mediates an HLA-D-restricted immune response, Proc. Natl. Acad. Sci. USA, 91:6151-55 (CD4 expressed on all CD3+ thymocytes and B cells). Thus, in one embodiment, there may be a benefit in developing a genetically modified animal that retains endogenous mouse promoter and other regulatory elements in order for the animal to produce T cells that are capable of undergoing normal T cell development and lineage choice.

Thus, in various embodiments, the invention provides a genetically modified non-human animal, comprising, e.g., at its endogenous T cell co-receptor locus (e.g., CD4 locus), a nucleotide sequence encoding a chimeric human/non-human T cell co-receptor polypeptide. In one embodiment, a human portion of the chimeric polypeptide comprises all or substantially all of an extracellular domain of a human T cell co-receptor. In one embodiment, a non-human portion of the chimeric polypeptide comprises transmembrane and cytoplasmic domains of a non-human T cell co-receptor. In one embodiment, the non-human animal expresses a functional chimeric T cell co-receptor polypeptide. Thus, in one aspect, the invention provides a genetically modified non-human animal comprising at its endogenous CD4 locus a nucleotide sequence encoding a chimeric human/non-human CD4 polypeptide, wherein a human portion of the chimeric polypeptide comprises all or substantially all of an extracellular domain of a human CD4, wherein a non-human portion comprises at least transmembrane and cytoplasmic domains of a non-human CD4, and wherein the animal expresses a functional chimeric CD4 polypeptide. In one aspect, the non-human animal only expresses the humanized CD4 polypeptide, i.e., chimeric human/non-human CD4 polypeptide, and does not express a functional endogenous non-human CD4 protein from its endogenous CD4 locus.

In one embodiment, the human portion of the chimeric human/non-human CD4 polypeptide comprises all or substantially all of the extracellular domain of a human CD4 polypeptide. In another embodiment, the chimeric human/non-human CD4 polypeptide comprises at least all or substantially all MHC II binding domain (e.g., a substantial portion of D1 and D2 domains) of the human CD4 polypeptide; in one embodiment, the human portion of the chimeric human/non-human CD4 polypeptide comprises all or substantially all of D1, D2, and D3 domains of the human CD4 polypeptide; in yet another embodiment, the human portion of the chimeric human/non-human CD4 polypeptide comprises all or substantially all of immunoglobulin-like domains of CD4, e.g., domains termed D1, D2, D3, and D4. In yet another embodiment, the human portion of the chimeric human/non-human CD4 polypeptide comprises in its human portion all or substantially all of the human CD4 sequence that is responsible for interacting with MHC II and/or extracellular portion of a T cell receptor. In yet another embodiment, the human portion of the chimeric human/non-human CD4 polypeptide comprises all or substantially all of the extracellular portion of the human CD4 that is responsible for interacting with MHC II and/or the variable domain of a T cell receptor. Therefore, in one embodiment, the nucleotide sequence encoding the human portion of the chimeric CD4 polypeptide comprises all or substantially all of the coding sequence of domains D1-D2 of the human CD4 (e.g., a portion of exon 3 and exons 4-5 of the human CD4 gene); in another embodiment, it comprises all or substantially all of the coding sequence of D1-D3 of the human CD4 (e.g., portion of exon 3 and exons 4-6 of the human CD4). Thus, in one embodiment, the nucleotide sequence encoding chimeric human/non-human CD4 comprises nucleotide sequences encoding all or substantially all D1-D3 domains of the human CD4. In another embodiment, the nucleotide sequence encoding the human portion of the chimeric CD4 polypeptide comprises the coding sequence of D1-D4 domains of the human CD4 gene. In another embodiment, the nucleotide sequence may comprise the nucleotide sequence encoding mouse CD4 signal peptide, e.g., region encoded by portions of exons 2-3 of the mouse gene. In another embodiment, the nucleotide sequence may comprise the nucleotide sequence encoding a human CD4 signal peptide. In one embodiment, the chimeric human/non-human CD4 polypeptide comprises an amino acid sequence set forth in SEQ ID NO:4, and the human portion of the chimeric polypeptide spans about amino acids 27-319 of SEQ ID NO:4 (set forth separately in SEQ ID NO:57).

In one embodiment, the non-human animal expresses a chimeric human/non-human CD4 polypeptide sequence. In one embodiment, a human portion of the chimeric CD4 sequence comprises one or more conservative or non-conservative modifications.

In one aspect, a non-human animal that expresses a human CD4 sequence is provided, wherein the human CD4 sequence is at least about 85%, 90%, 95%, 96%, 97%, 98%, or 99% identical to a human CD4 sequence. In a specific embodiment, the human CD4 sequence is at least about 90%, 95%, 96%, 97%, 98%, or 99% identical to the human CD4 sequence described in the Examples. In one embodiment, the human CD4 sequence comprises one or more conservative substitutions. In one embodiment, the human CD4 sequence comprises one or more non-conservative substitutions.

In some embodiments, a portion, e.g., a human portion of the chimeric CD4, may comprise substantially all of the sequence indicated herein (e.g., substantially all of a protein domain indicated herein). Substantially all sequence generally includes 85%, 90%, 95%, 96%, 97%, 98%, or 99% of the amino acids believed to represent a particular portion of the protein (e.g., a particular functional domain, etc.). One skilled in the art would understand that the boundaries of a functional domain may vary slightly depending on the alignment and domain prediction methods used.

In one aspect, the non-human portion of the chimeric human/non-human CD4 polypeptide comprises at least transmembrane and cytoplasmic domains of the non-human CD4 polypeptide. Due to the important functions served by CD4 cytoplasmic domain, retention of the endogenous non-human (e.g., mouse) sequence in genetically engineered animals ensures preservation of proper intracellular signaling and other functions of the co-receptor. In one embodiment, the non-human animal is a mouse, and the non-human CD4 polypeptide is a mouse CD4 polypeptide. Although a specific mouse CD4 sequence is described in the Examples, any suitable sequence derived therefrom, e.g., sequence comprising conservative/non-conservative amino acid substitutions, is encompassed herein. In one embodiment, the non-human portion of the chimeric CD4 co-receptor comprises any sequence of the endogenous CD4 that has not been humanized.

The non-human animal described herein may comprise at its endogenous locus a nucleotide sequence encoding a chimeric human/non-human CD4 polypeptide. In one aspect, this results in a replacement of a portion of an endogenous CD4 gene with a nucleotide sequence encoding a portion of a human CD4 polypeptide. In one embodiment, such replacement is a replacement of endogenous nucleotide sequence encoding, e.g., all or substantially all of the extracellular domain of a non-human CD4, e.g., a sequence encoding at least all or substantially all of the first immunoglobulin-like domain (i.e., D1) of a non-human CD4 (e.g., a sequence encoding all or substantially all of domains D1-D2 of a non-human CD4, e.g., a sequence encoding all or substantially all of domains D1-D3 of a non-human CD4, e.g., a sequence encoding all or substantially all of domains D1-D4 of a non-human CD4), with a human nucleotide sequence encoding the same. In one embodiment, the replacement results in a chimeric protein comprising human CD4 sequence that is responsible for interacting with MHC II and/or extracellular portion of a T cell receptor. In yet another embodiment, the replacement results in a chimeric protein comprising human CD4 sequence that is responsible for interacting with MHC II and/or variable domain of a T cell receptor. In one embodiment, the replacement does not comprise a replacement of a CD4 sequence encoding at least transmembrane and cytoplasmic domains of a non-human CD4 polypeptide. Thus, in one aspect, the non-human animal expresses a chimeric human/non-human CD4 polypeptide from the endogenous non-human CD4 locus. In yet another embodiment, the replacement results in a protein comprising a polypeptide sequence set forth in SEQ ID NO:4.

In one embodiment, the nucleotide sequence of the chimeric human/non-human CD4 locus (e.g., chimeric human/rodent CD4 locus, e.g., chimeric human/mouse CD4 locus) described herein is provided. In one aspect, because the chimeric human/non-human (e.g., human/rodent, e.g., human/mouse) CD4 sequence is placed at the endogenous non-human (e.g., rodent, e.g., mouse) CD4 locus, it retains the CD4 enhancer element located upstream of the first CD4 exon. In one embodiment, the replacement at the endogenous non-human (e.g., rodent, e.g., mouse) CD4 locus comprises a replacement of, e.g., a portion of exon 3 encoding D1, and exons 4-6 encoding the rest of D1 and D2-D3 of CD4 polypeptide; thus, in one aspect, the chimeric CD4 locus retains the cis-acting silencer located in intron 1 of the non-human (e.g., mouse) CD4 gene. Thus, in one embodiment, the chimeric locus retains endogenous non-human (e.g., rodent, e.g., mouse) CD4 promoter and regulatory elements. In another embodiment, the chimeric locus may contain human promoter and regulatory elements to the extent those allow proper CD4 expression, CD4+ T cell development, CD4 lineage choice, and co-receptor function.

Thus, in some aspects, the animals of the invention comprise a genetic modification that does not alter proper lineage choice and development of T cells. In one aspect, the animals (e.g., rodents, e.g., mice) of the invention do not express chimeric CD4 polypeptide on immune cells other than cells that normally express CD4. In one aspect, animals do not express CD4 on B cells or CD8+ SP T cells. In one embodiment, the replacement results in retention of elements that allow proper spatial and temporal regulation of CD4 expression.

The genetically modified non-human animal of the invention may be selected from a group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In one aspect, the non-human animal is a mammal. In one aspect, the non-human animal is a small mammal, e.g., of the superfamily Dipodoidea or Muroidea. In one embodiment, the genetically modified animal is a rodent. In one embodiment, the rodent is selected from a mouse, a rat, and a hamster. In one embodiment, the rodent is selected from the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In a specific embodiment, the genetically modified rodent is selected from a true mouse or rat (family Muridae), a gerbil, a spiny mouse, and a crested rat. In one embodiment, the genetically modified mouse is from a member of the family Muridae. In one embodiment, the animal is a rodent. In a specific embodiment, the rodent is selected from a mouse and a rat. In one embodiment, the non-human animal is a mouse.

In a specific embodiment, the non-human animal is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain.

In one embodiment, the non-human animal is a rat. In one embodiment, the rat is selected from a Wistar rat, an LEA strain, a Sprague Dawley strain, a Fischer strain, F344, F6, and Dark Agouti. In one embodiment, the rat strain is a mix of two or more strains selected from the group consisting of Wistar, LEA, Sprague Dawley, Fischer, F344, F6, and Dark Agouti.

Thus, in one embodiment, the invention provides a genetically modified mouse comprising in its genome, e.g., at its endogenous CD4 locus, a nucleotide sequence encoding a chimeric human/mouse CD4 polypeptide, wherein a mouse portion of the chimeric polypeptide comprises at least transmembrane and cytoplasmic domains of a mouse CD4 polypeptide, and wherein the mouse expresses a chimeric human/mouse CD4. In one embodiment, a human portion of the chimeric polypeptide comprises at least all or substantially all of the extracellular domain of a human CD4 polypeptide. In one embodiment, a human portion of the chimeric polypeptide comprises at least all or substantially all of the D1 domain of a human CD4 protein. In one embodiment, a human portion of the chimeric polypeptide comprises at least all or substantially all of D1-D2 domains of a human CD4 protein, e.g., at least all or substantially all of D1-D3 domains of a human CD4 protein, e.g., all or substantially all of D1-D4 domains of a human CD4 protein. Thus, in one embodiment, the mouse comprises at the endogenous CD4 locus a nucleotide sequence comprising at least all or substantially all of exons 4, 5, and 6 of the human CD4 gene, e.g., the sequence of exon 3 of the human CD4 gene encoding a portion of the D1 domain of human CD4 and exons 4-6 of the human CD4 gene. In one embodiment, the mouse comprises at the endogenous CD4 locus a chimeric human/mouse CD4 that comprises a human CD4 sequence that is responsible for interacting with MHC II and/or extracellular portion of a T cell receptor. In another embodiment, the mouse comprises at the endogenous CD4 locus a chimeric human/mouse CD4 that comprises a human CD4 sequence that is responsible for interacting with MHC II and/or variable domain of a T cell receptor. In one embodiment, the nucleotide sequence comprises the sequence encoding mouse CD4 signal peptide. In one embodiment, the mouse comprises a replacement of the nucleotide sequence encoding a mouse CD4 extracellular domain with a nucleotide sequence encoding a human CD4 extracellular domain. In another embodiment, the mouse comprises a replacement of the nucleotide sequence encoding at least all or substantially all of mouse CD4 D1 domain, e.g., a nucleotide sequence encoding at least all or substantially all of mouse CD4 D1-D2 domains, e.g., a nucleotide sequence encoding at least all or substantially all of mouse CD4 D1-D3 domains, with human nucleotide sequence encoding the same. In one embodiment, the mouse does not express a functional endogenous mouse CD4 from it endogenous mouse CD4 locus. In one embodiment, the mouse described herein comprises the chimeric human/mouse CD4 nucleotide sequence in the germline of the mouse. In one embodiment, the mouse retains any endogenous sequences that have not been humanized, e.g., in the embodiment wherein the mouse comprises a replacement of the nucleotide sequence encoding all or substantially all of D1-D3 domains, the mouse retains endogenous nucleotide sequence encoding mouse CD4 D4 domain as well a nucleotide sequence encoding transmembrane and cytoplasmic domains of mouse CD4.

In one aspect, the mouse expressing chimeric human/mouse CD4 protein retains mouse CD4 promoter and regulatory sequences, e.g., the nucleotide sequence in the mouse encoding chimeric human/mouse CD4 is operably linked to endogenous mouse CD4 promoter and regulatory sequences. In one aspect, these mouse regulatory sequences retained in the genetically engineered animal of the invention include the sequences that regulate expression of the chimeric protein at proper stages during T cell development. Thus, in one aspect, the mouse does not express chimeric CD4 on B cells or T cells of CD8 lineage. In one aspect, the mouse also does not express chimeric CD4 on any cell type, e.g., any immune cell type, that normally does not express endogenous CD4.

In various embodiments, a non-human animal (e.g., a rodent, e.g., a mouse or rat) that expresses a functional chimeric CD4 protein from a chimeric CD4 locus as described herein displays the chimeric protein on a cell surface, e.g., T cell surface. In one embodiment, the non-human animal expresses the chimeric CD4 protein on a cell surface in a cellular distribution that is the same as observed in a human. In one aspect, the CD4 protein of the invention is capable of interacting with an MHC II protein expressed on the surface of a second cell, e.g., an antigen presenting cell (APC).

In one embodiment, the non-human animal (e.g., rodent, e.g., mouse) of the invention further comprises a nucleotide sequence encoding a human or humanized MHC II protein, such that the chimeric CD4 protein expressed on the surface of a T cell of the animal is capable of interacting with a human or humanized MHC II expressed on a surface of a second cell, e.g., an antigen presenting cell. In one embodiment, the MHC II protein comprises an extracellular domain of a human MHC II α polypeptide and an extracellular domain of a human MHC II β polypeptide. Exemplary genetically modified animals expressing a human or humanized MHC II polypeptide are described in U.S. patent application Ser. No. 13/661,116, filed Oct. 26, 2012, and U.S. patent application Ser. No. 13/793,935, filed Mar. 11, 2013, incorporated herein by reference in their entireties. Thus, in one embodiment, the animal comprising chimeric CD4 protein described herein may further comprise a humanized MHC II protein, wherein the humanized MHC II protein comprises: (1) a humanized MHC II α polypeptide comprising a human MHC II α extracellular domain and transmembrane and cytoplasmic domains of an endogenous, e.g., mouse, MHC II, wherein the human MHC II α extracellular domain comprises α1 and α2 domains of a human MHC II α and (2) a humanized MHC II β polypeptide comprising a human MHC II β extracellular domain and transmembrane and cytoplasmic domains of an endogenous, e.g., mouse, MHC II, wherein the human MHC II β extracellular domain comprises β1 and β2 domains of a human MHC II β. In one aspect, both humanized MHC II α and β polypeptides are encoded by nucleotide sequences located at endogenous MHC II α and β loci, respectively; in one aspect, the animal does not express functional endogenous MHC II α and β polypeptides. Thus, the MHC II expressed by the animals may be a chimeric human/non-human, e.g., human/rodent (e.g., human/mouse) MHC II protein. A human portion of the chimeric MHC II protein may be derived from a human HLA class II protein selected from the group consisting of HLA-DR, HLA-DQ, and HLA-DP, e.g., HLA-DR4, HLA-DR2, HLA-DQ2.5, HLA-DQ8, or any other HLA class II molecule present in a human population. In the embodiment, wherein the animal is a mouse, a non-human (i.e., a mouse) portion of the chimeric MHC II polypeptide may be derived from a mouse MHC II protein selected from H-2E and H-2A. In one aspect, the non-human animal comprising a chimeric human/non-human CD4 and the humanized MHC II described in U.S. patent application Ser. Nos. 13/661,116 and 13/793,935 may be generated by breeding an animal comprising a chimeric CD4 locus as described herein with an animal comprising a humanized MHC II locus. The animal may also be generated by introducing into ES cells of an animal comprising humanized MHC II locus a nucleotide sequence encoding chimeric CD4, e.g., for replacement at the endogenous CD4 locus; or introducing into ES cells of an animal comprising a chimeric CD4 locus a nucleotide sequence encoding humanized MHC II.

In one embodiment, the genetically modified no-human animal (e.g., mouse) comprising both chimeric human/non-human CD4 and human or humanized MHC II may comprise one or two copies of the genes encoding these proteins; thus, the animal may be heterozygous or homozygous for the genes encoding chimeric CD4 and MHC II (i.e., MHC II α and/or MHC II β), respectively.

In addition to a genetically engineered non-human animal, a non-human embryo (e.g., a rodent, e.g., a mouse or a rat embryo) is also provided, wherein the embryo comprises a donor ES cell that is derived from a non-human animal (e.g., a rodent, e.g., a mouse or a rat) as described herein. In one aspect, the embryo comprises an ES donor cell that comprises the chimeric CD4 gene, and host embryo cells.

Also provided is a tissue, wherein the tissue is derived from a non-human animal (e.g., a rodent, e.g., a mouse or a rat) as described herein, and expresses the chimeric CD4 protein.

In addition, a non-human cell isolated from a non-human animal as described herein is provided. In one embodiment, the cell is an ES cell. In one embodiment, the cell is a T cell, e.g., a CD4+ T cell. In one embodiment, the cell is a helper T cell ($T_H$ cell). In one embodiment, the $T_H$ cell is an effector $T_H$ cell, e.g., $T_H1$ cell or $T_H2$ cell.

Also provided is a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a non-human induced pluripotent cell comprising gene encoding a chimeric CD4 polypeptide as described herein is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

In one aspect, an in vitro preparation is provided that comprises a T cell that bears a chimeric CD4 protein on its surface and a second cell that binds the chimeric CD4. In one embodiment, the second cell is a cell, e.g., an APC, expressing an MHC II polypeptide, e.g., a chimeric human/non-human MHC II protein. In one embodiment, the chimeric CD4 on the surface of the first cell interacts with chimeric MHC II on the surface of the second cell. In one embodiment, the chimeric CD4 protein retains interaction with endogenous cytosolic molecules, e.g., endogenous cytosolic signaling molecules (e.g., endogenous Lck, etc.).

Also provided is a method for making a genetically engineered non-human animal (e.g., a genetically engineered rodent, e.g., a mouse or rat) described herein. In one embodiment, the method for making a genetically engineered non-human animal results in the animal that comprises at an endogenous CD4 locus a nucleotide sequence encoding a chimeric human/non-human CD4 polypeptide. In some embodiments, the method utilizes a targeting construct made using VELOCIGENE® technology, introducing the construct into ES cells, and introducing targeted ES cell clones into a mouse embryo using VELOCIMOUSE® technology, as described in the Examples.

In one embodiment, the invention comprises a method of modifying a CD4 locus of a non-human animal to express a chimeric human/non-human CD4 polypeptide described herein. In one embodiment, the invention provides a method of modifying a CD4 locus of a mouse to express a chimeric human/mouse CD4 polypeptide comprising replacing at an endogenous CD4 locus of a mouse a nucleotide sequence encoding an endogenous mouse CD4 polypeptide with a nucleotide sequence encoding a chimeric human/mouse CD4 polypeptide. In one aspect of the method, the chimeric human/mouse CD4 polypeptide comprises all or substantially all of an extracellular domain of a human CD4 polypeptide and at least transmembrane and cytoplasmic domains of an endogenous mouse CD4 polypeptide. In another aspect of the method, the chimeric human/mouse CD4 polypeptide comprises all or substantially all of D1-D2 domains of a human CD4 polypeptide. In yet another embodiment, the chimeric human/mouse CD4 polypeptide comprises all or substantially all of D1-D3 domains of a human CD4 polypeptide. In yet another embodiment, the chimeric human/mouse CD4 polypeptide comprises all or substantially all of amino acid sequence of human CD4 that is responsible for interacting with MHC II and/or an extracellular domain of a T cell receptor. In yet another embodiment, the chimeric human/mouse CD4 polypeptide comprises all or substantially all of amino acid sequence of human CD4 that is responsible for interacting with MHC II and/or a variable domain of a T cell receptor.

Thus, a nucleotide construct for generating genetically modified animals described herein is also provided. In one aspect, the nucleotide sequence comprises 5' and 3' homology arms, a DNA fragment comprising human CD4 gene sequence (e.g., human CD4 extracellular domain gene sequence, e.g., gene sequence of all or substantially all of domains D1-D2 of human CD4, e.g., gene sequence of all or substantially all of domains D1-D3 and/or D2-D3 of human CD4, e.g., gene sequence of all or substantially all of domains D1-D4 of human CD4), and a selection cassette flanked by recombination sites. In one embodiment, human CD4 gene sequence is a genomic sequence that comprises introns and exons of human CD4. In one embodiment, homology arms are homologous to non-human (e.g., mouse) CD4 genomic sequence. An exemplary construct of the invention is depicted in FIG. 1, bottom diagram.

A selection cassette is a nucleotide sequence inserted into a targeting construct to facilitate selection of cells (e.g., ES cells) that have integrated the construct of interest. A number of suitable selection cassettes are known in the art. Commonly, a selection cassette enables positive selection in the presence of a particular antibiotic (e.g., Neo, Hyg, Pur, CM, SPEC, etc.). In addition, a selection cassette may be flanked by recombination sites, which allow deletion of the selection cassette upon treatment with recombinase enzymes. Commonly used recombination sites are loxP and Frt, recognized by Cre and Flp enzymes, respectively, but others are known in the art. A selection cassette may be located anywhere in the construct outside the coding region. In one embodiment, the selection cassette is located between exon 3 and exon 4 of the human CD4 sequence.

Upon completion of gene targeting, ES cells or genetically modified non-human animals are screened to confirm successful incorporation of exogenous nucleotide sequence of interest or expression of exogenous polypeptide. Numerous techniques are known to those skilled in the art, and include (but are not limited to) Southern blotting, long PCR, quantitative PCR (e.g., real-time PCR using TAQMAN®), fluorescence in situ hybridization, Northern blotting, flow cytometry, Western analysis, immunocytochemistry, immunohistochemistry, etc. In one example, non-human animals (e.g., mice) bearing the genetic modification of interest can be identified by screening for loss of mouse allele and/or gain of human allele using a modification of allele assay described in Valenzuela et al. (2003) High-throughput engineering of the mouse genome coupled with high-resolution expression analysis, Nature Biotech. 21(6):652-659. Other assays that identify a specific nucleotide or amino acid sequence in the genetically modified animals are known to those skilled in the art.

In one aspect, a method for making a chimeric human/non-human CD4 molecule is provided, comprising expressing in a single cell a chimeric CD4 protein from a nucleotide construct as described herein. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric CD4 protein is provided. In one embodiment, the cell comprises an expression vector comprising a chimeric CD4 sequence as described herein. In one embodiment, the cell is selected from CHO, COS, 293, HeLa, and a retinal cell expressing a viral nucleic acid sequence (e.g., a PERC.6™ cell).

A chimeric CD4 molecule made by a non-human animal as described herein is also provided, wherein, in one embodiment, the chimeric CD4 molecule comprises an amino acid sequence of all or substantially all of an extracellular domain of a human CD4 protein, and at least transmembrane and cytoplasmic domains from a non-human CD4 protein, e.g., mouse CD4 protein. In another embodiment, a chimeric CD4 molecule made by a non-human animal as described herein is provided, wherein the chimeric CD4 molecule comprises an amino acid sequence of at least all or substantially all D1 domain of a human CD4, e.g., at least all or substantially all D1-D2 domains of a human CD4, e.g., at least all or substantially all D1-D3 domains of a human CD4, e.g., an amino acid sequence of human CD4 that is responsible for binding MHC II and/or extracellular domain of a TCR, e.g., an amino acid sequence of human CD4 that is responsible for binding MHC II and/or a variable domain of a TCR; and wherein the remainder of the protein (e.g., transmembrane domain, cytoplasmic domain, any portion of extracellular domain that has not been humanized) is derived from the endogenous non-human protein sequence.

Various embodiments described herein above in relation to animals expressing chimeric CD4 protein, as well as cells and tissues comprising the same, may be applicable to the embodiments describing non-human animals expressing chimeric human/non-human CD8, described herein below, or animals expressing other important chimeric human/non-human T cell co-receptors.

Genetically Modified CD8 Animals

In various embodiments, the invention generally provides genetically modified non-human animals that comprise in their genome, e.g., at an endogenous CD8 locus, a nucleotide sequence encoding a humanized CD8 polypeptide; thus, the animals express a humanized CD8 polypeptide. In various embodiments, the invention provides non-human animals that comprise in their genome, e.g., at an endogenous CD8 locus, a nucleotide sequence encoding a humanized CD8α polypeptide and/or a nucleotide sequence encoding a humanized CD8β polypeptide. Thus, the genetically modified non-human animal of the invention expresses a humanized CD8α and/or a humanized CD8β polypeptide(s).

Human CD8 protein is typically expressed on cell surface as heterodimer of two polypeptides, CD8α and CD8β, although disulfide-linked homodimers and homomultimers have also been detected (e.g., in NK cells and intestinal γδ T cells, which express CD8αα). The genes encoding human CD8α and CD8β are located in close proximity to each other on chromosome 2. Nakayama et al. (1992) Recent Duplication of the Two Human CD8 β-chain genes, J. Immunol. 148:1919-27. CD8α protein contains a leader peptide, an immunoglobulin V-like region, a hinge region, a transmembrane domain and a cytoplasmic tail. Norment et al. (1989) Alternatively Spliced mRNA Encodes a Secreted Form of Human CD8α. Characterization of the Human CD8α gene, J. Immunol. 142:3312-19. The exons/introns of the CD8α gene are depicted schematically in FIGS. 4 and 5.

Human CD8β gene lies upstream of the CD8α gene on chromosome 2. Multiple isoforms generated by alternative splicing of CD8β gene have been reported, with one isoform predicted to lack a transmembrane domain and generate a secreted protein. Norment et al. (1988) A second subunit of CD8 is expressed in human T cells, EMBO J. 7:3433-39. The exons/introns of CD8β gene are depicted schematically in FIGS. 3 and 5.

The membrane-bound CD8β protein contains an N-terminal signal sequence, followed by immunoglobulin V-like domain, a short extracellular hinge region, a transmembrane domain, and a cytoplasmic tail. See, Littman (1987) The structure of the CD4 and CD8 genes, Ann Rev. Immunol. 5:561-84. The hinge region is a site of extensive glycosylation, which is thought to maintain its conformation and protect the protein from cleavage by proteases. Leahy (1995) A structural view of CD4 and CD8, FASEB J. 9:17-25.

CD8 protein is commonly expressed on cytotoxic T cells, and interacts with MHC I molecules. The interaction is mediated through CD8 binding to the $α_3$ domain of MHC I. Although binding of MHC class I to CD8 is about 100-fold weaker than binding of TCR to MHC class I, CD8 binding enhances the affinity of TCR binding. Wooldridge et al. (2010) MHC Class I Molecules with Superenhanced CD8 Binding Properties Bypass the Requirement for Cognate TCR Recognition and Nonspecifically Activate CTLs, J. Immunol. 184:3357-3366.

CD8 binding to MHC class I molecules is species-specific; the mouse homolog of CD8, Lyt-2, was shown to bind $H-2D^d$ molecules at the α3 domain, but it did not bind HLA-A molecules. Connolly et al. (1988) The Lyt-2 Molecule Recognizes Residues in the Class I α3 Domain in Allogeneic Cytotoxic T Cell Responses, J. Exp. Med. 168:325-341. Differential binding was presumably due to CDR-like determinants (CDR1- and CDR2-like) on CD8 that were not conserved between humans and mice. Sanders et al. (1991) Mutations in CD8 that Affect Interactions with HLA Class I and Monoclonal Anti-CD8 Antibodies, J. Exp. Med. 174:371-379; Vitiello et al. (1991) Analysis of the HLA-restricted Influenza-specific Cytotoxic T Lymphocyte Response in Transgenic Mice Carrying a Chimeric Human-Mouse Class I Major Histocompatibility Complex, J. Exp. Med. 173:1007-1015; and, Gao et al. (1997) Crystal structure of the complex between human CD8αα and HLA-A2, Nature 387:630-634. It has been reported that CD8 binds HLA-A2 in a conserved region of the α3 domain (at position 223-229). A single substitution (V245A) in HLA-A reduced binding of CD8 to HLA-A, with a concomitant large reduction in T cell-mediated lysis. Salter et al. (1989), Polymorphism in the $α_3$ domain of HLA-A molecules affects binding to CD8, Nature 338:345-348. In general, polymorphism in the α3 domain of HLA-A molecules also affected binding to CD8. Id. In mice, amino acid substitution at residue 227 in $H-2D^d$ affected the binding of mouse Lyt-2 to $H-2D^d$, and cells transfected with a mutant $H-2D^d$ were not lysed by CD8+ T cells. Potter et al. (1989) Substitution at residue 227 of H-2 class I molecules abrogates recognition by CD8-dependent, but not CD8-independent, cytotoxic T lymphocytes, Nature 337:73-75. Thus, expression of human or humanized CD8 may be beneficial for studying T cell responses to antigen presented by human or humanized MHC I.

Similarly to CD4, the cytoplasmic domain of CD8 interacts with tyrosine kinase Lck, which in turn leads to T cell activation. Although Lck seems to interact with the cytoplasmic domain of CD8α, it appears that this interaction is regulated by the presence of the cytoplasmic domain of CD8β because mutations or deletion of CD8β cytoplasmic domain resulted in reduced CD8α-associated Lck activity. Irie et al. (1998) The cytoplasmic domain of CD8β Regulates Lck Kinase Activation and CD8 T cell Development, J. Immunol. 161:183-91. The reduction in Lck activity was associated with impairment in T cell development. Id.

Expression of CD8 on appropriate cells, e.g., cytotoxic T cells, is tightly regulated by a variety of enhancer elements located throughout the CD8 locus. For instance, at least 4 regions of DNAse I-hypersensitivity, regions often associated with regulator binding, have been identified at the CD8 locus. Hosert et al. (1997) A CD8 genomic fragment that directs subset-specific expression of CD8 in transgenic mice, J. Immunol. 158:4270-81. Since the discovery of these DNAse I-hypersensitive regions at CD8 locus, at least 5 enhancer elements have been identified, spread throughout the CD8 locus, that regulate expression of CD8α and/or β in T cells of various lineages, including DP, CD8 SP T cells, or cells expressing γδTCR. See, e.g., Kioussis et al. (2002) Chromatin and CD4, CD8A, and CD8B gene expression during thymic differentiation, Nature Rev. 2:909-919 and Online Erratum; Ellmeier et al. (1998) Multiple Development Stage-Specific Enhancers Regulate CD8 Expression in Developing Thymocytes and in Thymus-Independent T cells, Immunity 9:485-96.

Thus, similarly to the benefit derived from retaining endogenous CD4 promoter and regulatory elements for human or humanized CD4 genetically modified animals, in some embodiments, there may be a benefit in developing a genetically modified non-human animal that retains endogenous mouse promoter and regulatory elements that would control expression of human or humanized CD8. There may be a particular benefit in creating genetically modified animals comprising a replacement of endogenous non-human sequences encoding CD8α and/or β proteins with those encoding human or humanized CD8α and/or β proteins, as described herein.

In various embodiments, the invention provides a genetically modified non-human animal comprising in its genome, e.g., at its endogenous CD8 locus, at least one nucleotide sequence encoding a chimeric human/non-human CD8 polypeptide (e.g., CD8α and/or β polypeptide), wherein a human portion of the polypeptide comprises all or substantially all of an extracellular domain of a human CD8 (e.g., CD8α and/or β), wherein a non-human portion comprises at least transmembrane and cytoplasmic domains of a non-human CD8 (e.g., CD8α and/or β), and wherein the animal expresses the chimeric CD8 polypeptide (e.g., CD8α and/or β polypeptide). Thus, in one embodiment, the invention provides a genetically modified non-human animal comprising at its endogenous non-human CD8 locus a first nucleotide sequence encoding a chimeric human/non-human CD8α polypeptide and a second nucleotide sequence encoding a chimeric human/non-human CD8β polypeptide, wherein the first nucleotide sequence comprises a sequence that encodes all or substantially all of the extracellular domain of a human CD8α polypeptide and at least transmembrane and cytoplasmic domains of a non-human CD8α polypeptide, and wherein the second nucleotide sequence comprises a sequence that encodes all or substantially all of the extracellular domain of a human CD8β polypeptide and at least transmembrane and cytoplasmic domains of a non-human CDβ polypeptide, wherein the animal expresses a functional chimeric human/non-human CD8 protein. In one aspect, the non-human animal only expresses a humanized CD8 polypeptide (e.g., chimeric human/non-human CD8α and/or β polypeptide), and does not express a corresponding functional non-human CD8 polypeptide(s) from the endogenous CD8 locus.

In one embodiment, the chimeric human/non-human CD8α polypeptide comprises in its human portion all or substantially all of the extracellular domain of a human CD8α polypeptide. In one embodiment, the human portion of the chimeric CD8α polypeptide comprises at least the MHC I binding domain of the human CD8α polypeptide. In one embodiment, the human portion of the chimeric CD8α polypeptide comprises the sequence of at least all or substantially all of the immunoglobulin V-like domain of the human CD8α. In one embodiment, the nucleotide sequence encoding the human portion of the chimeric CD8α polypeptide comprises at least the exons that encode an extracellular domain of the human CD8α polypeptide. In one embodiment, the nucleotide sequence comprises at least the exons that encode the Ig V-like domains. In one embodiment, the extracellular domain of a human CD8α polypeptide is a region encompassing the domain of the polypeptide that is not transmembrane or cytoplasmic domain. In one embodiment, the nucleotide sequence encoding the chimeric human/non-human CD8α polypeptide comprises the sequence encoding a non-human (e.g., rodent, e.g., mouse) CD8α signal peptide. Alternatively, the nucleotide sequence may comprise the sequence encoding a human CD8α signal sequence. In one embodiment, the chimeric human/non-human CD8α polypeptide comprises an amino acid sequence set forth in SEQ ID NO:54, and the human portion of the chimeric polypeptide is set forth at amino acids 28-179 of SEQ ID NO:54 (represented separately in SEQ ID NO:59).

Similarly, in one embodiment, the chimeric human/non-human CD8β polypeptide comprises in its human portion all or substantially all of the extracellular domain of a human CD8β polypeptide. In one embodiment, the human portion of the chimeric CD8β polypeptide comprises the sequence of all or substantially all of the immunoglobulin V-like domain of CD8β. In one embodiment, the nucleotide sequence encoding the human portion of the chimeric CD8β polypeptide comprises at least the exons that encode the extracellular domain of the human CD8β polypeptide. In one embodiment, the human portion of the chimeric human/non-human CD8β polypeptide comprises at least the exons that encode the IgG V-like domain of CD8β. In one embodiment, the nucleotide sequence encoding the chimeric human/non-human CD8β polypeptide comprises the sequence encoding a non-human (e.g., rodent, e.g., mouse) CD8β signal peptide. Alternatively, the nucleotide sequence may comprise the sequence encoding a human CD8β signal sequence. In one embodiment, the chimeric human/non-human CD8β polypeptide comprises an amino acid sequence set forth in SEQ ID NO:53, and the human portion of the chimeric polypeptide is set forth at amino acids 15-165 of SEQ ID NO:53 (represented separately in SEQ ID NO:58).

In one embodiment, the non-human animal expresses a chimeric human/non-human CD8α and/or CD8β polypeptides. In some embodiments, the human portion of the chimeric human/non-human CD8α and/or β polypeptide comprises one or more conservative or nonconservative modification(s).

In one aspect, a non-human animal that expresses a human CD8α and/or β polypeptide sequence is provided, wherein the human CD8α and/or β polypeptide sequence is at least about 85%, 90%, 95%, 96%, 97%, 98%, or 99% identical to a human CD8α and/or β polypeptide sequence, respectively. In a specific embodiment, the human CD8α and/or β polypeptide sequence is at least about 90%, 95%, 96%, 97%, 98%, or 99% identical to the respective human CD8α and/or β polypeptide sequence described in the Examples. In one embodiment, the human CD8α and/or β polypeptide sequence comprises one or more conservative substitutions. In one embodiment, the human CD8α and/or β polypeptide sequence comprises one or more non-conservative substitutions.

In some embodiments, a portion, e.g., a human portion of the chimeric CD8, may comprise substantially all of the sequence indicated herein (e.g., substantially all of a protein domain indicated herein). Substantially all sequence generally includes 85%, 90%, 95%, 96%, 97%, 98%, or 99% of the amino acids believed to represent a particular portion of the protein (e.g., a particular functional domain, etc.). One skilled in the art would understand that the boundaries of a functional domain may vary slightly depending on the alignment and domain prediction methods used.

In one aspect, the non-human portion of the chimeric human/non-human CD8α and/or β polypeptide comprises at least transmembrane and/or cytoplasmic domain of the non-human CD8α and/or β polypeptide, respectively. Due to the important functions served by CD8 cytoplasmic domain, retention of the endogenous non-human (e.g., mouse) sequence in genetically engineered animals ensures preservation of proper intracellular signaling and other functions of the co-receptor. In one embodiment, the non-human animal is a mouse, and the non-human CD8α and/or β polypeptide is a mouse CD8α and/or β polypeptide, respectively. Although specific mouse CD8α and β sequences are described in the Examples, any suitable sequence derived therefrom, e.g., sequence comprising conservative/non-conservative amino acid substitutions, is encompassed herein. In one embodiment, the non-human animal (e.g., rodent, e.g., mouse) retains any endogenous sequence that has not been humanized.

The non-human animal described herein may comprise at its endogenous locus a nucleotide sequence encoding a chimeric human/non-human CD8α and/or β polypeptide. In one aspect, this results in a replacement of a portion of an endogenous CD8α gene with a nucleotide sequence encoding a portion of a human CD8α polypeptide, and/or a replacement of a portion of an endogenous CD8β gene with a nucleotide sequence encoding a portion of a human CD8β polypeptide. In one embodiment, such replacement is a replacement of endogenous nucleotide sequence encoding all or substantially all of extracellular domain of a non-human CD8α and/or β with a human nucleotide with a human nucleotide sequence encoding the same. In one embodiment, such replacement is a replacement of a sequence encoding at least all of substantially all of the immunoglobulin V-like domain of a non-human CD8α and/or β with a human nucleotide sequence encoding the same. In one embodiment, the replacement does not comprise a replacement of a CD8α and/or β sequence encoding transmembrane and cytoplasmic domain of a non-human CD8α and/or β polypeptide. Thus, the non-human animal expresses a chimeric human/non-human CD8α and/or β polypeptide from the endogenous non-human CD8 locus. In yet another embodiment, the replacement results in a CD8α and/or β protein comprising a polypeptide sequence set forth in SEQ ID NO:54 and/or 53, respectively.

In one embodiment, the nucleotide sequence of the chimeric human/non-human CD8 locus (e.g., chimeric rodent CD8 locus, e.g., chimeric mouse CD8 locus) is provided. In one aspect, because the chimeric human/non-human (e.g., human/rodent, e.g., human/mouse) CD8α and/or β sequence is placed at respective endogenous non-human (e.g., rodent, e.g., mouse) CD8α and/or β locus, it retains endogenous CD8α and/or β promoter and regulatory elements. In another embodiment, the chimeric locus may contain human CD8α and/or β promoter and regulatory elements to the extent those allow proper CD8α and/or β expression (proper spatial and temporal protein expression), CD8+ T cell development, CD8 lineage choice, and co-receptor function. Thus, in one aspect, the animals of the invention comprise a genetic modification that does not alter proper lineage choice and development of T cells. In one aspect, the animals (e.g., rodents, e.g., mice) of the invention do not express chimeric CD8 protein on immune cells other than cells that normally express CD8, e.g., animals do not express CD8 on B cells or CD4+ SP T cells. In one embodiment, the replacement results in retention of elements that allow proper spatial and temporal regulation of CD8α and/or β expression.

A genetically modified non-human animal comprising human or humanized CD8 polypeptides described herein may be selected from any animals that are described above in the section relating to humanized CD4 animals. In one embodiment, the non-human animal may be a rodent, e.g., a rat or a mouse.

Figure 3:
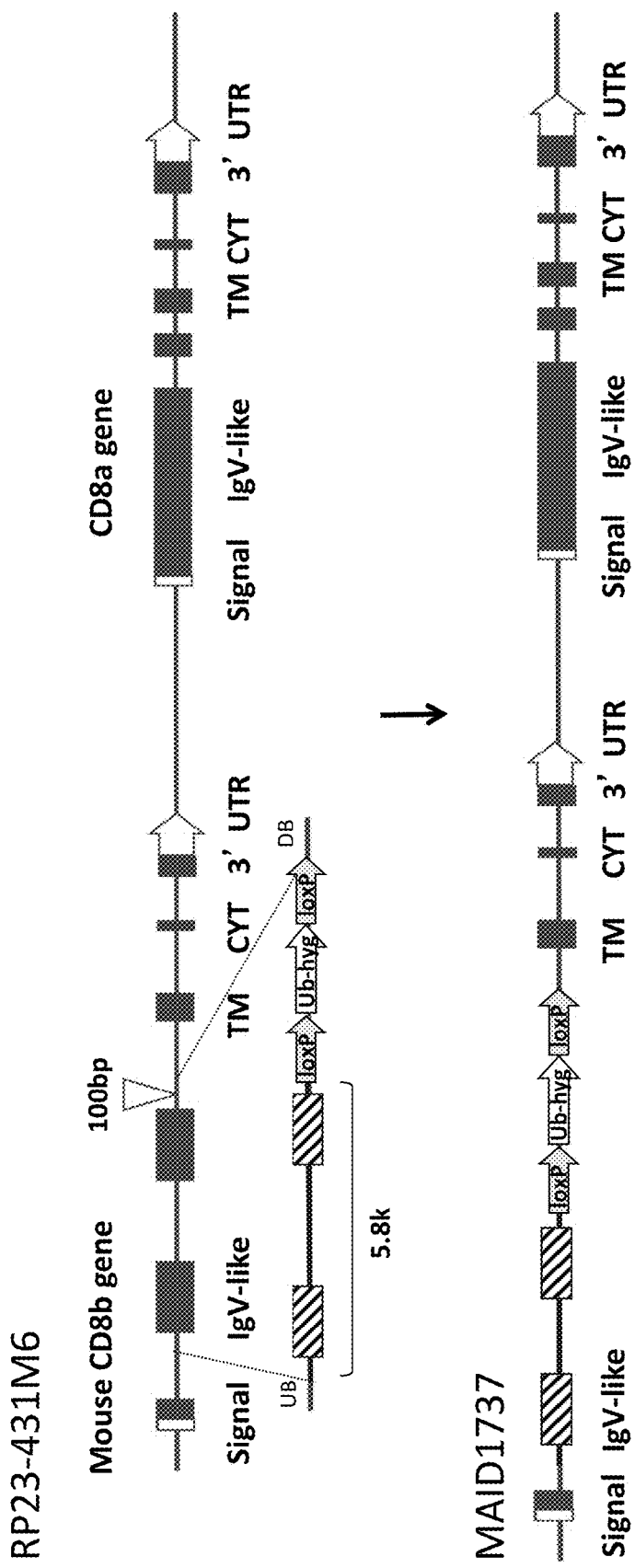
FIG. 3 is a schematic representation (not to scale) of the strategy for generating a humanized CD8b locus (MAID 1737) by replacement of mouse CD8β exons 2-3 with human CD8β exons 2-3. Mouse exon sequences are represented by filled rectangles, human exon sequences are represented by hashed rectangles.
Figure 4:
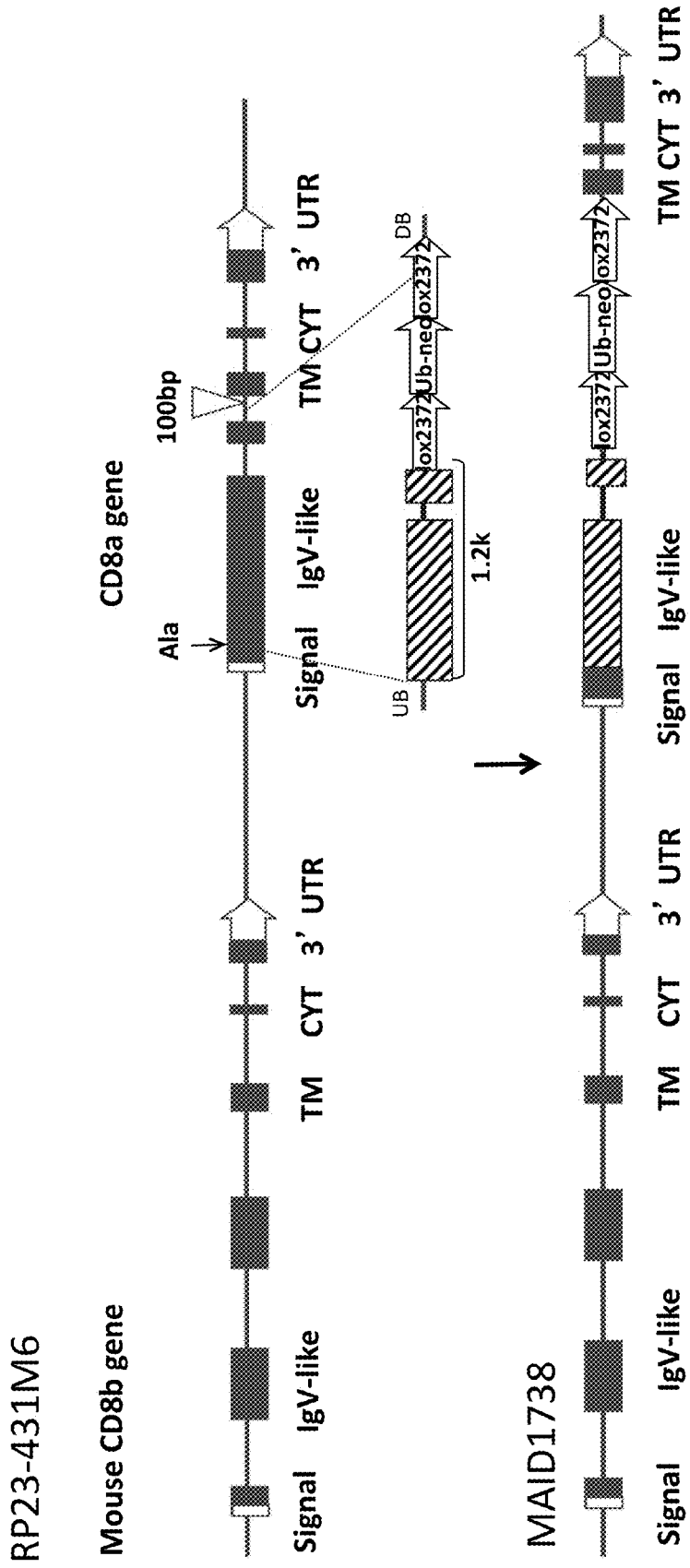
FIG. 4 is a schematic representation (not to scale) of the strategy for generating a humanized CD8a locus (MAID 1738) by replacement of a portion of mouse exon 1 and exon 2 with human exons 2-3, retaining the mouse leader sequence at the beginning of exon 1. Mouse exon sequences are represented by filled rectangles, human exon sequences are represented by hashed rectangles.
Figure 5:
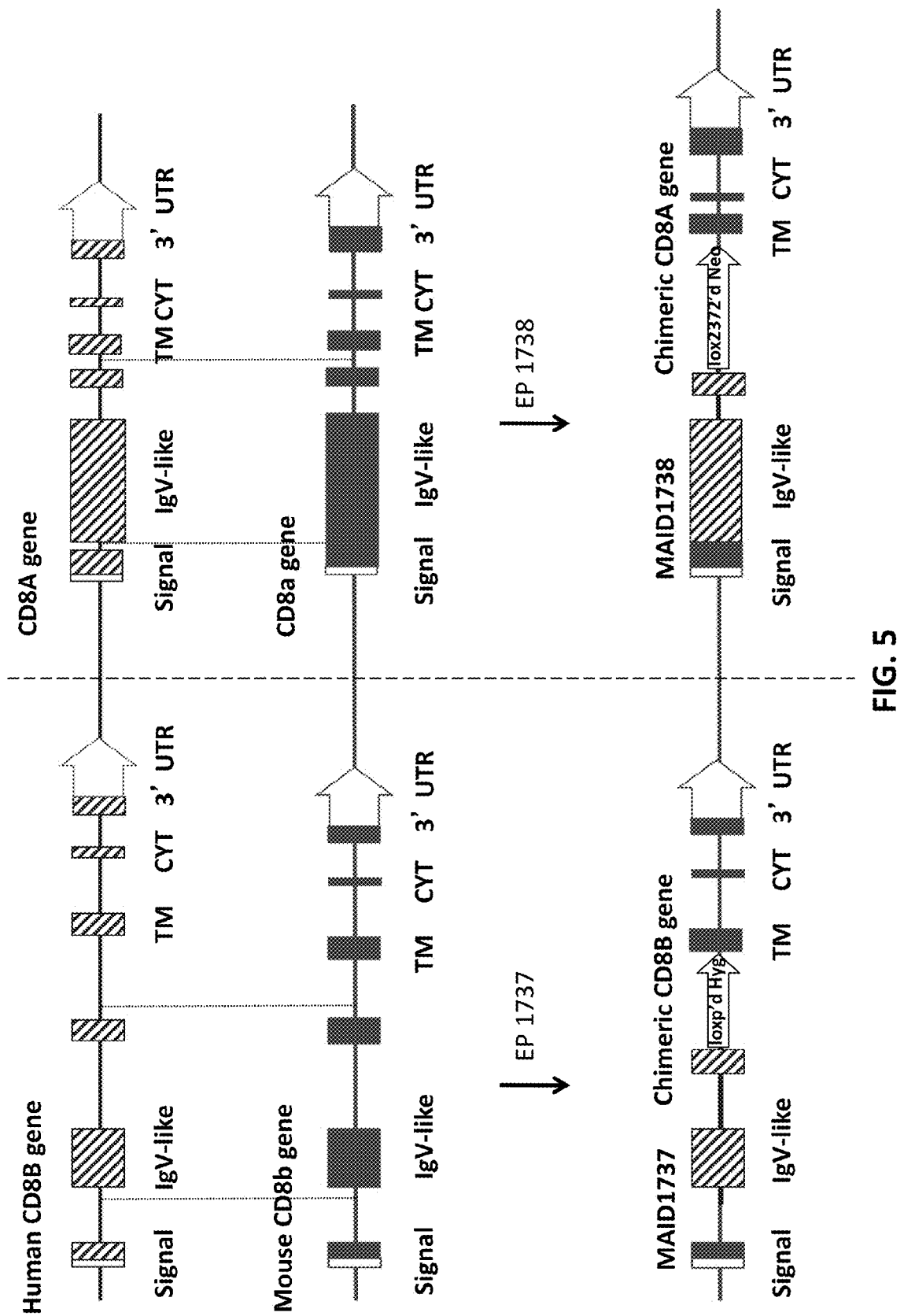
FIG. 5 is a schematic representation (not to scale) of the sequential targeting strategy to generate humanized loci comprising the sequence encoding humanized CD8b and CD8a genes. Mouse exon sequences are represented by filled rectangles, human exon sequences are represented by hashed rectangles.

Thus, in one embodiment, the invention provides a genetically modified mouse comprising in its genome, e.g., at its endogenous CD8 locus, a first nucleotide sequence encoding a chimeric human/mouse CD8α polypeptide and a second nucleotide sequence encoding a chimeric human/mouse CD8β polypeptide. In one embodiment, the first nucleotide sequence comprises a sequence that encodes all or substantially all of an extracellular domain of a human CD8α polypeptide and at least transmembrane and cytoplasmic domains of a mouse CD8α polypeptide, and the second nucleotide sequence comprises a sequence that encodes all or substantially all of an extracellular domain of a human CD8β polypeptide and at least transmembrane and cytoplasmic domains of a mouse CD8β polypeptide, and wherein the mouse expresses a functional chimeric human/mouse CD8 protein. In one embodiment, the first nucleotide sequence comprises a sequence that encodes at least the immunoglobulin V-like domain of the human CD8α polypeptide and the remaining sequences of a mouse CD8α polypeptide, and the second nucleotide sequence comprises a sequence that encodes at least the immunoglobulin V-like domain of the human CD8β polypeptide and the remaining sequences of a mouse CD8β polypeptide. In one embodiment, first nucleotide sequence comprises at least the MHC I-binding domain of a human CD8α polypeptide. In one embodiment, the first and the second nucleotide sequences comprise at least the exons that encode the extracellular domain of a human CD8α polypeptide and/or CD8β polypeptide, respectively. In one embodiment, the extracellular domain of a human CD8α polypeptide and/or CD8β polypeptide is a region encompassing the domain of the human CD8α polypeptide and/or CD8β polypeptide that is not transmembrane or cytoplasmic domain. In one embodiment, the domains of a human CD8α polypeptide are as schematically represented in FIGS. 4 and 5. In one embodiment, the domains of a human CD8β polypeptide are as schematically represented in FIGS. 3 and 5. In one embodiment, the nucleotide sequence encoding the chimeric human/mouse CD8α polypeptide and/or CD8β polypeptide comprises the sequence encoding a mouse CD8α and/or CD8β signal peptide, respectively. Alternatively, the nucleotide sequence may comprise the sequence encoding a human CD8α and/or CD8β signal sequence. In one embodiment, the mouse comprises a replacement of a nucleotide sequence encoding all or substantially all of the mouse CD8α and/or CD8β extracellular domain with a nucleotide sequence encoding all or substantially all of the human CD8α and/or CD8β extracellular domain, respectively.

In one embodiment, the mouse does not express a functional endogenous mouse CD8α and/or CD8β polypeptide from its endogenous CD8 locus. In one embodiment, the mouse as described herein comprises the chimeric human/mouse CD8 sequence in its germline.

In one aspect, the mouse expressing chimeric human/mouse CD8α and/or CD8β polypeptide retains mouse CD8α and/or CD8β promoter and regulatory sequences, e.g., the nucleotide sequence in the mouse encoding chimeric human/mouse CD8 is operably linked to endogenous mouse CD8 promoter and regulatory sequences. In one aspect, these regulatory sequences retained in the mouse include the sequences regulating CD8 protein expression at proper stages of T cell development. In one aspect, the genetically modified mouse does not express chimeric CD8 on B cells or T cells of CD4 lineage, or any cell, e.g., immune cell, that does not normally express endogenous CD8.

In various embodiments, a non-human animal (e.g., a rodent, e.g., a mouse or rat) that expresses a functional chimeric CD8 protein (e.g., CD8αβ or CD8αα) from a chimeric CD8 locus as described herein displays the chimeric protein on a cell surface. In one embodiment, the non-human animal expresses the chimeric CD8 protein on a cell surface in a cellular distribution that is the same as observed in a human. In one aspect, the CD8 protein of the invention is capable of interacting with an MHC I protein expressed on the surface of a second cell.

In one embodiment, the non-human animal (e.g., rodent, e.g., mouse) of the invention further comprises a nucleotide sequence encoding a human or humanized MHC I protein, such that the chimeric CD8 protein expressed on the surface of a T cell of the animal is capable of interacting with a human or humanized MHC I expressed on a surface of a second cell, e.g., an antigen presenting cell. In one embodiment, the MHC I protein comprises an extracellular domain of a human MHC I polypeptide. In one embodiment, the animal further comprises a human or humanized β-2 microglobulin polypeptide. Exemplary genetically modified animals expressing a human or humanized MHC I polypeptide and/or β-2 microglobulin polypeptide are described in U.S. patent application Ser. No. 13/661,159, filed Oct. 26, 2012, and U.S. patent application Ser. No. 13/793,812, filed Mar. 11, 2013, both incorporated herein by reference in their entireties. Thus, in one embodiment, the animal comprising chimeric CD8 protein described herein may further comprise a humanized MHC I complex, wherein the humanized MHC I complex comprises: (1) a humanized MHC I polypeptide, e.g., wherein the humanized MHC I polypeptide comprises a human MHC I extracellular domain and transmembrane and cytoplasmic domains of an endogenous (e.g., mouse) MHC I, e.g., wherein the humanized MHC I comprises α1, α2, and α3 domains of a human MHC I polypeptide, and (2) a human or humanized β2 microglobulin polypeptide (e.g., the animal comprises in its genome a nucleotide sequence set forth in exons 2, 3, and 4 of a human β2 microglobulin). In one aspect, both humanized MHC I and human or humanized β2 microglobulin polypeptides are encoded by nucleotide sequences located at endogenous MHC I and β2 microglobulin loci, respectively; in one aspect, the animal does not express functional endogenous MHC I and β2 microglobulin polypeptides. Thus, the MHC I expressed by the animals may be a chimeric human/non-human, e.g., human/rodent (e.g., human/mouse) MHC I polypeptide. A human portion of the chimeric MHC I polypeptide may be derived from a human HLA class I protein selected from the group consisting of HLA-A, HLA-B, and HLA-C, e.g., HLA-A2, HLA-B27, HLA-B7, HLA-Cw6, or any other HLA class I molecule present in a human population. In the embodiment, wherein the animal is a mouse, a non-human (i.e., a mouse) portion of the chimeric MHC I polypeptide may be derived from a mouse MHC I protein selected from H-2D, H-2K and H-2L. In one aspect, the non-human animal comprising the chimeric human/non-human CD8 described herein and the humanized MHC I and/or β-2 microglobulin described in U.S. patent application Ser. Nos. 13/661,159 and 13/793,812 may be generated by breeding an animal comprising a chimeric CD8 locus (e.g., chimeric CD8α and/or β locus) as described herein with an animal comprising a humanized MHC I and/or β-2 microglobulin locus. The animal may also be generated by introducing into ES cells of an animal comprising humanized MHC I and/or β-2 microglobulin locus a nucleotide sequence encoding chimeric CD8 (e.g., chimeric CD8α and/or β), e.g., for replacement at the endogenous CD8 locus (e.g., chimeric CD8α and/or β locus); or introducing into ES cells of an animal comprising a chimeric CD8 locus (e.g., chimeric CD8α and/or β locus) a nucleotide sequence(s) encoding humanized MHC I and/or β-2 microglobulin.

In addition to a genetically engineered non-human animal, a non-human embryo (e.g., a rodent, e.g., a mouse or a rat embryo) is also provided, wherein the embryo comprises a donor ES cell that is derived from a non-human animal (e.g., a rodent, e.g., a mouse or a rat) as described herein. In one aspect, the embryo comprises an ES donor cell that comprises the chimeric CD8 gene, and host embryo cells.

Also provided is a tissue, wherein the tissue is derived from a non-human animal (e.g., a rodent, e.g., a mouse or a rat) as described herein, and expresses the chimeric CD8 protein.

In addition, a non-human cell isolated from a non-human animal as described herein is provided. In one embodiment, the cell is an ES cell. In one embodiment, the cell is a T cell, e.g., a CD8+ T cell. In one embodiment, the cell is a cytotoxic T cell.

Also provided is a non-human cell comprising a chromosome or fragment thereof of a non-human animal as described herein. In one embodiment, the non-human cell comprises a nucleus of a non-human animal as described herein. In one embodiment, the non-human cell comprises the chromosome or fragment thereof as the result of a nuclear transfer.

In one aspect, a non-human induced pluripotent cell comprising gene encoding a chimeric CD8 polypeptide (e.g., CD8α and/or CD8β polypeptide) as described herein is provided. In one embodiment, the induced pluripotent cell is derived from a non-human animal as described herein.

In one aspect, a hybridoma or quadroma is provided, derived from a cell of a non-human animal as described herein. In one embodiment, the non-human animal is a mouse or rat.

In one aspect, an in vitro preparation is provided that comprises a T cell that bears a chimeric CD8 protein on its surface and a second cell that binds the chimeric CD8. In one embodiment, the second cell is a cell expressing an MHC I polypeptide, e.g., a chimeric human/non-human MHC I protein. In one embodiment, the chimeric CD8 on the surface of the first cell interacts with chimeric MHC I on the surface of the second cell. In one embodiment, the chimeric CD8 protein retains interaction with endogenous cytosolic molecules, e.g., endogenous cytosolic signaling molecules (e.g., endogenous Lck, etc.).

Also provided herein is a method for making a genetically engineered non-human animal described herein. The method results in an animal that comprises at an endogenous CD8 locus a nucleotide sequence(s) encoding a chimeric human/non-human CD8α and/or CD8β polypeptide. The method may utilize a targeting construct made using VELOCIGENE® technology, introducing the construct into ES cells, and introducing targeted ES cell clones into a mouse embryo using VELOCIMOUSE® technology, as described in the Examples.

In one embodiment, the invention provides a method of modifying a CD8 locus of a non-human animal to express a chimeric human/non-human CD8 polypeptide described herein. In one aspect, provided is a method of modifying a CD8 locus of a mouse to express a chimeric human/mouse CD8 polypeptide comprising replacing at an endogenous CD8 locus of a mouse a nucleotide sequence encoding an endogenous mouse CD8 polypeptide with a nucleotide sequence encoding a chimeric human/mouse CD8 polypeptide. The CD8 polypeptide may be selected from CD8α, CD8β, and combination thereof. In one aspect, the chimeric polypeptide comprises all or substantially all of an extracellular domain of a human CD8 polypeptide and at least transmembrane and cytoplasmic domains of an endogenous mouse CD8 polypeptide.

Thus, a nucleotide construct for generating genetically modified animals described herein is also provided. In one aspect, the sequence of the nucleotide construct comprises 5' and 3' homology arms, a DNA fragment comprising human CD8α or CD8β sequence, and a selection cassette flanked by recombination sites. In some embodiments, the human sequence comprises introns and exons of human CD8α or CD8β, e.g., exons encoding the extracellular domain of the human CD8α or CD8β, respectively. In one embodiment, homology arms are homologous to non-human CD8α or CD8β sequence. Exemplary constructs for CD8α and CD8β are depicted in FIGS. 4 and 3, respectively.

Because of close chromosomal localization of the genes encoding CD8α and CD8β, sequential targeting of the two genes improves the chances of successful humanization. In one embodiment, the targeting strategy comprises introducing chimeric CD8β construct described herein into ES cells, generating a mouse from the targeted ES cells, deriving genetically modified ES cells from said mouse, and introducing chimeric CD8α construct described herein into said genetically modified ES cells. In another embodiment, the targeting strategy comprises introducing a chimeric CD8β construct described herein into ES cells, selecting the cells that have incorporated the chimeric CD8β construct, introducing a chimeric CD8α construct described herein into ES cells that have incorporated and are harboring the chimeric CD8β construct, and selecting the cells that have incorporated both chimeric CD8β and CD8α. In one aspect of this embodiment, the steps of selecting are performed utilizing different selection markers. In alternative embodiments, CD8α humanization can be accomplished first. Upon completion of gene targeting, ES cells of genetically modified non-human animals can be screened to confirm successful incorporation of exogenous nucleotide sequence of interest or expression of exogenous polypeptide by a variety of methods (e.g., methods described above for CD4 humanization, e.g., modification of allele assay described in Valenzuela et al., supra).

In one aspect, a method for making a chimeric human/non-human CD8 molecule (e.g., CD8α and/or CD8β) is provided, comprising expressing in a single cell a chimeric CD8 polypeptide(s) from a nucleotide construct(s) as described herein. In one embodiment, the nucleotide construct is a viral vector; in a specific embodiment, the viral vector is a lentiviral vector. In one embodiment, the cell is selected from a CHO, COS, 293, HeLa, and a retinal cell expressing a viral nucleic acid sequence (e.g., a PERC.6™ cell).

In one aspect, a cell that expresses a chimeric CD8 protein is provided. In one embodiment, the cell comprises an expression vector comprising a chimeric CD8 sequence(s) as described herein. In one embodiment, the cell is selected from CHO, COS, 293, HeLa, and a retinal cell expressing a viral nucleic acid sequence (e.g., a PERC.6™ cell).

A chimeric CD8 molecule made by a non-human animal as described herein is also provided, wherein the chimeric CD8 molecule comprises all or substantially all of the extracellular domain from a human CD8 protein (e.g., CD8α and/or CD8β), and at least transmembrane and cytoplasmic domains from a non-human CD8 protein, e.g., mouse CD8 protein. Exemplary chimeric CD8α polypeptide is set forth in SEQ ID NO:54, and exemplary chimeric CD8β protein is set forth in SEQ ID NO:53.

Use of Genetically Modified CD4 and CD8 Animals

The genetically modified non-human animals, e.g., rodents, e.g., mice or rats, comprising either humanized CD4 and MHC II or humanized CD8 and MHC I, present peptides to T cells (CD4+ or CD8+ T cells, respectively) in a human-like manner, because substantially all of the components of the complex are human or humanized. The genetically modified non-human animals of the invention can be used to study the function of a human immune system in the humanized animal; for identification of antigens and antigen epitopes that elicit immune response (e.g., T cell epitopes, e.g., unique human cancer epitopes), e.g., for use in vaccine development; for identification of high affinity T cells to human pathogens or cancer antigens (i.e., T cells that bind to antigen in the context of human MHC I complex with high avidity), e.g., for use in adaptive T cell therapy; for evaluation of vaccine candidates and other vaccine strategies; for studying human autoimmunity; for studying human infectious diseases; and otherwise for devising better therapeutic strategies based on human MHC and CD4/CD8 expression.

Thus, in various embodiments, the genetically engineered animals of the present invention are useful, among other things, for evaluating the capacity of an antigen to initiate an immune response in a human, and for generating a diversity of antigens and identifying a specific antigen that may be used in human vaccine development.

In one aspect, a method for determining whether a peptide will provoke a cellular immune response in a human is provided, comprising exposing a genetically modified non-human animal as described herein to the peptide, allowing the non-human animal to mount an immune response, and detecting in the non-human animal a cell (e.g., a CD8+ or CD4+ T cell, comprising a human CD8 or CD4, respectively) that binds a sequence of the peptide presented by a chimeric human/non-human MHC I or II molecule as described herein. In one embodiment, the non-human animal following exposure comprises an MHC class I-restricted CD8+ cytotoxic T lymphocyte (CTL) that binds the peptide. In another embodiment, the non-human animal following exposure comprises an MHC II-restricted CD4+ T cell that binds the peptide.

In one aspect, a method for identifying a human T cell epitope is provided, comprising exposing a non-human animal as described herein to an antigen comprising a putative T cell epitope, allowing the non-human animal to mount an immune response, isolating from the non-human animal an MHC class I- or MHC class II-restricted T cell that binds the epitope, and identifying the epitope bound by said T cell.

In one aspect, a method is provided for identifying an antigen that generates a T cell response in a human, comprising exposing a putative antigen to a mouse as described herein, allowing the mouse to generate an immune response, and identifying the antigen bound by the HLA class I- or class II-restricted molecule.

In one aspect, a method is provided for determining whether a putative antigen contains an epitope that upon exposure to a human immune system will generate an HLA class I- or class II-restricted immune response, comprising exposing a mouse as described herein to the putative antigen and measuring an antigen-specific HLA class I- or HLA class II-restricted immune response in the mouse.

In addition, the genetically engineered non-human animals described herein may be useful for identification of T cell receptors, e.g., high-avidity T cell receptors, that recognize an antigen of interest, e.g., a tumor or another disease antigen. The method may comprise: exposing the non-human animal described herein to an antigen, allowing the non-human animal to mount an immune response to the antigen, isolating from the non-human animal a T cell comprising a T cell receptor that binds the antigen presented by a human or humanized MHC I or MHC II, and determining the sequence of said T cell receptor.

In one embodiment, a method is provided for determining T cell activation by a putative human therapeutic, comprising exposing a genetically modified animal as described herein to a putative human therapeutic (or e.g., exposing a human or humanized MHC II- or MHC I-expressing cell of such an animal to a peptide sequence of the putative therapeutic), exposing a cell of the genetically modified animal that displays a human or humanized MHC/peptide complex to a T cell comprising a chimeric human/non-human (e.g., human/mouse) CD4 or CD8 capable of binding the cell of the genetically modified animal, and measuring activation of the T cell that is induced by the peptide-displaying cell of the genetically modified animal.

In addition to the ability to identify antigens and antigen epitopes from human pathogens or neoplasms, the genetically modified animals of the invention can be used to identify autoantigens of relevance to human autoimmune diseases, e.g., type I diabetes, multiple sclerosis, etc. Also, the genetically modified animals of the invention can be used to study various aspects of human autoimmune disease, and may be utilized as autoimmune disease models.

Other uses of the genetically modified animals described herein, i.e., animals comprising a human or humanized T cell co-receptor (e.g., chimeric human/non-human CD4 or CD8), optionally further comprising a human or humanized MHC II or I protein, will be apparent from the present disclosure.

EXAMPLES

The invention will be further illustrated by the following nonlimiting examples. These Examples are set forth to aid in the understanding of the invention but are not intended to, and should not be construed to, limit its scope in any way. The Examples do not include detailed descriptions of conventional methods that would be well known to those of ordinary skill in the art (molecular cloning techniques, etc.). Unless indicated otherwise, parts are parts by weight, molecular weight is average molecular weight, temperature is indicated in Celsius, and pressure is at or near atmospheric.

Example 1. Construction and Characterization of Genetically Modified CD4 Mice

Example 1.1: Engineering a Chimeric CD4 Locus

Mouse CD4 locus was humanized in a single step by construction of a unique targeting vector from human and mouse bacterial artificial chromosome (BAC) DNA using VELOCIGENE® technology (see, e.g., U.S. Pat. No. 6,586,251 and Valenzuela et al. (2003) High-throughput engineering of the mouse genome coupled with high-resolution expression analysis. Nat. Biotech. 21(6): 652-659). To generate the targeting vector, a series of bacterial homologous recombinations (BHRs) using Bacterial Artificial Chromosome (BAC) DNA, as well as other engineering steps, were carried out.

Briefly, four DNA fragments (1) fragment containing mouse signal peptide (encoded by exons 2 and 3 of mouse CD4 gene), (2) fragment containing human exon 3 downstream of mouse signal peptide, (3) fragment containing SPEC resistance cassette flanked by Asc I and PI-SceI sites, and (4) fragment containing 160 bp of mouse CD4 intron 6 (intron between exons 6 and 7), which started about 200 bp downstream of mouse CD4 exon 6 were joined by infusion ligation (Clonetech). The resulting DNA fragment contained, from 5' to 3': mouse exon 2, mouse intron 2, portion of mouse exon 3 containing signal peptide, human exon 3 downstream of human signal peptide, portion of human intron 3, SPEC cassette, portion of mouse intron 6. This DNA fragment was used in BHR to modify mouse BAC clone BMQ391F08 in order to delete mouse sequence encoding mouse CD4 Ig-like domains 1-3 and to introduce exon 3 of human CD4. The CM cassette of the BAC was substituted for SPEC cassette resulting in the first BAC vector (FIG. 1, top diagram).

Human BAC RP11-101F21 was modified by BHR to introduce AscI-LoxP-PGK-neo-loxP cassette 60 bp downstream of human exon 3, and to introduce PI-SceI restriction site and SPEC cassette about 100 bp downstream of exon 6, resulting in the second BAC vector (FIG. 1, middle diagram). This step was followed by BAC to BAC ligation of the first and the second BAC vectors after digestion with AscI and PI-SceI restriction enzymes to generate the CD4 targeting vector (FIG. 1, bottom diagram). The upstream and downstream junctions of the mouse-human and human-mouse sequences, respectively, are listed in Table 1 below and set forth in the Sequence Listing. The sequence across the human intron 3-lox-neo cassette junction (5' end of the cassette) is set forth in SEQ ID NO:55, and the sequence across lox-neo cassette-human intron 3 junction (3' end of the cassette) is set forth in SEQ ID NO:56; both sequences are also listed in Table 1. The complete nucleic acid sequence of the humanized CD4 piece, including the pgk-neo cassette depicted in FIG. 1 is set forth in SEQ ID NO:3. The pgk-neo cassette is spans residues 307-2176 of SEQ ID NO:3, the two lox sites are located at resides 267-300 and 2182-2215, while the human sequence spans residues 1-234 and 2222-18263. The amino acid sequence of complete humanized CD4 protein is set forth in SEQ ID NO:4, with human sequence spanning amino acids 27-319 (set forth in SEQ ID NO:57).

TABLE 1

| Junction Sequences of the Chimeric CD4 Targeting Vector | | |
|---|---|---|
| Junction | Sequence | SEQ ID NO |
| 5' mouse/<br>human junction | AGGGGAAACCCGCAAAGGATGGGACATAGGGAGACAGCTGTTAACAT<br>CTGAAACATGACCTTCTTTTCTGTGCAGCACAACTCCTAGCTGTCAC<br>TCAAGGG(AAGAAAGTGGTGCTGGGCAAAAAAGGGGATACAGTGGAA<br>CTGACCTGTACAGCTTCCCAGAAGAAGAGCATACAATTCCACTGGAA<br>AAACTCCAACCAGAT) | 1 |
| 3' human/<br>mouse junction | (CTGGTCACCTGGATGAAGTGAGGGAGGGCCCTCTGGGTTTGGGGCT<br>GGTTTTGAACTGAGACATCCATGAGCCAGCCTGGGGCTGGCTTCACT<br>GAAGATC)ATCTATGTCGGGTGCGGAGAAAGAGGTAATGAAATGGCA<br>CATGCTATGTACAAACTCTATTGCTGAGCAGCACCCAGTCCTGAGCT<br>GGCTCTGAATTGAGGGTGAAATTCACACATTCTCCCCCAACATCTAT<br>AATCTGG | 2 |

TABLE 1-continued

Junction Sequences of the Chimeric CD4 Targeting Vector

| Junction | Sequence | SEQ ID NO |
|---|---|---|
| Human/5' lox site | (TATGGAGTGAAAGCCTTTGGTGTCTGAGATCTGGTCTTAGTTAAAC TCTGGGATC) *GGCGCGCCGAATTCCTGCAGCCCGGGCTCGAGATAAC TTCGTATAATGTATGCTATACGAAGTTATATGCATCCGGGTAGGGGA GGCGCTTTTCCC* | 55 |
| 3' lox site/human | *AGTATTGTTTTGCCAAGTTCTAATTCCATCAGACCTCGACCTGCAGC CCTAGATAACTTCGTATAATGTATGCTATACGAAGTTATCCTAGG* (C CAGAGGGCTTGGGTTGACAGAAACTCAGTGGCATTCTTATCCAGAGT TTCTCTACACC) | 56 |

Human sequences are in parenthesis and sequence containing restriction enzyme site (PI-Sce I) is bolded. Selection cassette sequences are italicized.

The human CD4 Targeting Vector was linearized with NotI and electroporated into F1H4 mouse ES cells. Targeted ES cells bearing a humanized CD4 locus were identified by genotyping using a modification of allele assay (Valenzuela et al.) that detected the presence of the neomycin cassette and the human CD4 gene, as well as one copy of the mouse CD4 gene. Primers and probes used in the assay are depicted in Table 2 and set forth in the Sequence Listing.

TABLE 2

Primers and Probes for Genotyping Chimeric CD4

| Region Detected | Assay | 5' primer | 3' primer | Probe |
|---|---|---|---|---|
| Mouse CD4 intron 3 (1765m2) | LOA | GAAGTGGGTGTGCC ATTCAGA (SEQ ID NO: 5) | AAAGCTCAGAAGCA GACAGAGTCA (SEQ ID NO: 6) | TTCCAAAAGCCTACA GCAGGCCCAG (SEQ ID NO: 7) |
| Mouse CD4 intron 5 (1765m4) | LOA | TCATCTCCCCTTCC TGAACCT (SEQ ID NO: 8) | CCCAGCCACAAGAA GAAGAAA (SEQ ID NO: 9) | CTTCCCCCGCATCCA TTTTTCTGTTC (SEQ ID NO: 10) |
| Human CD4 intron between exons 3 and 4 (downstream of pgk-neo) (1765h1) | GOA | GGTCTCGAACTCAT GAGCTCAA (SEQ ID NO: 11) | GGCATAGTGACACA CACCTGTAATT (SEQ ID NO: 12) | TGATCCACTCACCTT GGCCTCTCAGAG (SEQ ID NO: 13) |
| Human CD4 intron between exons 5 and 6 (1765h2) | GOA | GTCAGGGAGCTTAC TTTCTTTGTTG (SEQ ID NO: 14) | TGTTAGTGTCCCTG AGTAAGTGGATT (SEQ ID NO: 15) | CTCAGCTCCACACCC CTACCAAGTTGG (SEQ ID NO: 16) |

Floxed neomycin resistance cassette was removed by electroporation of plasmid expressing Cre recombinase into ES cells containing humanized CD4 locus.

Targeted ES cells bearing a humanized CD4 locus without resistance marker were identified by genotyping that detected absence of the neomycin cassette, the presence of one copy of the human CD4 gene and one copy of the mouse CD4 gene.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing a chimeric CD4 gene were identified by genotyping using a modification of allele assay (Valenzuela et al., supra) that detects the presence of the unique human CD4 gene sequences.

Example 1.2: Expression of Chimeric CD4 in Genetically Engineered Mice

Figure 2:
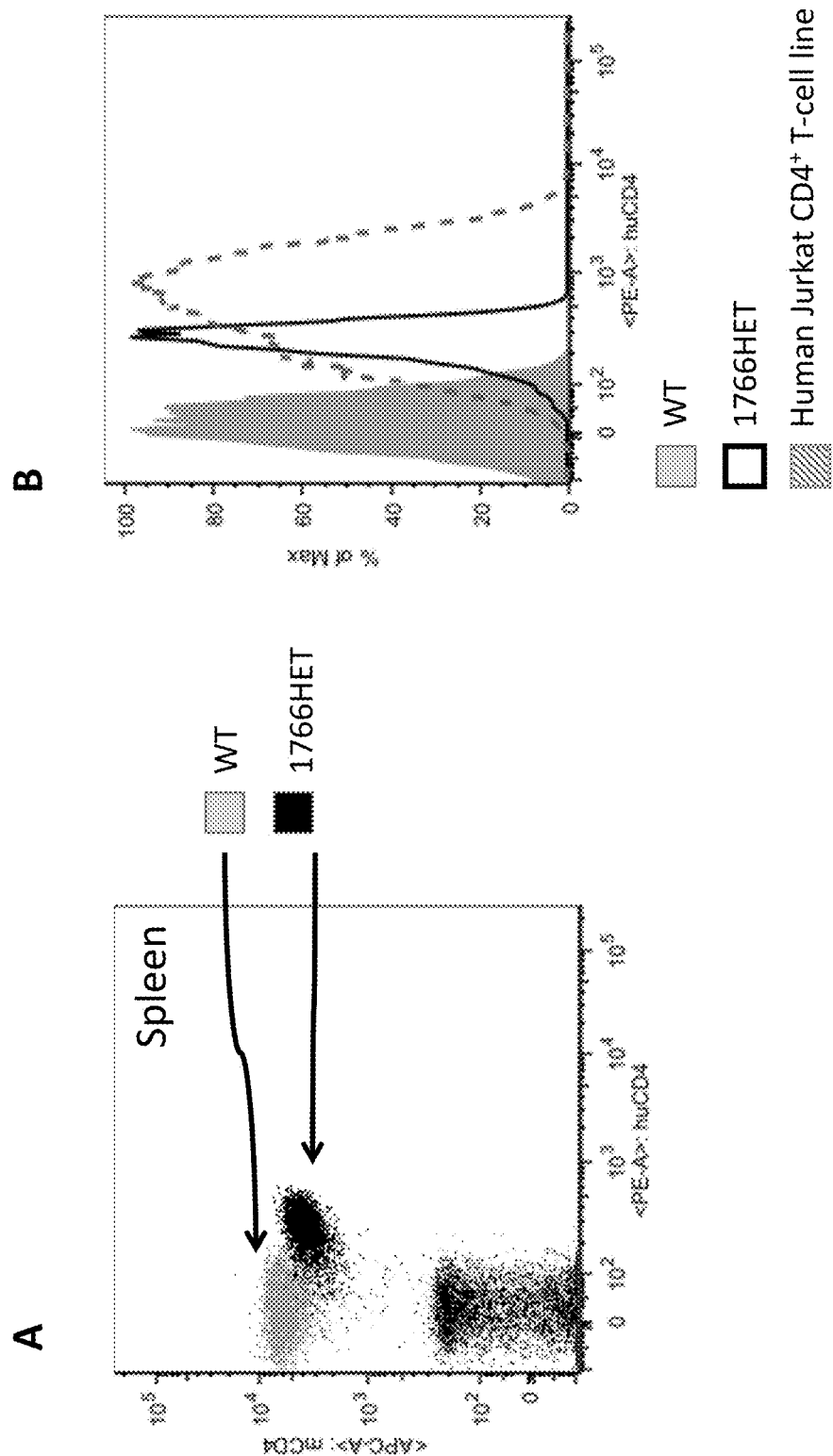
FIG. 2 shows FACS analysis with anti-human CD4 and anti-mouse CD4 antibodies of splenocytes derived from WT mouse or mouse heterozygous for human CD4 (1766HET) (A); and FACS analysis of T cells derived from WT mouse vs. 1766HET mouse vs. Jurkat human CD4 T cell line.

Spleens from WT or heterozygous humanized CD4 mice ("1766HET") were perfused with Collagenase D (Roche Bioscience) and erythrocytes were lysed with ACK lysis buffer. Cell surface expression of human CD4 or mouse CD4 was analyzed by FACS using either anti-human CD4 or anti-mouse CD4 antibodies, respectively. As depicted in FIGS. 2A and 2B, human CD4 is expressed on the surface of T cells obtained from mice heterozygous for humanized CD4 described herein.

Example 2. Construction and Characterization of Genetically Modified CD8 Mice CD8 protein occurs as either a disulfide-linked homodimer (e.g., CD8α homodimer) or homomultimer of two subunits or as a heterodimer of two proteins, CD8α (CD8α)

and CD8β (CD8b). CD8α and CD8β genes are colocalized in the genome, e.g., on mouse chromosome 6, they are located about 37 kb away from each other. Such close linkage makes it very difficult to generate a genetically modified mouse comprising humanizations at both CD8α and CD8β loci by breeding. Therefore, sequential targeting, by first introducing one gene, e.g., CD8β, followed by introduction of the second gene, e.g., CD8α, is performed.

Example 2.1: Engineering a Chimeric CD8β Locus

Mouse CD8b locus was humanized in a single step by construction of a unique targeting vector from mouse bacterial artificial chromosome (BAC) DNA using VELOCIGENE® technology (see, e.g., U.S. Pat. No. 6,586,251 and Valenzuela et al. (2003) High-throughput engineering of the mouse genome coupled with high-resolution expression analysis. Nat. Biotech. 21(6): 652-659). DNA from BAC RP23-431M6 was modified by BHR to generate a large targeting vector (LTVEC), MAID 1737, to contain a replacement of mouse exons 2-3 encoding the CD8 ecto domain (from the 5' junction in intron 1 to the 3' junction in intron 3), with homologous human sequences (FIG. 3). A loxp-Ub-Hyg cassette was inserted at the 3' junction in intron 3. The nucleotide sequence at various junctions of the resulting vector are listed in Table 3 and set forth in Sequence Listing. The complete amino acid sequence of humanized CD8β protein is set forth in SEQ ID NO:53; with human sequences spanning amino acids 15-165 (set forth in SEQ ID NO:58).

TABLE 3

Junction Sequences of the Chimeric CD8β Targeting Vector

| Junction | Sequence | SEQ ID NO |
|---|---|---|
| Mouse/human in intron 1 | TGTTTGCCTGTGACATGAACTCATTGTGACACAAACCACTGTGC TAGGGGGATCCACTAGTAACGGCCGCCAGTGTGCTGGAATTCG CCC(TCGCAAGGGCCAGGCATATAAGTACACAATAAACAAATGG CAGCTCTCTCC) | 17 |
| Human/5' of lox site in intron 3 | (CCCCTCCTTCCTTCCCCAGGCACTTTCCAAGTGTCAACTCTAG AGCCTAT)CGCGGCCGCACCGGT*ATAACTTCGTATAATGTATGC TATACGAAGTTAT* | 18 |
| 3' of lox site/mouse in intron 3 | *ATAACTTCGTATAATGTATGCTATACGAAGTTAT*GTCGACGTAG CCTATTTCTCTAGATCCAAAATGATGACAACAAAAGGTACCTTG TG | 19 |

Human sequences are in parenthesis, lox sites are italicized, and restriction enzyme sites, multiple cloning sites, and vector-derived sequences are bolded.

Targeting vector was electroporated into F1H4 mouse ES cells (FIG. 5, left side). Targeted ES cells bearing a humanized CD8b locus were identified by genotyping using a modification of allele assay (Valenzuela et al.) that detected the presence of the human CD8b gene. Primers and probes used in the assay are depicted in Table 4 and set forth in the Sequence Listing.

TABLE 4

Primers and Probes for Genotyping Chimeric CD8β

| Region Detected | Assay | 5' primer | 3' primer | Probe |
|---|---|---|---|---|
| Mouse exon 2 | LOA | GCAGCTCTGCCCTCATTC AG (SEQ ID NO: 20) | CATCTTTGCCGTAT GGTTGGT (SEQ ID NO: 21) | CCCCTTCGTCCCTGC TGGTTCA (SEQ ID NO: 22) |
| Mouse exon 3 | LOA | CAAGAAGACTACCCTGAA GATGAAGA (SEQ ID NO: 23) | TGTGAGTGCAACAA TGGAAAACT (SEQ ID NO: 24) | CGTTCCCCCACCCAG AGACCCA (SEQ ID NO: 25) |
| Human exon 2 | GOA | GGCACCGAGCAGTGACAG T (SEQ ID NO: 26) | TTCACCGTGGATAG TCCCTTTT (SEQ ID NO: 27) | AGTTCCTGGCCCTCT GGGATTCCG (SEQ ID NO: 28) |
| Human exon 3 | GOA | TTGCTTTCTTTCTGTAGT TGATTTCC (SEQ ID NO: 29) | CCGGCACACTCTCT TCTTGAG (SEQ ID NO: 30) | TCCCACCACTGCCCA GCCCA (SEQ ID NO: 31) |
| Hyg | GOA | TGCGGCCGATCTTAGCC (SEQ ID NO: 32) | TTGACCGATTCCTT GCGG (SEQ ID NO: 33) | ACGAGCGGGTTCGGC CCATTC (SEQ ID NO: 34) |

LOA = loss of allele; GOA = gain of allele.

Targeted ES cells described above were used as donor ES cells and introduced into an 8-cell stage mouse embryo by the VELOCIMOUSE® method (see, e.g., U.S. Pat. No. 7,294,754 and Poueymirou et al. (2007) F0 generation mice that are essentially fully derived from the donor gene-targeted ES cells allowing immediate phenotypic analyses Nature Biotech. 25(1):91-99). VELOCIMICE® (F0 mice fully derived from the donor ES cell) independently bearing a chimeric CD8b gene were identified by genotyping using a modification of allele assay (Valenzuela et al., supra) that detects the presence of the unique human CD8b gene sequences.

The selection cassette may be removed by methods known by the skilled artisan. For example, ES cells bearing the chimeric human/mouse CD8b locus may be transfected with a construct that expresses Cre in order to remove the "loxed" hygromycin cassette introduced by the insertion of the targeting construct containing human CD8b gene sequences. The hygromycin cassette may optionally be removed by breeding to mice that express Cre recombinase. Optionally, the hygromycin cassette is retained in the mice. In one embodiment, the cassette was deleted to generate MAID 1739.

Example 2.2: Engineering a Chimeric CD8α Locus

Mouse CD8α locus was humanized in a single step by construction of a unique targeting vector from mouse bacterial artificial chromosome (BAC) DNA using VELOCIGENE® technology (see, e.g., U.S. Pat. No. 6,586,251 and Valenzuela et al., supra). DNA from BAC RP23-431M6 was modified by BHR to generate a large targeting vector (LTVEC), MAID 1738, to contain a replacement of mouse exons 1-2 encoding the CD8α ecto domain (from the 5' junction at Ala codon 27 in mouse exon 1 to the 3' junction in mouse intron 2), with the homologous human sequences (from the 5' junction in human exon 2 to the 3' junction in intron 3 (FIG. 4)). This retains the mouse leader sequence at the beginning of exon 1. A lox2372-Ub-Neo cassette was inserted at the 3' junction of human/mouse sequences. The nucleotide sequences at various junctions of the resulting vector are listed in Table 5 and set forth in Sequence Listing. The complete amino acids sequence of humanized CD8α polypeptide is set forth in SEQ ID NO:54, with human sequence spanning amino acids 28-179 (set forth in SEQ ID NO:59).

TABLE 5

Junction Sequences of the Chimeric CD8a Targeting Vector

| Junction | Sequence | SEQ ID NO |
| --- | --- | --- |
| Mouse/human at exon 1 (mouse) and exon 2 (human) | TGAACCTGCTGCTGCTGGGTGAGTCGATTATCCTGGGGAGTGG AGAAGCT(AGGCCGAGCCAGTTCCGGGTGTCGCCGCTGGATCG GACCTGGAACCTGGG) | 35 |
| Human/5' of lox 2372 site | (ATGCCAGGGACAGCCCTGATACTGTAGGTAGAGTCAAGGGCT GTCCAAGT)ACCGGT*ATAACTTCGTATAAGGTATCCTATACGA AGTTAT* | 36 |
| 3' of lox 2372site/mouse | *ATAACTTCGTATAAGGTATCCTATACGAAGTTAT*CTCGACTG ATCTTGGAGGGAGACCTGGACCGGGAGACGTGCTGGGGCAGG GTT | 37 |

Human sequences are in parenthesis, lox sites are italicized, and restriction enzyme sites, multiple cloning sites, and vector-derived sequences are bolded.

Humanized CD8a targeting vector described above was electroporated into mouse ES cells that contained a humanized CD8b locus to create modified ES cells that comprise humanized CD8b and CD8a loci (FIG. 5). Targeted ES cells bearing a humanized CD8a locus were identified by genotyping using a modification of allele assay (Valenzuela et al.) that detected the presence of the human CD8a gene. Primers and probes used in the assay are depicted in Table 6 and set forth in the Sequence Listing.

TABLE 6

Primers and Probes for Genotyping Chimeric CD8α

| Region Detected | Assay | 5' primer | 3' primer | Probe |
| --- | --- | --- | --- | --- |
| Mouse exon 1 | LOA | GATGCTCTTGGCTCTT CCAGAA (SEQ ID NO: 38) | ATGAAGCCATATAGAC AACGAAGGT (SEQ ID NO: 39) | CCAGCTCCAAACTCCC CCAGCC (SEQ ID NO: 40) |
| Mouse exon 2 | LOA | TCAGCCCCAGAGACCA GAAG (SEQ ID NO: 41) | TCAATCGCTTGAGAGC ACCTAA (SEQ ID NO: 42) | TTGTCGGCCCCGTGGC TCA (SEQ ID NO: 43) |
| Human exon 2 | GOA | GCGGTTCTCGGGCAAG A (SEQ ID NO: 44) | TCAGGGCCGAGCAGAA ATAG (SEQ ID NO: 45) | ACACCTTCGTCCTCAC CCTGAGCGA (SEQ ID NO: 46) |

TABLE 6-continued

Primers and Probes for Genotyping Chimeric CD8α

| Region Detected | Assay | 5' primer | 3' primer | Probe |
|---|---|---|---|---|
| Human intron | GOA 2 | GGTTCACCTCAACCTG TTTTCC (SEQ ID NO: 47) | CGCTTCCAGGTGCGCT AA (SEQ ID NO: 48) | ACCTGGGCCCTGCTTT CAAGCC (SEQ ID NO: 49) |
| Neo | GOA | GGTGGAGAGGCTATTC GGC (SEQ ID NO: 50) | GAACACGGCGGCATCA G (SEQ ID NO: 51) | TGGGCACAACAGACAA TCGGCTG (SEQ ID NO: 52) |

LOA = loss of allele; GOA = gain of allele.

Targeted ES cells described above were used as donor ES cells and introduced into an 8-cell stage mouse embryo by the VELOCIMOUSE® method (see, e.g., U.S. Pat. No. 7,294,754 and Poueymirou et al, supra). VELOCIMICE® (F0 mice fully derived from the donor ES cell) bearing a chimeric CD8b gene and a chimeric CD8α gene were identified by genotyping using a modification of allele assay (Valenzuela et al., supra) that detects the presence of the unique human CD8b and CD8a gene sequences.

Alternatively, humanized CD8a targeting vector described herein is electroporated into mouse ES cells that do not contain a humanized CD8b locus to generate a mouse that comprises a humanized CD8a locus only.

The selection cassette in CD8a locus may be removed by methods known by the skilled artisan, e.g., as described in Example 2.1 above. In one embodiment, the selection cassette was deleted to generate MAID 1740 mouse.

Example 2.3: Expression of Chimeric CD8 in Genetically Engineered Mice

Mice heterozygous for both humanized CD8a (MAID 1740) and CD8b (MAID 1739) genes were analyzed for expression of the human CD8.

Figure 6:
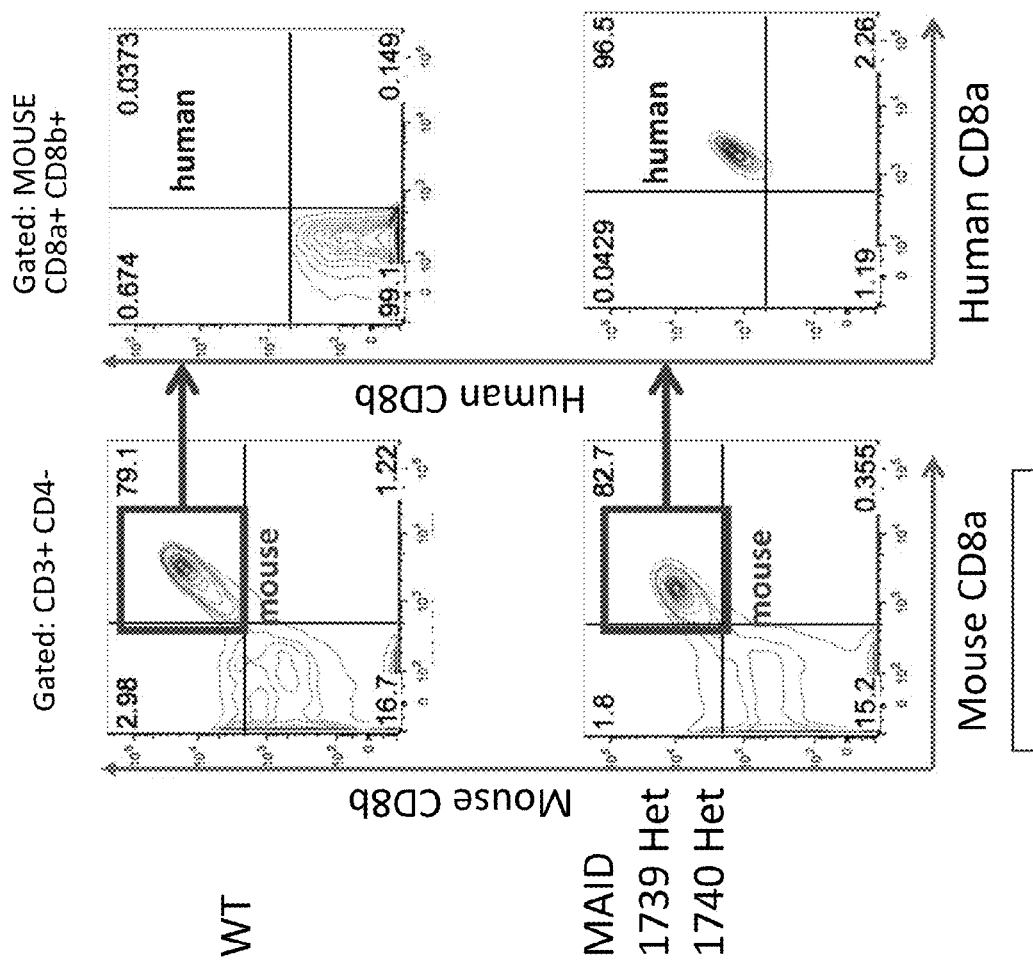
FIG. 6 is a FACS analysis with either mouse CD8b, mouse CD8a, human CD8b, or human CD8a antibodies of the splenocytes from either WT mouse or mouse heterozygous for both human CD8b and CD8a, with selection cassettes removed (1739 Het, 1740 Het).

Expression of human CD8a and CD8b was clearly detectable on the surface of CD3+CD4− T cells derived from the spleens of heterozygote but not wild type animals (FIG. 6).

Figure 7:
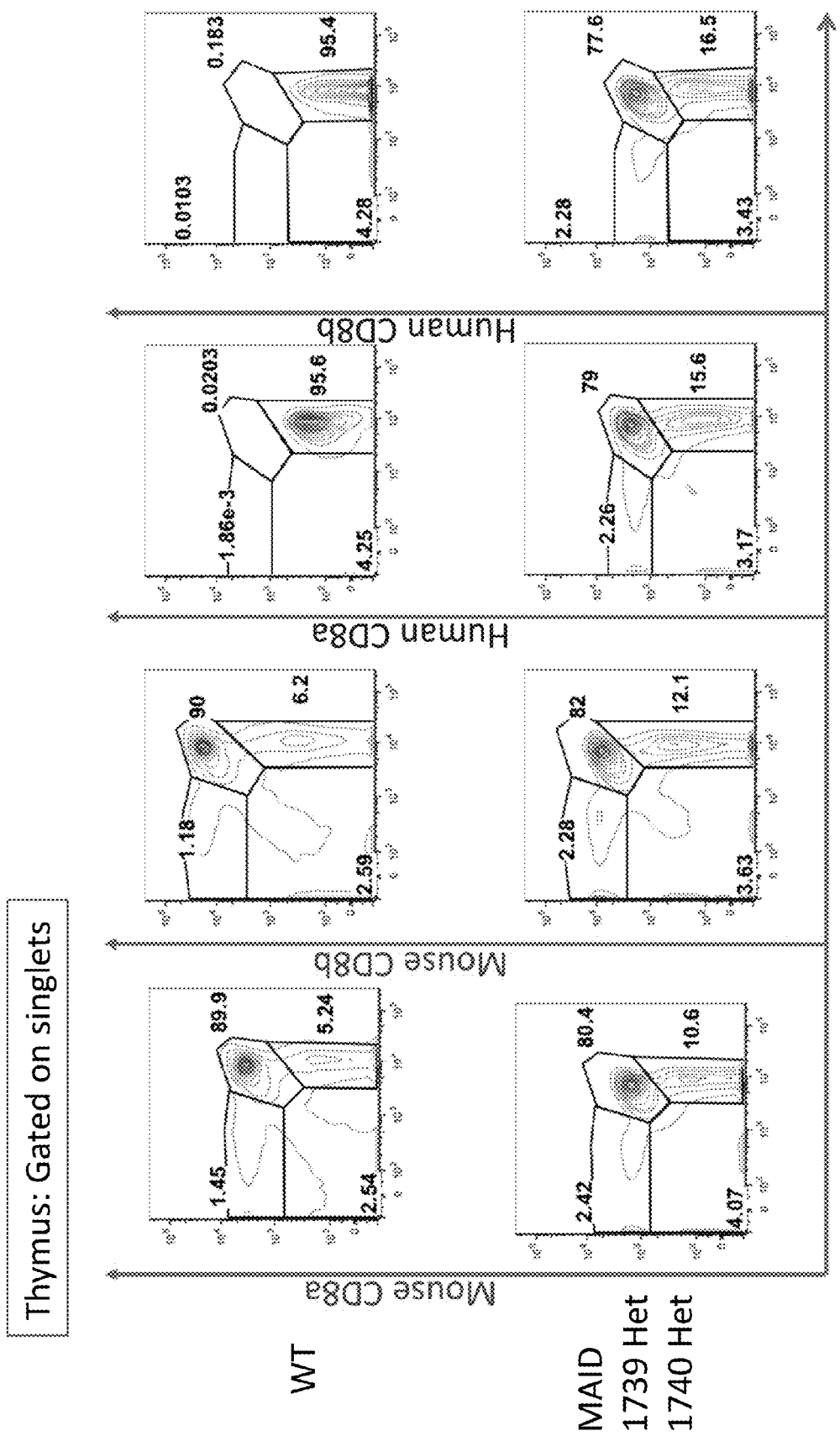
FIG. 7 is a FACS analysis with either mouse CD8b, mouse CD8a, human CD8b, human CD8a, or CD4 of thymocytes obtained from with either WT or 1739HET/1740HET mice (mice heterozygous for both CD8b and CD8a).

Expression of human CD8a and CD8b was also detectable on the surface of thymocytes obtained from heterozygous but not wild type animals (FIG. 7).

EQUIVALENTS

Those skilled in the art will recognize, or be able to ascertain using no more than routine experimentation, many equivalents of the specific embodiments of the invention described herein. Such equivalents are intended to be encompassed by the following claims.

Entire contents of all non-patent documents, patent applications and patents cited throughout this application are incorporated by reference herein in their entirety.

What is claimed is:

1. A genetically modified non-human animal comprising a first nucleotide sequence encoding a chimeric human/non-human CD8α polypeptide and a second nucleotide sequence encoding a chimeric human/non-human CD8β polypeptide,
wherein the amino acid sequence of the human portion of the chimeric human/non-human CD8α polypeptide is set forth in SEQ ID NO:59 and is operably linked to non-human transmembrane and cytoplasmic domains of a non-human CD8α polypeptide,
wherein the second nucleotide sequence comprises a nucleic acid sequence encoding a human CD8β polypeptide extracellular domain comprising at least the immunoglobulin V-like domain of the human CD8β polypeptide,
wherein the nucleic acid sequence encoding the human CD8β polypeptide extracellular domain is operably linked to a nucleic acid sequence encoding transmembrane and cytoplasmic domains of an endogenous non-human CD8β polypeptide, and
wherein the non-human animal expresses a chimeric human/non-human CD8 protein comprising the chimeric human/non-human CD8α and CD8β polypeptides.

2. The animal of claim 1, wherein the first nucleotide sequence and the second nucleotide sequence are present at an endogenous CD8 locus.

3. The animal of claim 1, wherein the animal does not express a functional endogenous non-human CD8 polypeptide from the endogenous CD8 locus.

4. The animal of claim 1, wherein the chimeric human/non-human CD8 protein is not expressed on B cells or CD4 single positive T cells.

5. The animal of claim 1, wherein the animal is a rodent.

6. The non-human animal of claim 1, wherein the non-human animal further expresses a human or humanized MHC I molecule that interacts with the chimeric human/non-human CD8 protein.

7. The non-human animal of claim 6, wherein the humanized MHC I molecule comprises α1, α2, and α3 domains of a human MHC I polypeptide and transmembrane and cytoplasmic domains of a non-human MHC I polypeptide.

8. The non-human animal of claim 1, wherein the amino acid sequence of the human portion of the chimeric human/non-human CD8β polypeptide is set forth in SEQ ID NO:58.

9. The non-human animal of claim 1, wherein the first and the second nucleotide sequences are comprised in the germline of the non-human animal.

10. The animal of claim 6, wherein the animal further comprises a human or humanized β2 microglobulin polypeptide.

11. A genetically modified mouse comprising:
(i) a first nucleotide sequence that encodes a chimeric human/mouse CD8α polypeptide, wherein the amino acid sequence of the human portion of the chimeric human/mouse CD8α polypeptide is set forth in SEQ ID NO:59 and is operably linked to mouse transmembrane and cytoplasmic domains of a mouse CD8α polypeptide, and
(ii) a second nucleotide sequence that comprises a nucleic acid sequence encoding a human CD8β polypeptide extracellular domain comprising at least the immunoglobulin V-like domain of the human CD8β polypeptide,
wherein the nucleic acid sequence encoding the human CD8β polypeptide extracellular domain is operably linked to a nucleic acid sequence encoding transmembrane and cytoplasmic domains of a mouse CD8β polypeptide, and
wherein the second nucleotide sequence encodes a chimeric human/mouse CD8β polypeptide; and
wherein the mouse expresses a chimeric human/mouse CD8 protein comprising the chimeric human/mouse CD8α and CD8β polypeptides.

12. The mouse of claim 11, wherein the first and the second nucleotide sequences are present at an endogenous CD8α and CD8β loci, respectively.

13. The mouse of claim 11, wherein the mouse does not express a functional endogenous CD8 protein from its endogenous CD8 locus.

14. The mouse of claim 11, wherein the mouse does not express the chimeric human/mouse CD8 protein on B cells or CD4 single positive T cells.

15. The mouse of claim 11, wherein the first nucleotide sequence is operably linked to mouse CD8α promoter and regulatory sequences and the second nucleotide sequence is operably linked to mouse CD8β promoter and regulatory sequences.

16. The mouse of claim 11, wherein the first and the second nucleotide sequences are comprised in the germline of the mouse.

17. The mouse of claim 11, wherein the chimeric human/mouse CD8α polypeptide comprises the amino acid sequence set forth in SEQ ID NO:54 and the chimeric human/mouse CD8β polypeptide comprises the amino acid sequence set forth in SEQ ID NO:53.

18. The mouse of claim 17, further comprising a human or humanized MHC I molecule.

19. The mouse of claim 18, wherein the humanized MHC I molecule comprises α1, α2, and α3 domains of a human MHC I polypeptide and transmembrane and cytoplasmic domains of a mouse MHC I polypeptide.

20. The mouse of claim 18, wherein the mouse further comprises a human or humanized β2 microglobulin polypeptide.

21. The mouse of claim 11, wherein the amino acid sequence of the human portion of the chimeric human/mouse CD8β polypeptide is set forth in SEQ ID NO:58.

22. A method of modifying a mouse to express a chimeric human/mouse CD8 polypeptide comprising replacing at an endogenous mouse CD8 locus (i) a nucleotide sequence encoding a CD8α polypeptide extracellular domain with a first orthologous nucleotide sequence encoding the human amino acid sequence set forth in SEQ ID NO:59 and (ii) a nucleotide sequence encoding a CD8β polypeptide extracellular domain and comprising at least exons 2-3 of an endogenous mouse CD8β locus with a second orthologous nucleotide sequence encoding a human CD8β polypeptide extracellular domain.

23. The method of claim 22, wherein the human CD8β polypeptide extracellular domain amino acid sequence is set forth in SEQ ID NO:58.

24. The method of claim 23, wherein the endogenous CD8α and CD8β loci respectively encode a chimeric human/mouse CD8α polypeptide that comprises the amino acid sequence set forth in SEQ ID NO:54 and a chimeric human/mouse CD8β polypeptide that comprises the amino acid sequence set forth in SEQ ID NO:53.

25. A method for determining whether an antigen will generate an HLA class I-restricted immune response comprising
    (i) exposing a genetically modified non-human animal to the antigen, wherein the non-human animal comprises
        (a) a first nucleotide sequence that encodes a chimeric human/non-human CD8α polypeptide of which the amino acid sequence of the human portion is set forth in SEQ ID NO:59 and is operably linked to non-human transmembrane and cytoplasmic domains of a non-human CD8α polypeptide,
        (b) a second nucleotide sequence that comprises a nucleic acid sequence encoding a human/CD8β polypeptide extracellular domain comprising at least the immunoglobulin V-like domain of the human CD8β polypeptide,
    wherein the nucleic acid sequence encoding the CD8β polypeptide extracellular domain is operably linked to a nucleic acid sequence encoding transmembrane and cytoplasmic domains of a non-human CD8β polypeptide, and
    the second nucleotide sequence encodes a chimeric human/non-human CD8β polypeptide, and
        (c) a third nucleotide sequence comprising a sequence that encodes a human or humanized MHC I polypeptide, and
    wherein the non-human animal expresses a chimeric human/non-human CD8 protein comprising the chimeric human/non-human CD8α and CD8β polypeptides and the human or humanized MHC I polypeptide; and
    (ii) detecting the absence or presence of an antigen-specific HLA class I-restricted immune response in the non-human animal;
    wherein the presence of an antigen-specific HLA class I-restricted response determines that the antigen will generate an HLA class I-restricted immune response.

26. The method of claim 25, further comprising
    (iii) identifying the antigen bound by the human or humanized MHC I polypeptide.

27. The method of claim 25, wherein the amino acid sequence of the human portion of the chimeric human/non-human CD8β polypeptide is set forth in SEQ ID NO:58.

28. The method of claim 25, wherein the chimeric human/non-human CD8α polypeptide comprises the amino acid sequence set forth in SEQ ID NO:54 and the chimeric human/non-human CD8β polypeptide comprises the amino acid sequence set forth in SEQ ID NO:53.

* * * * *